United States Patent [19]

Kamiya et al.

[11] 4,182,758

[45] Jan. 8, 1980

[54] HYDROXYAMINOHYDROCARBONPHOSPHONIC ACID DERIVATIVES AND USE THEREOF AS AN ANTIBIOTIC

[75] Inventors: Takashi Kamiya, Suita; Masashi Hashimoto, Takarzuka; Keiji Hemmi, Tsuzuki; Hidekazu Takeno, Nara, all of Japan

[73] Assignee: Fujisawa Pharmaceutical Co., Ltd., Osaka, Japan

[21] Appl. No.: 819,554

[22] Filed: Jul. 27, 1977

[30] Foreign Application Priority Data

Jul. 27, 1976 [GB] United Kingdom ............... 31339/76
Oct. 11, 1976 [GB] United Kingdom ............... 42222/76
Jun. 20, 1977 [GB] United Kingdom ............... 25700/77

[51] Int. Cl.² ............................. C07F 9/40; A01N 9/36
[52] U.S. Cl. ........................... 424/211; 260/502.4; 260/944; 260/968; 260/969; 260/978; 260/984; 260/502.5
[58] Field of Search .................. 260/944; 424/211; 260/502.5

[56] References Cited

FOREIGN PATENT DOCUMENTS 733058 of 1969 Belgium.
2115 of 1972 Japan.
46574 of 1972 Japan.
78130 of 1973 Japan.
86324 of 1974 Japan.
86325 of 1974 Japan.
87602 of 1974 Japan.
87633 of 1974 Japan.
126831 of 1974 Japan.
35343 of 1975 Japan.

*Primary Examiner*—Anton H. Sutto
*Attorney, Agent, or Firm*—Oblon, Fisher, Spivak, McClelland & Maier

[57] ABSTRACT

Hydroxyaminohydrocarbonphosphonic acid derivatives represented by the formula:

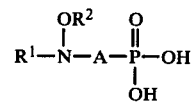

wherein
$R^1$ is hydrogen or acyl,
$R^2$ is hydrogen, lower alkyl, ar(lower) alkyl or acyl, and
A is lower alkylene, lower alkenylene or hydroxy(lower) alkylene, or the esters at the phosphono group thereof or the pharmaceutically acceptable salts thereof, excepting 3-(N-acetyl-N-hydroxyamino) propylphosphonic acid, 3-(N-acetyl-N-hydroxyamino)-2-hydroxypropylphosphonic acid, and their pharmaceutically acceptable salts, and processes for preparing the same.

Included are compounds having antimicrobial activity against various pathogenic organisms.

61 Claims, No Drawings

HYDROXYAMINOHYDROCARBONPHOSPHONIC ACID DERIVATIVES AND USE THEREOF AS AN ANTIBIOTIC

BACKGROUND OF THE INVENTION

This invention relates to new hydroxyaminohydrocarbonphosphonic acid derivatives which have antimicrobial activities against various pathogenic microorganisms, to processes for production thereof and to pharmaceutical composition comprising the same.

Firstly, it is to be noted that this invention is originated from and based upon the first and new discovery of a new antibiotic of the following formula, by isolating it from a cultured broth obtained by fermentation of a strain of the genus Streptomyces.

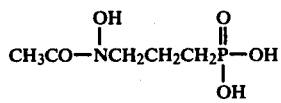

[3-(N-acetyl-N-hydroxyamino)propylphosphonic acid]

(hereinafter referred to the antibiotic FR-900098)

That is, the researchers (i.e. the inventors of U.S. application Ser. No. 819,551 filed on the same date as the filing date of this application) of the Fermentation section of the Research Laboratory of Fujisawa Pharmaceutical Co., Ltd., Japan, to which the inventors of this invention belonged, firstly and newly isolated the new antibiotic FR-900098 in pure form from a cultured broth obtained by fermentation of a strain of Streptomyces rubellomurinus ATCC No. 31215, identified the same by the physico-chemical properties and found out that the same has antimicrobial activities against various pathogenic microorganisms. Thereafter, the said antibiotic FR-900098 was delivered to the inventors of this invention for identification of the chemical structure thereof and, as the result of further study, the inventors of this invention succeeded in identifying the chemical structure and assigned the chemical structure as mentioned above to the antibiotic FR-900098.

Successively after identification of the chemical structure, the inventors of this invention have made an extensive studies on commercially advantage synthetic methods thereof, and succeeded in completing the synthetic methods for preparing the antibiotic FR-900098, and in addition to this success, the inventors of this invention succeeded in providing a lot of hydroxyaminohydrocarbonphosphonic acid derivatives other than the antibiotic FR-900098 as explained in the following disclosure of the specification.

Further, it is to be noted that the same researchers of the Fermentation section as indicated above newly discovered another antibiotic by isolating it from a culture broth obtained by fermentation of Streptomyces rubellomurinus subsp. indigoferus ATCC No. 31304 and identified the same by physico-chemical properties and also the chemical structure as assigned as follows.

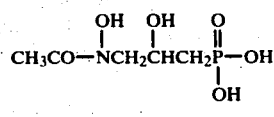

[3-(N-acetyl-N-hydroxyamino)-2-hydroxypropylphosphonic acid] (hereinafter referred to the antibiotic FR-33289)

With regard to the antibiotic FR-33289 as stated above also, the inventors of this invention made study on the commercially advantageous synthetic process thereof, and succeeded in completing the synthetic methods for preparing the antibiotic FR-33289, too.

Incidentally, it is to be noted that the invention relating to the antibiotics FR-900098 and FR-33289 per se, the methods for preparing the same by fermentation and use thereof, was filed a the U.S. patent application under the Ser. No. 819,551 on the same date as the filing date of this application.

DETAILED DESCRIPTION OF THE PREFERRED EMBODIMENT OF THE INVENTION

This invention relates to new hydroxyaminohydrocarbonphosphonic acid derivatives. More particularly, it relates to new hydroxyaminohydrocarbonphosphonic acid derivatives and, the esters and salts thereof, which have antimicrobial activities against various pathogenic microorganisms, to processes for preparation thereof, and to a pharmaceutical composition comprising the same, and to a method of use of the same for the therapeutical treatment of infectious diseases in human beings and animals.

Accordingly, it is one object of this invention to provide new hydroxyaminohydrocarbonphosphonic acid derivatives, and the esters and salts thereof which are useful as antibiotics as well as the intermediates for preparing antimicrobial substances.

Another object of this invention is to provide methods for preparation of hydroxyaminohydrocarbonphosphonic acid derivatives and the esters and salts thereof, comprising synthetic processes for preparation of the same.

A further object of this invention is to provide pharmaceutical compositions comprising one or more active ingredient(s) selected from the group of hydroxyaminohydrocarbonphosphonic acid derivatives, and the esters and salts thereof.

Hydroxyaminohydrocarbonphosphonic acid derivatives

Hydroxyaminohydrocarbonphosphonic acid derivatives of this invention can be represented by the following general formula:

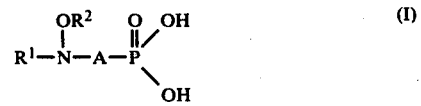

wherein
R$^1$ is hydrogen or acyl,
R$^2$ is hydrogen, lower alkyl, ar(lower)alkyl or acyl, and
A is lower alkylene, lower alkenylene or hydroxy(lower)alkylene.

Particulars of the above definitions and suitable examples thereof will be explained as follows:

As to the term "lower" used in the specification and claims, it is to be understood that "lower" is intended to mean 1 to 6 carbon atom(s), unless otherwise provided.
(1) Re: acyl for R$^1$ and R$^2$ Generally, "acyl" may be an acyl group derived from an acid such as an organic carboxylic acid, carbonic acid, carbamic acid, the thio acid or imidic acid corresponding to each of the preceding acids, or an organic sulfonic acid, each of which includes an aliphatic, an aromatic and/or a heterocyclic groups in its molecule; carbamoyl; or carbamimidoyl.

Suitable examples of said acyl are illustrated below. Aliphatic acyl means an acyl group derived from an aliphatic acid and includes:

lower alkanoyl (e.g. formyl, acetyl, propionyl, butyryl, isobutyryl, valeryl, isovaleryl, pivaloyl, etc.);

lower alkenoyl having 3–6 carbon atoms (e.g. acryloyl, methacryloyl, crotonoyl, etc.);

lower alkylthio(lower)alkanoyl (e.g. methylthioacetyl, ethylthioacetyl, etc.);

lower alkanesulfonyl (e.g. mesyl, ethanesulfonyl, propanesulfonyl, etc.);

lower alkoxycarbonyl having 2–6 carbon atoms (e.g. methoxycarbonyl, ethoxycarbonyl, propoxycarbonyl, isopropoxycarbonyl, butoxycarbonyl, isobutoxycarbonyl, etc.);

lower alkylcarbamoyl having 2–6 carbon atoms (e.g. methylcarbamoyl, etc.);

(N-lower alkyl)thiocarbamoyl having 2–6 carbon atoms [e.g. (N-methyl)thiocarbamoyl, etc.];

lower alkylcarbamimidoyl (e.g. methylcarbamimidoyl, etc.);

oxalo;

lower alkoxalkyl having 2–6 carbon atoms (e.g. methoxalyl, ethoxalyl, propoxalyl, etc.).

In the above exemplified aliphatic acyl, the aliphatic hydrocarbon moiety, particularly alkyl group and alkane moiety may have optionally one or more suitable substituent(s) such as amino, halogen (e.g. fluorine, chlorine, bromine, etc.), hydroxy, hydroxyimino, carboxy, alkoxy (e.g. methoxy, ethoxy, propoxy, etc.), alkoxycarbonyl, acylamino (e.g. benzyloxycarbonylamino, etc.), acyloxy (e.g. acetoxy, benzoyloxy, etc.), and the like, and preferred aliphatic acyl having such substituents may be exemplified by alkanoyl substituted by amino, carboxy, amino and carboxy, halogen, acylamino or the like.

Aromatic acyl means an acyl group derived from an acid having substituted or unsubstituted aryl group, in which the aryl group may include phenyl, tolyl, xylyl, naphthyl and the like, and suitable examples thereof are illustrated as follows.

aroyl (e.g. benzoyl, toluoyl, xyloyl, naphthoyl, phthaloyl, etc.);

ar(lower)alkonoyl (e.g. phenylacetyl, etc.);

ar(lower)alkenoyl (e.g. cinnamoyl, etc.);

aryloxy(lower)alkanoyl (e.g. phenoxyacetyl, etc.);

arylthio(lower)alkanoyl (e.g. phenylthioacetyl, etc.);

arylamino(lower)alkanoyl (e.g. N-phenylglycyl, etc.);

arenesulfonyl (e.g. benzenesulfonyl, tosyl, naphthalenesulfonyl, etc.);

aryloxycarbonyl (e.g. phenoxycarbonyl, naphthyloxycarbonyl, etc.);

ar(lower)alkoxycarbonyl (e.g. benzyloxycarbonyl, etc.);

arylcarbamoyl (e.g. phenylcarbamoyl, naphthylcarbamoyl, etc.);

arylglyoxyloyl (e.g. phenylglyoxyloyl, etc.)

In the above exemplified aromatic acyl, the aromatic hydrocarbon moiety (particularly aryl moiety) and/or aliphatic hydrocarbon moiety (particularly alkane moiety) may have optionally one or more suitable substituent(s), such as the same as those exemplified as the suitable substituent for alkyl group and alkane moiety as mentioned above. Particularly, and preferred aromatic acyl having such substituents may be exemplified by aroyl substituted by halogen and hydroxy, or halogen and acyloxy or the like, and ar(lower)alkanoyl substituted by hydroxy, hydroxyimino, dihaloalkanoyloxyimino, or the like.

arylthiocarbamoyl (e.g. phenylthiocarbamoyl, etc.);

arylcarbamimidoyl (e.g. phenylcarbamimidoyl, etc.); and the like.

Heterocyclic acyl means an acyl group derived from an acid having heterocyclic group and includes:

heterocyclic carbonyl, in which the heterocycle moiety is 5 to 6 membered heterocycle containing at least one hetero atom selected from nitrogen, oxygen and sulfur (e.g. thenoyl, furoyl, pyrrolecarbonyl, nicotinoyl, etc.);

heterocycle(lower)alkanoyl, in which the heterocycle moiety is 5 to 6 membered heterocycle containing at least one hetero atom selected from nitrogen, oxygen and sulfur (e.g. thienylacetyl, furylacetyl, imidazolylpropionyl, tetrazolylacetyl, 2-(2-amino-4-thiazolyl)-2-methoxyiminoacetyl, etc.); and the like.

In the above exemplified heterocyclic acyl, heterocycle moiety and/or the aliphatic hydrocarbon moiety may have optionally one or more suitable substituent(s) such as the same as those exemplified as the suitable substituent for alkyl group and alkane moiety as mentioned above.

(2) Re: lower alkyl for $R^2$

"Lower alkyl" may include a straight or branched alkyl group containing up to 6 carbon atoms, such as methyl, ethyl, propyl, isopropyl, butyl, isobutyl, tert-butyl, pentyl, hexyl and the like.

(3) Re: ar(lower)alkyl for $R^2$

"Ar(lower)alkyl" may include mono-, di- or triphenyl(lower)alkyl such as benzyl, phenethyl, benzhydryl, trityl and the like, of which arene moiety may have optionally one or more suitable substituent(s) such as alkoxy (e.g. methoxy, ethoxy, etc.), halogen (e.g. fluorine, chlorine, bromine, etc.), nitro and the like.

(4) Re: lower alkylene for A

"Lower alkylene" may include a straight or branched (lower)alkylene group containing up to 6 carbon atoms, which can also be represented by the formula: $-(C_nH_{2n})-$ wherein n is an integer of 1 to 6, such as methylene, ethylene, trimethylene, methylethylene, tetramethylene, 1-methyltrimethylene, 2-ethylethylene, pentamethylene, 2-methyltetramethylene, isopropylethylene, hexamethylene and the like, and particularly the preferred may be alkylene having up to 4 carbon atoms and the most preferred may be one having 3 carbon atoms (e.g. trimethylene.)

(5) Re: lower alkenylene for A

"Lower alkenylene" may include a straight or branched(lower)alkenylene group containing up to 6 carbon atoms, which can also be represented by the formula: $(C_nH_{2n-2})$ wherein n is an integer of 2 to 6, such as vinylene, propenylene (e.g. 1-propenylene, 2-propenylene), 1-methylpropenylene, 2-methylpropenylene, butenylene, 2-ethylpropenylene, pentenylene, hexenylene and the like, and particularly the preferred may be alkenylene having up to 5 carbon atoms and most preferred may be one having 3 carbon atoms [e.g. 1-propenylene].

(6) Re: hydroxy(lower)alkylene for A

"Hydroxy(lower)alkylene" may include a straight or branched (lower)alkylene group containing up to 6 carbon atoms, whose optional carbon is substituted with one hydroxy group and said hydroxyalkylene can also be represented by the formula:—$(C_{n2n-1})(OH)$— wherein n is an integer of 1 to 6. Suitable examples of said hydroxyalkylene may include hydroxymethylene, hydroxyethylene (e.g. 1-hydroxyethylene and 2-hydroxyethylene), hydroxytrimethylene (e.g. 1-hydroxytrimethylene, 2-hydroxytrimethylene and 3-hydroxytrimethylene), hydroxytetramethylene (e.g. 2-hydroxytetramethylene), 2-hydroxy-2-methyltrimethylene, hydroxypentamethylene (e.g. 2-hydroxypentamethylene), hydroxyhexamethylene (e.g. 2-hydroxyhexamethylene) and the like. Particularly, as to such hydroxyalkylene, the preferred may be hydroxy(lower)alkylene containing up to 4 carbon atoms and the most preferred may be one containing 3 carbon atoms (e.g. 2-hydroxytrimethylene).

Suitable examples of the esters at the phosphono group of the object compound (I) may include conventional mono- and di-ester, and preferred examples of such ester may include lower alkyl ester (e.g. methyl ester, ethyl ester, propyl ester, isopropyl ester, butyl ester, isobutyl ester, hexyl ester, etc.); an ar(lower)alkyl ester (e.g. benzyl ester, phenethyl ester, benzhydryl ester, trityl ester, etc.), an aryl ester (e.g. phenyl ester, tolyl ester, naphthyl ester, etc.), aroyl(lower)alkyl ester (e.g. phenacyl ester, etc.); and an ester of silyl compound [e.g. trialkylhalosilane, dialkyldihalosilane, alkyltrihalosilane, dialkylarylhalosilane, trialkoxyhalosilane, dialkylaralkylhalosilane, dialkoxydihalosilane trialkoxyhalosilane, etc.], and the like.

In the above ester, the alkane and/or arene moiety may optionally bear at least one suitable substituent such as halogen, alkoxy, hydroxy, nitro or the like. In this respect, it is to be noted that the ester at the phosphono group of the object compound (I) can be represented by the following formula (I') for convenience' sake.

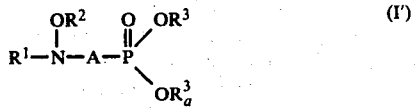

(I')

wherein
$R^3$ is hydrogen or a residue of the ester, and
$R_a^3$ is a residue of the ester Suitable examples of the salts of the object compound (I) and the esters may include an acid addition salt with an organic or inorganic acid (e.g. hydrochloride, hydrobromide, sulfate, nitrate, methanesulfonate, p-toluenesulfonate, acetate, lactate, maleate, fumalate, oxalate, tartarate, benzoate, etc.), a salt with an organic or inorganic base (e.g. sodium salt, potassium salt, calcium salt, alminum salt, ammonium salt, magnesium salt, triethylamine salt, ethanolamine salt, dicyclohexylamine, salt, ethylenediamine salt, N,N'-dibenzylethylenediamine salt, etc.) and a salt with an amino acid (e.g. arginine salt, aspartic acid salt, glutamic acid salt, etc.) and the like.

It is to be understood that the object compound (I) may include geometric isomers (i.e. cis-and trans-isomers, and syn-and anti-isomers), and optical isomers (d- and l-isomers, or their mixture) according to the chemical structure thereof.

According to this invention, the object compound (I), the ester at the phosphono group thereof and salt thereof can be prepared by various processes, details of which will be explained as follows.

Production of hydroxyaminohydrocarbonphosphonic acid derivatives

The compound (I), and the esters at the phosphono group thereof and the salts thereof can be produced by various synthetic processes, which can be classified as follows.

I. Processes for construction of skeletal structure
(1) Formation of C-P bond
(2) Formation of C-N bond
(3) Formation of hydroxyamino function
II. Process for transformation of functional groups
(1) Hydrolysis (I)
(2) Hydrolysis (II)
(3) N-Acylation
(4) O-Acylation
(5) Esterification
(6) Formation of C-S bond Each of these processes will be illustrated hereinafter.

I. Processes for construction of skeletal structure
(1) Formation of C-P bond
The reaction of this process can be illustrated by the following scheme:

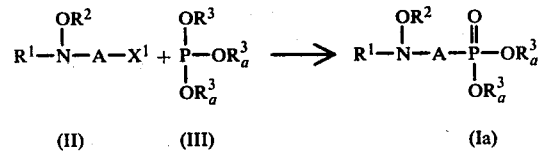

wherein
$R^1$, $R^2$ and A are each as defined above;
$R^3$ is hydrogen or a residue of the ester;
$R_a^3$ is a residue of the ester, and
$X^1$ is an acid residue.

Preferred examples of the acid residue for $X^1$ of the starting compound (II) may include halogen (e.g. chlorine, bromine, iodine, etc.), alkanesulfonyloxy (e.g. mesyloxy, ethanesulfonyloxy, etc.), arenesulfonyloxy (e.g. benzenesulfonyloxy, tosyloxy, etc.), and the like.

A residue of the ester for $R^3$ and $R_a^3$ of the starting compound (III), as illustrated hereinabove in the explanation of the object compound (I), may include lower alkyl, ar(lower)alkyl and aryl, and preferred examples are the same as those illustrated hereinabove. Among such residue of the ester, lower alkyl is preferable.

Further, it is to be understood that preferred examples of the group as defined for $R^1$, $R^2$ and A are the same as those illustrated hereinabove in the explanation of the object compound (I), respectively.

In this process, the object compound (Ia) can be prepared by reacting the compound (II) or the acid addition salt thereof with the compound (III). Suitable examples acid addition salt of the compound (II) are the same as those illustrated hereinabove in the explanation of the salt of the compound. (I).

The starting compound (II) includes known and novel ones. The known compounds, e.g. N-(3-bromopropyl)-N-benzyloxy-p-toluenesulfonamide, are prepared by the method described in Bulletin of the Chemical Society of Japan Vol. 45, page 1462 (1972), and the other new compounds can also be prepared in the similar manner thereto. The detailed method for preparing said new compound is to be referred to Preparation of starting compounds as described hereinafter.

The reaction of this process can be conducted in the presence or absence of solvents. Preferred solvents may include conventional ones such as benzene, toluene, xylene, pyridine, dimethylsulfoxide, N,N-dimethylformamide, etc. The reaction is conducted usually with the range of ambient temperature to heating.

The reaction of this process can also be conducted in the presence of an organic or inorganic base such as alkali metal (e.g. lithium, sodium, potassium, etc.), alkaline earth metal (e.g. calcium, magnesium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium t-butoxide, etc.), trialkylamine (e.g. triethylamine, etc.), pyridine, diazabicyclo compound (e.g. 1,5-diazabicyclo[3,4,0]nonene-5, 1-5-diazabicyclo[5,4,0]undecene-5, etc.), quaternary ammonium salt (e.g. triton B, etc.) and the like.

Optimum reaction conditions can be selected from the above reaction conditions according to kinds of the starting compound, solvent, and/or base to be used.

For example, in the case of using dialkyl phosphonate as a starting compound, i.e. the compound (III), wherein $R^3$ is hydrogen and $R_a^3$ is a residue of ester, the reaction can preferably be conducted in the presence of a solvent and a base. On the other hand, in the case of using trialkylphosphite as a starting compound, i.e. the compound (III) wherein $R^3$ and $R_a^3$ are each a residue of ester, the reaction can usually be conducted in the absence of solvent and base.

The object compound (Ia) can be isolated and purified in a conventional manner (e.g. evaporation, extraction, chromatography, salt formation, crystallization and so on.)

(2) Formation of C-N bond

The reaction of this process can be illustrated by the following scheme:

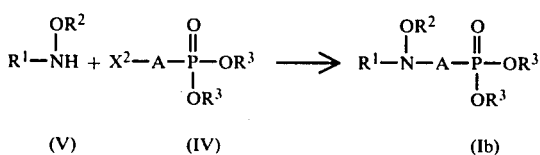

(V)      (IV)                    (Ib)

wherein $R^1$, $R^2$, $R^3$ and A are each as defined above, and $X^2$ is an acid residue.

Preferred examples of the acid residue for $X^2$ of the compound (IV) are the same as those illustrated for $X^1$ hereinabove. Further, it is to be understood that preferred examples of the groups as defined for $R^1$, $R^2$, $R^3$ and A are the same as those illustrated hereinbefore, respectively.

In this process, the object compound (Ib) or the salt thereof also be prepared by reacting the compound (IV) or the salt thereof with the compound (V) or the salt thereof. Suitable examples of the salts of the compounds (Ib), (IV) and (V) are the same as those illustrated hereinabove in the explanation of the salt of the compound (I).

The starting compound (IV) includes known and novel ones. The known compounds, e.g. diethyl 3-bromopropylphosphonate, and 3-bromopropylphosphonic acid, are prepared by the method described in Journal of the American Chemical Society Vol. 66, page 1511 (1944), and the other new compounds can also be prepared in the similar manner thereto.

The other starting compound (V) also includes known and novel ones. The known compounds, e.g. N-benzyloxy-p-toluenesulfonamide, are prepared by the method described in Bulletin of the Chemical Society of Japan Vol. 45, page 1462 (1972), and the other new compounds can be prepared in the similar manner thereto. The detailed method for preparation of the starting compounds (IV) and (V) is to be referred to Preparation of starting compounds as described hereinafter.

The reaction of this process is usually conducted in a conventional solvent such as methanol, ethanol, propanol, benzene, toluene, pyridine, dimethylsulfoxide, N,N-dimethylformamide, etc. There is no limitation to this reaction temperature and this reaction may be preferably conducted within the range of ambient temperature to heating.

The reaction of this process can preferably be conducted in the presence of an organic or inorganic base such as alkali metal (e.g. sodium), alkaline earth metal (e.g. calcium), alkali metal hydride (e.g. sodium hydride), alkali metal alkoxide (e.g. sodium ethoxide), alkali metal hydroxide (e.g. sodium hydroxide), alkali metal bicarbonate (e.g. sodium bicarbonate), trialkylamine (e.g. triethylamine), diazabicyclo compound (e.g. 1,5-diazabicyclo[3,4,0]nonene-5, 1,5-diazabicyclo[5,4,0]undecene-5, etc.) and the like.

When a starting compound (IV) wherein A is hydroxyalkylene group is used in this reaction, it is preferable to conduct the reaction by protecting said hydroxy group with an easily removable group such as tetrahydropyranyl and the like. In such a case, the object compound (Ib) may be obtained in the form of a compound (IV) having protected hydroxy group on the alkylene group thereof. And such a protective group can easily be hydrolyzed in a conventional manner as described in the working examples hereinafter.

Optimum reaction conditions can be selected from the above reaction conditions according to kinds of starting compound, solvent, and/or base to be used.

The object compound [Ib] of the salt thereof can be isolated and purified in a conventional manner as explained in the foregoing Process I(1) and the following Process I(3), respectively.

(3) Formation of hydroxyamino function

The reaction of this process can be illustrated by the following scheme:

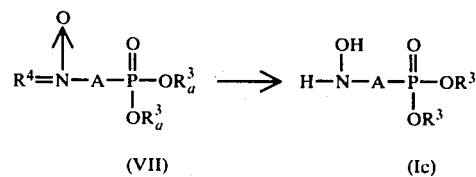

(VII)                      (Ic)

wherein $R^3$, $R_a^3$, and A are each as defined above, and $R^4$ is alkylidene.

Preferred examples of alkylidene for $R^4$ of the starting compound (VII) may include a lower and higher alkylidene such as methylene, ethylidene, propylidene, isoporpylidene, butylidene, isobutylidene, pentylidene, hexylidene, heptylidene, octylidene, nonylidene, decylidene, etc.

Further, it is to be understood that preferred examples of the groups as defined for $R_a^3$, $R^3$ and A are the same as those illustrated hereinbefore.

In this process, the object compound (Ic) can be prepared by subjecting the compound (VII) to hydrolysis.

The starting compound (VII) is novel and can be prepared, for example, by reacting an alkanal - or alkanone-oxime with the compound (IV) wherein $R^3$ is a residue of the ester as mentioned in the foregoing Process (I) (2). The detailed method for preparation of the starting compound (VII) is to be referred to Preparation of starting compounds as described hereinafter.

The hydrolysis is conducted in a conventional manner, and preferably conducted in the presence of an acid. Preferred examples of the acid are an inorganic acid such as hydrochloric acid, hydrobromic acid, sulfuric acid and the like and an organic acid such as formic acid, trifluoroacetic acid and the like.

The hydrolysis is usually carried out in any solvent which does not have an adverse influence on the reaction, e.g. water, methanaol, ethanol, propanol, isopropanol, acetic acid and the like, and preferably carried out at ambient temperature or under heating.

It is noted that in this process, the ester (i.e. —$OR_a^3$ wherein $R_a^3$ is a residue of the ester) group at the phosphono group of the compound (VII) may be occasionally hydrolyzed to produce phosphonic acid compound (Ic), wherein $R^3$ is hydrogen together with the hydrolytic cleavage of the C=n bond, and this case is also included with the scope of this process.

The object compound (Ic) can be isolated and purified in a conventional manner and can also be transformed into an acid addition salt with an organic or inorganic acid, such as formate, acetate, trifluoroacetate, p-toluenesulfonate, hydrochloride, hydrobromide, sulfate and the like, and further, in case that the object compound (Ic) is produced as a free phosphonic acid, it can also be transformed into an organic or inorganic base such as sodium salt, potassium salt, calcium salt, triethylamine salt, ethanolamine salt and the like.

II. Process for transformation of function groups (1) Hydrolysis (I)

The reaction of this process can be illustrated by the following scheme:

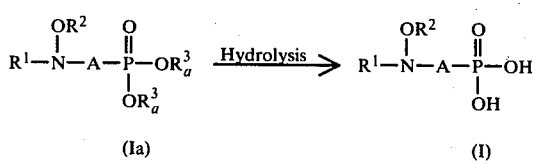

(Ia)    (I)

wherein $R^1$, $R^2$, $R_a^3$ and A are each as defined above.

It is to be understood that preferred examples of the groups as defined for $R^1$, $R^2$, $R_a^3$ and A are the same as those illustrated hereinbefore.

In this process, the object compound (I) can be prepared by hydrolyzing compound (Ia) or the acid addition salt thereof. Suitable examples of the acid addition salt are the same as those illustrated hereinabove in the explanation of the salt of the compound (I).

The method of this hydrolysis includes conventional ones such as a hydrolysis in the presence of an organic or inorganic acid and a combination method comprising transformation of the ester excepting silyl ester of compound (Ia) into a silyl ester and subsequent hydrolysis of the residue silyl ester.

The hydrolysis can preferably be conducted in the presence of an organic or inorganic acid such as hydrochloric acid, hydrobromic acid, sulfuric acid, trifluoroacetic acid, formic acid and the like, which can be used in a conventional hydrolysis under acidic conditions.

The hydrolysis is usually conducted in a conventional solvent such as water, methanol, ethanol, propanol, isopropanol, acetic acid and the like, and preferably at ambient temperature or under heating.

Further, in case that the ester of the compound (Ia) (i.e.—$OR_a^3$ wherein $R_a^3$ is a residue of the ester) is the lower alkyl ester (i.e.—$OR_a^3$ wherein $R_a^3$ is lower alkyl) or the ar(lower)alkyl ester (i.e.—$OR_a^3$ wherein $R_a^3$ is ar(lower)alkyl), the object compound (I) can also be prepared by transforming said lower alkyl ester or ar(lower)alkyl ester into the silyl ester (i.e.—$OR_a^3$ wherein $R_a^3$ is a residue of the silyl compound) by the reaction of the compound (Ia) and a silyl compound as the first step and then by subsequent hydrolysis of the resultant silyl ester as the second step.

The silyl compound to be used in the first step for the combination method may include trialkylhalosilane, dialkyldihalosilane, alkyltrihalosilane, dialkylarylhalosilane, triarylhalosilane, dialkylaralkylhalosilane, dialkoxydihalosilane, trialkoxyhalosilane, and the like.

The reaction of the compound (Ia) with the silyl compound is usually carried out in the presence of or absence of solvents under anhydrous condition. preferred solvents may include tetrahydrofuran, dioxane, benzene, pyridine, chloroform, dichloromethane, N,N-dimethylformamide, dimethylsulfoxide and the like.

There is no limitation to the reaction temperature for the reaction of compound (Ia) with a silyl compound and this reaction is preferably conducted under cooling to warming.

The silyl compound is preferably used in an amount of 2 or more molar equivalents to 1 mole of the compound (Ia).

The subsequent hydrolysis can be conducted in a similar manner to one as illustrated above for the direct hydrolysis method of this process and is preferably conducted by treating said reaction mixture, without any isolation of the resultant product, directly with water.

In this process, the functional group of compound (Ia), i.e. acyl group(s) as defined for $R^1$ and/or $R^2$, or aralkyl group(s) as defined for $R^2$, may occasionally be removed off to transform into hydrogen together with the hydrolysis of the object phosphonic acid ester linkage, and these cases are also included within the scope of this process.

When, in this reaction, there is used a starting compound (Ia) wherein A is hydroxyalkylene group, in which the hydroxy group is protected with an easily removable protective group such as pyranyl and the like, such a protective group can usually be removed off by the hydrolysis of this process to provide the object compound (I) wherein A is hydroxyalkylene group, and this case is also included within the scope of this process.

The object compound (I) can be isolated and purified in a conventional manner in the free form or in the form of salt with an organic or inorganic acid, such as p-toluenesulfonate, hydrochloride, hydrobromide, sulfonate and the like, or of salt with an organic or inorganic base, such as sodium salt, potassium salt, calcium salt, triethylamine salt and the like.

Further, a salt of the compound (I) can also be transformed, on the occasion of demand, into another salt of the same and reversely converted into the free form of the same in a conventional manner.

(2) Hydrolysis (II)

The reaction of this process can be illustrated by the following scheme:

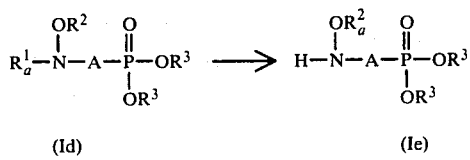

(Id)          (Ie)

wherein $R^2$, $R^3$ and A are each as defined above, $R_a^1$ is acyl, and $R_a^2$ is hydrogen or alkyl.

Preferred examples of the acyl for $R_a^1$ are the same as those hereinabove illustrated for the acyl in $R^1$. It is to be understood that preferred examples of the groups as defined for $R^2$, $R^3$ and A of the compound (Id) are the same as those illustrated hereinabove. Suitable examples of the salt of the compound (Id) are the same as those illustrated hereinabove for the salt of the compound (I).

In this process, the object compound (Ie) can be prepared by hydrolyzing the compound (Id).

The hydrolysis is usually conducted in a conventional solvent such as water, methanol, ethanol, propanol, isopropanol, acetic acid, and the like, and preferably at ambient temperature or under heating.

The hydroylsis can preferably be conducted in the presence of an organic or inorganic acid, such as hydrochloric acid, hydrobromic acid, sulfuric acid, trifluoroacetic acid, formic acid and the like, and an organic or inorganic base such as alkali metal hydroxide (e.g. lithium hydroxide, sodium hydroxide, potassium hydroxide, etc.), alkalimetal alkoxide (e.g. lithium methoxide, sodium ethoxide, potassium t-butoxide, etc.), a quaternary ammonium salt (e.g. tetramethylammonium hydroxide, tetraethylammonium hydroxide, dimethyldibenzylammonium hydroxide, etc.) or the like.

In this process, one or two or the ester at the phosphono group (i.e. —$OR^3$ wherein $R^3$ is a residue of the ester of compound (Id) may occasionally be subjected to hydrolysis to be transformed into the hydroxy group (i.e. —$OR^3$ wherein $R^3$ is hydrogen), and this case is also included within the scope of this process.

The object compound (Ie) can be isolated and purified in a conventional manner in the free form or in the form of salt with an organic or inorganic acid, such as p-toluenesulfonate, hydrochloride, hydrobromide, sulfate and the like, or of salt with an organic or inorganic base, such as sodium salt, potassium salt, calcium salt, triethylamine salt and the like.

Further, a salt of the compound (Ie) can also be transformed, on the occasion of demand, into another salt of the same and reversely converted into the free form of the same in a conventional manner.

(3) N-Acylation

The reaction of this process can be illustrated by the following scheme:

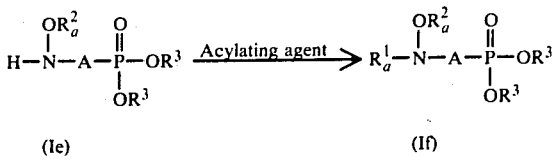

(Ie)          (If)

wherein $R_a^1$, $R_a^2$ and $R^3$ and A are each as defined above.

In this process, the object compound (If) or the salt thereof can be prepared by reacting the starting compound (Ie) or the salt thereof with an acylating agent. Suitable examples of the salt of the compounds (If) and (Ie) are the same as those hereinabove illustrated for the salts of the compound (I).

The starting compound (Ie) can preferably be prepared by the foregoing process II (2).

It is to be understood that preferred examples of the groups as defined for $R_a^2$, $R^3$ and A of the compound (Ie) are the same as those illustrated hereinbefore.

The acylating agent to be used in this reaction includes an organic acid ($R_a^1$—OH wherein $R_a^1$ is acyl group) such as monobasic or dibasic organic carboxylic acid, an organic carbonic acid or an organic carbamic acid and the corresponding thio acid or imidic acid; and an organic sulfonic acid, more particularly, aliphatic, aromatic or heterocyclic carboxylic acid, and the corresponding carbonic, carbamic, thiocarboxylic, thiocarbonic, thiocarbamic, carboximidic, carbamimidic acid, and sulfonic acid; their reactive derivatives; and also includes an isocyanate (e.g. potassium-, alkyl- or arylisocyanate), isothiocyanate (e.g. alkyl isothiocyanate) and an isothiourea (e.g. ethyl isothiourea).

And suitable examples of these organic acids are to be referred to the corresponding organic acids to those comprising the acyl groups as exemplified hereinabove in details in the descriptions of suitable examples of acyl groups for $R^1$ of the compound (I).

Said organic acid as an acylating agent can be used in the form of an activated organic acid, i.e. as a reactive derivative of the acid. As such reactive derivatives of said organic acids, there may be exemplified an acid halide, an acid azide, an acid anhydride, an activated amide, an activated ester, etc., and additionally isocyanate and isothiocyanate can preferably be used as reactive derivative of carbamic and thiocarbamic acids, respectively.

Preferred examples of such reactive derivatives are illustrated by:

an acid halide (e.g. acid chloride, acid bromide, etc.);

an acid azide;

an acid anhydride including a mixed acid anhydride with an acid sucn as dialkylphosphoricc acid, phenylphosphoric acid; diphenylphosphoric acid, dibenzylphosphoric acid, halogenated phosphoric acid, dialkylphosphorous acid, sulfurous acid, thiosulfuric acid, sulfuric acid, monoalkylcarbonic acid, aliphatic carboxylic acid (e.g., acetic acid, pivalic acid, pentanoic acid, isopentanoic acid, 2-ethylbutyric acid or trichloroacetic acid), aromatic carboxylic acid (e.g., benzoic acid), and symmetrical acid anhydride;

an activated amide with pyrazole, imidazole, 4-substituted imidazole, dimethylpyrazole, triazole or tetrazole; and an activated ester such as methyl thioester, phenyl thioester, p-nitrophenyl thioester, p-cresyl thioester, carboxymethyl thioester, pyranyl ester, pyridyl ester, piperidyl ester, 8-quinolyl thioester, or ester with N,N-dimethylhydroxylamine, 1-hydroxy-2-(1H)-pyridone, N-hydroxysuccinimide, N-hydroxyphthalimide or 1-hydroxy-6-chlorobenzotriazole, and the like.

The above reactive derivatives are selected according to the kind of the acid to be used.

In the reaction, when free acid is used as an acylating agent, the acylation reaction may preferably be conducted in the presence of condensing agent such as carbodiimidic compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus compound (e.g. phosphorus oxychloride, phosphorus trichloride, etc.), thionyl chloride, oxalyl chloride, 2-ethyl-7-hydroxybenzisoxazolium salt, 2-ethyl-5-(m-sulfophenyl)isoxazolium hydroxide, (chloromethylene)dimethylammonium chloride,2,2,4,4,6,6,-hexachloro-1,3,5,2,4,6-triazatriphorine, 1-benzenesulphonyloxy-6-chloro-1H-benzotriazole, p-toluenesulfonyl chloride, isopropoxybenzenesulfoxyl chloride, or a mixed condensing agent such as triphenylphosphine and a carbon tetrahalide (e.g. carbon tetrachloride, carbon tetrabromide, etc.) or a complex of N,N-dimethylformamide with phosphoryl chloride, phosgene or thionyl chloride, etc., and the like.

The reaction is usually conducted in a solvent such as water, methanol, ethanol, propanol, acetone, ethyl ether, dioxane, acetonitrile, ethylacetate, N,N-dimethylformamide, dimethylsulfoxide, tetrahydrofuran, dichloromethane, chloroform, etc. or pyridine, N-methylmorpholine, N-methylpyrrolidine and other conventional solvents, and a mixture thereof.

The reaction can also be conducted preferably in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

And, among said base, a liquid one can also be used as a solvent.

There is no limitation to this reaction temperature and this reaction may preferably be conducted within the range of cooling to ambient temperature.

When this acylation reaction is conducted by using the starting compound (Ie), wherein $R_a{}^2$ is hydrogen, and an excess amount of the acylating agent, there may occasionally produce N,O-diacylated compound, i.e., a compound of the formula corresponding to the formula (If) wherein $R_a{}^2$ is also acyl, together with the object N-monoacyl compound (If) wherein $R_a{}^2$ is hydrogen, and in such case, N,O-diacylated compound can easily be transformed into the object N-monoacyl compound by treating it with aqueous alkaline solution. These cases are also included within the scope of this process.

In case that the acyl group for $R_a{}^1$ of the object compound (If) prepared by this process is an acyl bearing functional group(s), such as alkoxycarbonyl, acylamino, acyloxy group (e.g. alkoxalyl, acylaminoalkanoyl, acyloxyalkanol, acyloxaroyl, etc.) and the like, said object compounds can also be transformed by hydrolysis into the corresponding acyl compound of which acyl group for $R_a{}^1$ is an acyl bearing the corresponding functional group(s) such as carboxy, amino, hydroxy, and the like (e.g. oxalo, aminoalkanoyl, hydroxyalkanoyl, hydroxyaroyl, etc.)

The hydrolysis is usually conducted in a conventional solvent such as water, methanol, ethanol, propanol, isopropanol and the like, and preferably under rather mild conditions such as at ambient temperature or under cooling.

The hydrolysis can preferably be conducted in the presence of a base such as sodium hydroxide, potassium hydroxide and the like, and of an acid such as hydrochloric acid, hydrobromic acid, sulfuric acid, trifluoroacetic acid, formic acid and the like.

These cases are also included within the scope of this process.

In case that the acyl group for $R_a{}^1$ of the object compound (If) prepared by this process is an acyl having oxalyl (—COCO—) group (e.g. arylglyoxyloyl, etc.) and the like said object compounds can also be transformed by a conventional reduction into the corresponding acyl compound of which acyl group for $R_a{}^1$ is an acyl having hydroxymethylenecarbonyl

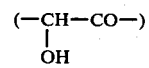

group (e.g. arylglycoloyl, etc.) and the like.

The reduction is preferably conductd with a reducing agent such as alkali metal borohydride (e.g. sodium borohydride, etc.), an alkali metal aluminum hydride (e.g. Lithium aluminum hydride, etc.), a combination of alkali metal and alcohol and the like, in a conventional solvent such as water, methanol, ethanol, ether tetrahydrofuran, benzene and the like, at cooling to the boiling point of the solvent to be used.

These cases are also included within the scope of this process.

The reaction product (If) can be isolated and purified optionally in the form of free phosphonic acid or of salt with a base in a conventional manner as those illustrated hereinabove.

(4) O-Acylation

The reaction of this process can be illustrated by the following scheme:

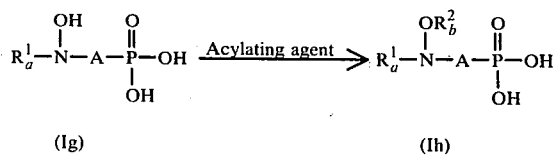

wherein $R_a{}^1$ and A are each as defined above, and $R_b{}^2$ is acyl.

In this process, the object compound (Ih) or the salt thereof can be prepared by reacting the compound (Ig)

or the salt thereof with an acylating agent. Suitable examples of the salts of the compound (Ih) and (Ig) are the same as those illustrated hereinabove for the salt of the compound (I).

It is to be understood that preferred examples of the groups as defined for $R_a{}^1$ and A of the compound (Ig) are the same as those illustrated hereinbefore, respectively.

The acylating agent to be used in this reaction includes an organic acid ($R_b{}^2$—OH, wherein $R_b{}^2$ is acyl group) and their reactive derivatives.

Suitable examples of the organic acid ($R_b{}^2$—OH) and their reactive derivatives are the same as those illustrated in the explanations of the organic acid ($R_a{}^1$—OH) and their reactive derivatives in the foregoing N-acylation process II (3).

The reaction of this acylation, and isolation and purification of the object compound (Ih) are also conducted in substantially the same manner as those illustrated in the foregoing N-Acylation process II (3).

(5) Esterification

The reaction of this process can be illustrated by the following scheme:

(Ii)        (Ij)

wherein $R_a{}^1$, $R^2$, A, $R^3$ and $R_a{}^3$ are each as defined above.

In this process, the object compound (Ij) or the salt thereof can be prepared by reacting the compound (Ii) or the salt thereof or the reactive derivative at the phosphono group thereof with an esterifying agent. Suitable examples of the salts of the compounds (Ij) and (Ii) are the same as those illustrated hereinabove for the salt of the compound (I).

It is to be understood that preferred examples of the groups as defined for $R_a{}^1$, $R^2$, and A of the Compound (Ii) are the same as those illustrated hereinbefore.

Preferred example of reactive derivative of the compound (Ii) may include an acid halide, an acid anhydride, an activated amide, an activated ester and the like.

The esterifying agent to be used in this process may include an alcohol such as an lower alkanol (e.g. methanol, ethanol, propanol, isopropanol, butanol, pentanol, hexanol, etc.), an ar(lower)alkanol (e.g. benzylalcohol, phenethylalcohol, diphenylmethylalcohol, etc.), an arenol (e.g. phenol, cresol, p-chlorophenol, etc.), etc. and the reactive derivative thereof, and a silyl compound such as trialkylhalosilane, dialkyldihalosilane, alkyltrihalosilane, dialkylarylhalosilane, triarylhalosilane, dialkylaralkylhalosilane, dialkoxydihalosilane, trialkoxyhalosilane, and the like.

As the reactive derivative of said lower alkanol, ar(-lower) alkanol and arenol, there may be exemplified the corresponding halide (e.g. chloride, bromide, iodide), diazocompound (e.g. diazoalkane, diazoaralkane), sulfonate (e.g. alkanesulfonate, arenesulfonate), sulfate or salt with an alkali metal or alkaline earth metal (e.g. lithium, sodium potassium, magnesium, etc.), and the like. More particularly, the preferred examples thereof may be: a halide such as an alkyl halide (e.g. methyl iodide, ethyl bromide, isopropyl bromide, butyl bromide, hexyl chloride, etc.) or an aralkyl halide (e.g. benzyl chloride, phenethyl bromide, diphenylmethyl chloride, etc.); a sulfonate such as an alkyl alkanesulfonate or alkyl arene sulfonate (e.g. methyl methanesulfonate, ethyl p-toluenesulfonate, propyl p-toluenesulfonate, hexyl p-toluenesulfonate, etc.) or an aralkyl alkanesulfonate or aralkyl arenesulfonate (e.g. benzyl p-toluenesulfonate, tolyl methanesulfonate, etc.); a sulfate such as dialkylsulfate (e.g. dimethylsulfate, diethylsulfate, etc.); and the like.

The reaction is usually conducted in a solvent such as methanol, ethanol, propanol, isopropanol, ether, tetrahydrofuran, ethyl acetate, benzene, toluene, dimethylsulfoxide, N-N-dimethylformamide, etc.

The reaction of this process can also be conducted in the presence of an organic or inorganic base. Preferred examples of such base are the same as those given in the explanation for N-Acylation process, II (3).

In case of the reaction of free phosphonic acid (Ii) or the salt thereof with an alcohol such as alkanol, ar(-lower)alkanol or arenol as illustrated above, the reaction can preferably be conducted in the presence of a condensing agent. Preferred examples of such condensating agent may include those given in the explanation for N-Acylation process, II (3), and further, trichloroacetonitrile, p-toluenesulfonyl chloride, isopropylbenzenesulfonyl chloride, pivaloyl chloride, α-bromcyanoacetamide and the like.

The reaction of this process is usually conducted within the range of cooling to ambient temperature.

The object compound (Ij) can be isolated and purified in a conventional manner as explained hereinabove.

(6) Formation of C-S bond

The reaction of this process can be illustrated by the following scheme:

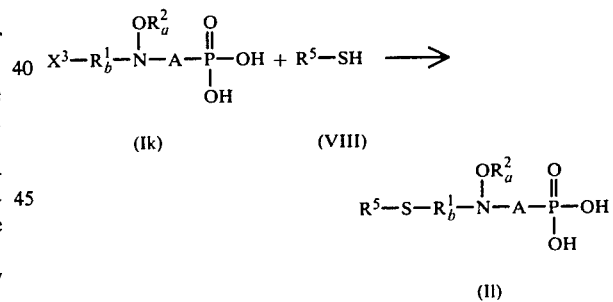

(Ik)        (VIII)

(Il)

wherein $R_a{}^2$ and A are each as defined above, $R_b{}^1$, is 1-oxoalkylene, $R^5$ is alkyl and $X^3$ is an acid residue.

In this process, the object compound (Il) or the salt thereof can be prepared by reacting the compond (Ik) or the salt thereof with the compound (VIII). Suitable examples of the salts of the compounds (Il) and (Ik) are the same as illustrated hereinabove for the salt of the compound (I).

Preferred examples of the acid residue for $X^3$ of the compound (Ik) are the same as those illustrated for $X^1$ in the process I (1).

Preferred examples of 1-oxoalkylene for $R_b{}^1$ of the compound (Ik) may include oxomethylene, 1-oxoethylene, 1-oxopropylene, 1-oxo-trimethylene, 1-oxo-tetramethylene,1-oxo-2-isopropylethylene, and the like.

Preferred examples of alkyl for $R^5$ of the compound (VIII) may include methyl, ethyl, propyl, isopropyl, butyl, isobutyl, tert-butyl, pentyl, hexyl and the like, which may have one or more suitable substituent (s) such as amino, carboxy and the like.

The reaction of this process is usually conducted in a conventional solvent such as alcohol (e.g. methanol, ethanol, propanol, etc.), benzene, toluene, pridine, dimethylsulfoxide, N,N-dimethylformamide and the like. The reaction is preferably conducted within the range of ambient temperature to heating.

The reaction can preferably be conducted in the presence of an organic or inorganic base. Preferred examples of such a base are the same as those given in the explanation for N-Acylation process II (3).

The object compound (II) or the salt thereof can be isolated and purified in a conventional manner as explained hereinabove.

According to the foregoing description of the invention, as to the compounds per se to be protected by the product claim of this application, it is to be noted that the following compounds are to be excluded from the scope of the compounds of the formula (I).

Antibiotic FR-900098, i.e. the compound (I), in which $R^1$ is acetyl, $R^2$ is hydrogen and A is trimethylene, and the pharmaceutically acceptable salt.

Antibiotic FR-33289, i.e. the compound (I), in which $R^1$ is acetyl, $R^2$ is hydrogen and A is 2-hydroxytrimethylene and the pharmaceutically acceptable salt.

Accordingly, it is to be understood that the compounds per se to be protected by this application are substantially directed to the compounds of the formula (I), excepting the antibiotic FR-900098, i.e. "3-(N-acetyl-N-hydroxyamino)propylphosphonic acid" and the pharmaceutically acceptable salt thereof and the antibiotic Fr-33289, i.e. "3-(N-acetyl-N-hydroxyamino)-2-hydroxypropylphosphonic acid" and the pharmaceutically acceptable thereof.

Further, the scope of the compounds per se to be protected by this application may be also represented by an alternative expression as follows.

The compounds of the formula:

$$R^1-N-A-P\overset{O}{\underset{OH}{\diagdown}}\overset{OH}{\diagup}\quad\text{(I)}$$
$$\overset{|}{OR^2}$$

wherein
$R^1$ is hydrogen or acyl,
$R^2$ is hydrogen, lower alkyl, ar(lower)alkyl or acyl, and
A is lower alkylene, lower alkenylene or hydroxy(lower)alkylene, or the ester at the phosphono group thereof or the pharmaceutically acceptable salt thereof, provided that when $R^2$ is hydrogen and A is trimethylene or 2-hydroxytrimethylene, $R^1$ is not acetyl.

Biological Property of Hydroxyaminohydrocarbonphosphonic Acid Derivatives

Antimicrobial activity

The object compound, hydroxyaminohydrocarbonphosphonic acid derivatives (I) and esters at the phosphono group thereof and salts thereof, may possess strong antibacterial activity against pachogenic microorganisms such as Gram positive and negative bacteria, including the genera *Bacillus, Sarcina, Escherichia, Proteus, Salmonella, Pseudomonas, Shigella* and *Enterobacter*. Accordingly, the object compound of this invention is useful for the treatment of infectious disease caused by such pathogenic bacteria in human beings or animals. For illustrating purpose, the biological properties of some representative compounds of the object compound (I) are illustrated in the followings.

1. Monoammonium salt of 3-(N-formyl-N-hydroxyamino)propylphosphonic acid:

Minimum Inhibitory Concentration (M.I.C.)

M.I.C. test was conducted by the usual serial agar dilution method, (inoculum:$10^6$ cells/ml.), using a nutrient agar which was incubated at 37° C. for 20 hours. M.I.C. value is expressed as the minimum concentration of the monoammonium salt of 3-(N-formyl-N-hydroxyamino)propylphosphonic acid (mcg/ml.) which inhibits growth of microorganisms. The results are as follows:

| Test Microorganisms | M.I.C. (mcg/ml.) |
|---|---|
| *Staphylococcus aureus* FDA209P JC-1 | >800 |
| *Bacillus substilis* ATCC6633 | 6.25 |
| *Sarcina lutea* PCI 1001 | ≦0.1 |
| *Escherichia coli* NIHJ JC-2 | 200 |
| *Escherichia coli* 1341-18(R) | 12.5 |
| *Klebsiella pneumoniae* NCTC 418 | 100 |
| *Proteus vulgaris* IAM 1025 | 3.13 |
| *Proteus mirabilis* 1432-75 | 6.25 |
| *Proteus morganii* 1433-2 | >800 |
| *Proteus rettgeri* 1434-3 | 1.56 |
| *Proteus inconstans* 1436-21 | 3.13 |
| *Pseudomonas aeruginosa* IAM 1095 | 0.78 |
| *Salmonella enteritidis* 1891 | 0.39 |
| *Salmonella typhi* 0-901 | 0.39 |
| *Salmonella paratyphi* A-1015 | 12.5 |
| *Salmonella typhimurium* 1406 | 25 |
| *Shigella flexneri* IaEW8 | 12.5 |
| *Shigella sonnei* I EW33 | 100 |
| *Serratia marcescens* 1421-4 | 100 |
| *Citrobacter freundii* 1381-3 | 3.13 |
| *Enterobacter aerogenes* 1402-10 | 6.25 |
| *Enterobacter cloacae* 1401-4 | 6.25 |

Protecting Effect in Experimental Mice Infections:

(a) Test compound

Monoammonium salt of 3-(N-formyl-N-hydroxyamino)propylphosphonic acid (b) Test animal Male mice of ICR-strain, aged 4 weeks and weighing 24±1 g., were used. Each experimental group consists of 8 animals.

(c) Test method

A prescribed amount of pathogenic bacteria, suspended in 5% aqueous Mucin solution (0.5 ml.), was intraperitoneally injected into the test animals.

Subsequently, the above test compound in water (0.25 ml.) was administered to each of the test animals, subcutaneously three times at 0, 1, 3 hours or orally once at 1 hour after the infection of pathogenic bacteria, respectively.

All test animals were observed for survival or death for 1 week and $ED_{50}$ values were calculated by the probit method. The results are shown in the following table.

Table

| Pathogenic bacteria | Inoculated viable cells per mouse | $ED_{50}$ (mg/mouse) | |
|---|---|---|---|
| | | subcutaneous administration | oral administration |
| *Pseudomonas* | | | |

Table-continued

| Pathogenic bacteria | Inoculated viable cells per mouse | ED$_{50}$ (mg/mouse) subcutaneous administration | oral administration |
|---|---|---|---|
| aeruginosa 1101-76 | 1.2 × 10$^6$ | 0.228 | 0.280 |
| Eschericha coli 1341-67 | 6.9 × 10$^7$ | 0.167 | 2.559 |
| Proteus mirabilis 1432-75 | 8.0 × 10$^7$ | 0.236 | 4.331 |

Acute Toxicity (a) Test compound
Monosodium salt of 3-(N-formyl-N-hydroxyamino)-propylphosphonic acid.
(b) Test animal
Male and Female mice of ICR-strain, aged 6 weeks were used.
(c) Observation times
One week
(d) Calculation method
Litchfield-Wilcoxon method

| Animal | Sex | LD$_{50}$ (mg/kg.) oral administration | subcutaneous administration |
|---|---|---|---|
| Mouse | male | >11,000 | 8,050 |
|  | female | >11,000 | 8,270 |
| Rat | male | >11,000 | 8,000 |

2. Monopotassium salt of 3-(N-formyl-N-hydroxyamino)-trans-1-propenylphosphonic acid Minimum Inhibitory Concentration (M.I.C.)

M.I.C. test was conducted by an usual serial agar dilution method, (inoculum: 10$^5$ cells/ml.), using a nutrient agar which was incubated at 37° C. for 18 hours. M.I.C. value is expressed as the minimum concentration of the monopotassium salt of 3-(N-formyl-N-hydroxyamino)-trans-1-propenylphosphonic acid (mcg/ml.) which inhibits growth of microorganisms. The results are as follows:

| Test Microorganisms | M.I.C. (mcg/ml) |
|---|---|
| Staphylococcus aureus FDA209PJC-1 | >100 |
| Bacillus subtilis ATCC6633 | 6.25 |
| Sarcina lutea PCI 1001 | 0.2 |
| Escherichia coli 1341-18(R+) | 25 |
| Klebsiella pneumoniae NCTC 418 | 100 |
| Proteus vulgaris IAM 1025 | 1.56 |
| Proteus mirabilis 1432-75 | 0.39 |
| Proteus morganii 1433-2 | >100 |
| Proteus rettgeri 1434-3 | 6.25 |
| Proteus inconstans 1436-21 | 25 |
| Pseudomonas aeruginosa IAM 1095 | 1.56 |
| Salmonella enteritidis 1891 | 6.25 |
| Salmonella typhi 0-901 | 0.78 |
| Salmonella paratyphi A-1015 | 25 |
| Salmonella typhimurium 1406 | 12.5 |
| Shigella flexneri IaEW8 | 50 |
| Shigella sonnei I EW33 | 25 |
| Serratia marcenscens 1421-4 | >100 |
| Citrobacter freundii 1381-3 | 12.5 |
| Enterobacter aerogenes 1402-10 | 50 |
| Enterobacter cloacae 1401-4 | 12.5 |

According to the foregoing description, it is clear that the compound (I) has an effective antimicrobial activity against pathogenic microorganisms. Particularly, it is to be noted that the compound (I) per se, in which R$^1$ is acyl and R$^2$ is hydrogen and A is as defined above, and the pharmaceutically acceptable salt thereof substantially possess antimicrobial activity against pathogenic microorganisms, while the compound (I), in which R$^1$ is hydrogen and R$^2$ and A are as defined above, the compound (I), in which R$^2$ is lower alkyl, ar(lower)alkyl or acyl and R$^1$ and A are as defined above, and the ester of the phosphono group of the compound (I) wherein R$^1$, R$^2$ and A are as defined above also may possess an antimicrobial activity against pathogenic microorganisms and are further useful as an intermediate for preparing the compound (I), in which R$^1$ is acyl, R$^2$ is hydrogen and A is as defined above, and the pharmaceutically acceptable salt thereof.

The Pharmaceutical Composition Comprising Hydroxyaminohydrocarbonphosphonic Acid Derivatives The object compound (I) of this invention, hydroxyaminohydrocarbonphosphonic acid derivatives and the ester at the phosphono group thereof and pharmaceutically acceptable salt thereof according to this invention, can be formulated for administration in any convenient way, analogously with known antibiotics, in admixture with a non-toxic pharmaceutically acceptable carrier.

A pharmaceutically acceptable salt of the compound (I) may include salt with an inorganic or organic base such as sodium salt, potassium salt, calcium salt, ammonium salt, ethanolamine salt, triethylamine salt, dicyclohexylamine salt and the like, and salt with an inorganic or organic acid such as hydrochloride, sulfate, citrate, maleate, fumarate, tartarate, p-toluenesulfonate and the like, and further salt with an amino acid such as arginine salt, aspartic acid salt, glutanic acid salt, and the like.

Thus, the antimicrobial composition can be used in the form of pharmaceutical preparation, for example, in solid, semisolid or liquid form, which contains an active object compound in admixture with a pharmaceutical organic or inorganic carrier or excipient suitable for external, enteral or parenteral applications. The active ingredient may be compounded, for example, with usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, karatin, colloidal silica, potato starch, urea and other carriers suitable for use in manufacturing preparations, in solid, semisolid, or liquid form, and in addition auxiliary, stabilizing, thickening and coloring agents and perfumes. The antimicrobial compositions can also contain preserving or bacteriostatic agents thereby keeping the active ingredient in the desired preparations stable in activity. The active object compound is included in the antimicrobial composition in an amount sufficient to produce the desired therapeutic effect upon the bacterially infected process or condition.

For applying this composition to human, it is preferably to apply in a form of intravenous, intramuscular or oral administration. While the dosage or therapeutically effective amount of the object compound of this invention varies from and also depends upon the age and condition of each individual patient to be treated, a daily dose of about 2-100 mg. of the active ingredient/kg. of a human being or an animal is generally given for treating diseases, and an average single dose of about 50 mg., 100 mg., 250 mg. and 500 mg. is generally administered.

Preparation of starting compounds

Starting compounds to be used in the preparation of the object compound (I) of this invention and the esters, and salts thereof, can be prepared by following processes:

1. Preparation of the starting compound (II)
   (1) Formation of C—N bond
2. Preparation of the starting compound (IV)
   (1) Formation of C—P bond
   (4) Halogenation (II)
   (2) Halogenation (I)
   (3) Dehydrohalogenation
   (4) Halogenation (II)
3. Preparation of the starting compound (V)
   (1) O-Aralkylation
   (2) Acylation
4. Preparation of the starting compound (VII)
   (1) Formation of C—N bond Each of these processes will be illustrated hereinafter.

1. Preparation of the starting compound (II)
   (1) Formation of C—N bond

The reaction of this process can be illustrated by the following scheme:

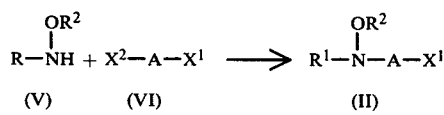

(V)    (VI)    (II)

wherein $R^1$, $R^2$, $X^1$, $X^2$ and A are each as defined above.

In this process, the compound (II) can be prepared by reacting the compound (V) with the compound (VI).

Starting materials (V) include known and novel ones. The known compounds, e.g. N-benzyloxy-p-toluenesulfonamide, are prepared by the method described in Bulletin of the Chemical Society of Japan Vol. 45, page 1462 (1972) and the other new compounds can also be prepared in the similar manner thereto.

The reaction of this process is usually conducted in a solvent such as methanol, ethanol, propanol, benzene, toluene, pyridine, dimethylsulfoxide, N,N-dimethylformamide, etc. and usually at ambient temperature or under heating.

The reaction of this process can preferably be conducted in the presence of an organic or inorganic base, preferred examples of which are the same as those given in explanation of the process I (1) for production of the object compound (I).

The reaction product can be purified and isolated in a conventional manner.

2. Preparation of the starting compound (IV)
   (1) Formation of C—P bond

The reaction of this process can be illustrated by the following scheme:

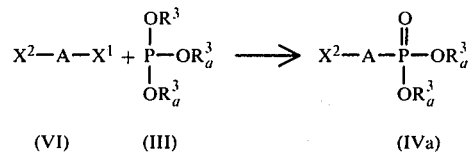

(VI)    (III)    (IVa)

wherein $R^3$, $R_a^3$, $X^1$, $X^2$ and A are each as defined above.

In this process, the compound (IVa) can be prepared by reacting the compound (VI) with the compound (III).

The reaction may be conducted in a solvent or without solvent. Preferred examples of the solvent may include methanol, ethanol, propanol, benzene, toluene, hexane, pyridine, dimethylsulfoxide, N,N-dimethylformamide, etc.

The reaction is usually conducted at ambient temperature or under heating.

The reaction can be preferably conducted in the presence of an organic or inorganic base, preferred example of which are the same as those given in the explanation of the process I (1) for production of the object compound (I)

Optimum reaction conditions can be selected from the above reaction conditions according to kinds of starting compounds, solvent and/or base to be used.

The reaction product can be isolated and purified in a conventional manner.

(2) Halogenation

The reaction of this process can be illustrated by the following scheme:

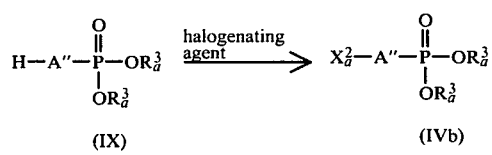

(IX)    (IVb)

wherein $R_a^3$ is as defined above, $X_a^2$ is halogen and A" is alkenylene.

In this process, the compound (IVb) can be prepared by reacting the compound (IX) with a halogenating agent.

The starting material (IX) includes known and novel ones. The known compounds, e.g. diethyl 1-propenylphosphonic acid can be prepared by the method described in Journal of General Chemistry of The USSR Vol. 33, page 429(1963) and the other new compounds can also be prepared in the similar manner thereto.

The halogenating agent to be used in this reaction may include halogen (e.g. chlorine, bromine, etc.), N-haloimide (e.g. N-bromosuccinimide, N-chlorosuccinimide, N-bromophtalimide, etc.), alkyl hypohalite (e.g. t-butyl hypochlorite, amyl hypochlorite, etc.), hypohalogenous acid or its salt (e.g. hypochlorous acid, hypobromous acid, sodium hypochlorite, etc.), sulfuryl chloride, trichloromethanesulfuryl chloride and the like.

This halogenation usually results at so-called allylic position and is conducted in a conventional manner and preferably conducted in the presence of free-radical initiators such as light (e.g. ultra violet, etc.), peroxide (e.g. dibenzoyl peroxide, di-t-butyl peroxide, etc.), azo compound (e.g. azobisisobutyronitrile, etc.) and the like.

The reaction of this process is usually conducted in a solvent such as benzene, cyclohexane and the like, at ambient temperature to around at boiling point of the solvent to be used.

The reaction product (IVb) can be isolated and purified in a conventional manner.

(3) Dehydrohalogenation

The reaction of this process can be illustrated by the following scheme:

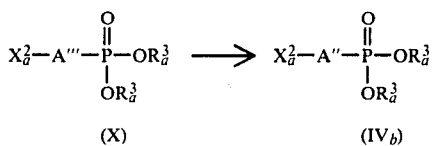

wherein $X_a^2$, $R_a^3$ and $A''$ are each as defined above and $A'''$ is haloalkylene.

The haloalkylene for $A'''$ means an alkylene group bearing a halogen (e.g. chlorine, bromine, iodine, etc.)

In this process, the compound (IVb) can be prepared by subjecting the compound (X) to so-called 1,2-dehydrohalogenation reaction.

The starting material (X) includes known and novel ones. The known compounds, e.g. diethyl 2,3-dibromopropylphosphonate can be prepared by the method described in Zhurnal Obshchei Khimii, Vol. 22 page 1052 (1952), and the other new compounds can also be prepared in the similar manner thereto.

This reaction is conducted in a conventional manner and preferably conducted in the presence of an inorganic or organic base, preferred examples of which are the same as those given in the explanation of the process I (1) for production of the object compound (I).

This dehydrohalogenation is usually conducted in a conventional solvent such as methanol, ethanol, propanol, isopropyl alcohol, tert-butyl alcohol, acetone, chloroform, dichloromethane, ether and the like, and preferably conducted at the temperature from cooling to heating.

The reaction product (IVb) can be isolated and purified in a conventional manner.

(4) Halogenation (II)

The reaction of this process can be illustrated by the following scheme:

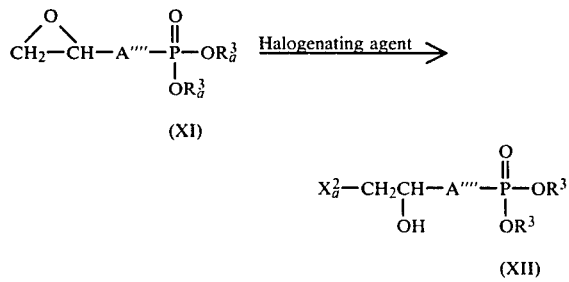

wherein $X^2$, $R^3$ and $R_a^3$ are each as defined above, and $A''''$ is alkylene.

In this process, the compound (XII) can be prepared by reacting the compound (XI) with a halogenating agent.

The starting material (XI) includes known and novel ones. The known compounds, e.g. diethyl 2,3-epoxypropylphosphonate can be prepared by the method described in Journal of the American Chemical Society, Vol. 77, page 6225 (1955), and the other new compounds can also be prepared in the similar manner thereto as described particularly hereinafter.

The halogenating agent to be used in this reaction may include hydrogen halide, a halosilyl compound such as trialkylhalosilane, dialkyldihalosilane, alkyltrihalosilane, dialkylarylhalosilane, triarylhalosilane, dialkylaralkylhalosilane, dialkoxydihalosilane, trialkoxyhalosilane, and the like.

The reaction of this process is preferably conducted in the presence of or absence of solvents such as dichloromethane, chloroform, carbon tetrachloride, benzene, toluene and the like, at ice-cooling to boiling point of the solvent to be used.

The reaction product (XII) can be isolated and purified in a conventional manner.

Moreover, when the reaction product (XII) is used as a starting compound of a further reaction, the hydroxy group of the compound (XII) can be protected with a easily removable group such as tetrahydropyranyl in a conventional manner as described particularly hereinafter.

3. Preparation of the starting compound (V)

(1) O-Aralkylation

The reaction of this process can be illustrated by the following scheme:

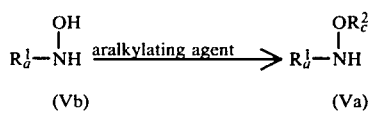

wherein $R_a^1$ is as defined above and $R_c^2$ is aralkyl.

In this process, the compound (Va) can be prepared by reacting the compound (Vb) with an aralkylating agent.

Preferred examples of the aralkylating agent may include an aralkyl halide such as benzyl chloride, benzyl bromide, p-methoxybenzyl bromide, phenethyl iodide, benzhydryl chloride, trityl chloride, etc.; an aralkyl sulfonate such as aralkyl alkanesulfonate (e.g. benzyl methanesulfonate, phenethyl ethanesulfonate, etc.) or aralkyl arenesulfonate (e.g. benzyl p-toluenesulfonate, p-methoxybenzyl p-bromobenzenesulfonate, benzhydryl p-toluenesulfonate, etc.); and diaralkyl sulfate (e.g. dibenzylsulfate, etc.) and the like.

The reaction of this process is usually conducted in a solvent, such as methanol, ethanol, propanol, isopropanol, acetone, dioxane, tetrahydrofuran, N,N-dimethylformamide, ether, benzene, toluene, n-hexane and the like, and usually at around ambient temperature or under cooling.

The reaction can also be conducted in the presence of an organic or inorganic base, preferred examples of which are the same as those given in the explanation of the process I(1) for production of the object compound (I).

The reaction product (Va) can be isolated and purified in a conventional manner.

(2) Acylation

The reaction of this process can be illustrated by the following scheme:

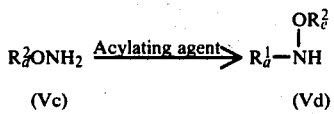

wherein $R_d^2$ is hydrogen or aralkyl, $R_e^2$ is acyl or aralkyl and $R_a^1$ is as defined above.

In this process, the compound (Vd) can be prepared by reacting the compound (Vc) with an acylating agent.

The acylating agent to be used in this reaction are the same as those given in the explanation of N-acylation for the production of the object compound (I).

Further, the reaction conditions (e.g. reaction temperature, solvent, base, condensing agent, etc), and purification and isolation of the reaction product (Vd) are the same as those given in the explanation of N-acylation for the production of the object compound (I).

In the acyaltion process, it is to be understood that there may be produced N-monoacyl, N,O-diacyl derivative or their mixture according to an amount of an acylating agent to be used in this reaction.

That is, the compound (Vc) wherein $R_d^2$ is hydrogen, is acylated with an acylating agent in an amount of one molar equivalent to provide mainly N-monoacyl derivative thereof and with nearly two moles of an acylating agent to provide mainly N,O-diacyl derivative thereof. In the case of the production of a mixture of N-monoacyl and N,O-diacyl derivatives in this reaction, each of the acyl derivatives can be purified and isolated from the reaction mixture in a conventional manner.

4. Preparation of the starting compound (VII)

The reaction of this process can be illustrated by the following scheme:

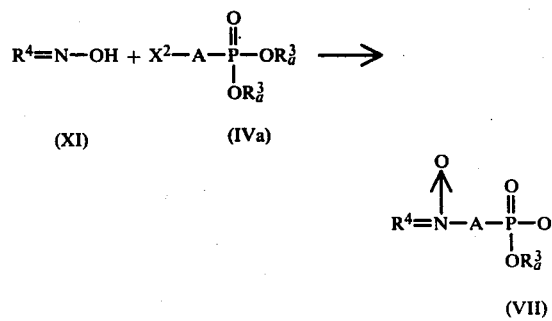

wherein $R_a^3$, $R^4$, $X^2$ and A are each as defined above.

In this process, the compound (VII) can be prepared by reacting the compound (XI) with the compound (IVa).

One of the starting compounds (XI) can be prepared, for example by reacting the corresponding carbonyl compound with hydroxylamine in a conventional manner.

The reaction of this process is usually conducted in a solvent such as methanol, ethanol, propanol, benzene, toluene, pridine, dimethylsulfoxide, N,N-dimethylformamide and the like, at ambient temperature or under slightly warming.

The reaction of this process can preferably be conducted in the presence of an organic or inorganic base, preferred examples of which are the same as those given in the explanation of the process I (1) for production of the object compound (I).

The reaction product can be isolated and purified in a conventional manner.

Suitable examples of some preparations of compound (II) are illustrated more specifically as follows.

(1) N-(p-methoxybenzyloxy)-p-toluenesulfonamide (61.4 g) was added to a solution of sodium ethoxide in absolute ethanol (Na:4.6 g, absolute $C_2H_5OH$:540 ml) and stirred at 70° C. for 1.5 hours. After cooling at ambient temperature, 1,3-dibromopropane (121.2 g) was added to the mixture, and then the mixture was refluxed with stirring for 2 hours and filtered. The filtrate was concentrated under reduced pressure. To the residue was added a mixture of ethyl acetate and water, and the organic layer was separated, dried over magnesium sulfate and evaporated to dryness under reduced pressure to give an oil, which was crystallized from a mixture of ethyl acetate and n-hexane to give N-(3-bromopropyl)-N-(p-methoxybenzyloxy)-p-toluenesulfonamide (75.1 g).

MP:89.5~°91.5° C.

In substantially the same manner as described in the above example, there were obtained the following compounds.

(2) Starting material

Isobutyl N-(p-methoxybenzyloxy)carbamate (19.75 g)

1,3-dibromopropane (47.1 g)

Object compound

Isobutyl N-(3-bromopropyl)-N-(p-methoxyvbenzyloxy)carbamate (17.48 g) in the form of oily substance.

Infrared Absorption Spectrum (liquid film): $\nu_{max}$: 1720(shoulder), 1705, 1610, 1590 cm$^{-1}$

| NMR Absorption Spectrum (CDCl$_3$): |
| --- |
| δ(ppm) |
| 0.95 (6H, d, J=7Hz) |
| 1.8~2.4 (2H, m) |
| 3.35 (2H, t, J=6Hz) |
| 3.55 (2H, t, J=6Hz) |
| 3.74 (3H, s) |
| 3.94 (2H, d, J=6Hz) |
| 4.77 (2H, s) |
| 6.86 (2H, d, J=9Hz) |
| 7.30 (2H, d, J=9Hz) |

(3) Starting material

N-(p-methoxybenzyloxy)-p-toluenesulfonamide (18.4 g)

1-Bromo-3-chloropropane (14.2 g)

Object compound

N-(3-Chloropropyl)-N-(p-methoxylbenzyloxy)-p-toluenesulfonamide (20 g) in the form of crystals.

MP:84~°86° C.

(4) Starting material

N-benzyloxy-p-toluenesulfonamide (27.7 g)

1-Bromo-3-chloropropane (23.6 g)

Object compound

N-(3-chloropropyl)-N-benzyloxy-p-toluenesulfonamide (32.65 g)

MP:84~°87° C.

Suitable working examples for some preparations of the compound (IV) are illustrated more specifically as follows:

(i) For formation of C—P bond:

(1) Sodium hydride dispersion (50% in mineral oil, 5.76 g) was washed twice with dry petroleum ether (200 ml) and suspended in dry benzene (400 ml). To this suspension was added dropwise dibutyl phosphonate (19.4 g) under reflux for 35 minutes and the mixture was refluxed for additional 2.5 hours. To the mixture was added 1-bromo-3-chloropropane (23.63 g) and heating was continued for additional 7 hours under reflux with stirring. After cooling, the resultant mixture was washed twice with water (200 ml), dried over magnesium sulfate and concentrated under reduced pressure to give dibutyl 3-chloropropylphosphonate (21.15 g) in the form of oily substance.

Infrared Absorption Spectrum (liquid film): $\nu_{max}$=1270(shoulder), 1240 cm$^{-1}$ NMR absorption spectrum (neat):
Internal standard: tms

| $\delta$(ppm) |
| --- |
| 0.91 (6H, t, J=7Hz) |
| 1.2~2.2 (2H, t, J=6Hz) |
| 3.65 (2H, t, J=6Hz) |
| 3.96 (4H, quartet, J=7Hz) |

(2) A mixture of 1,3-dibromopropane (305 g) and triethylphosphonate (47.5 g) was stirred at 150° C. for 30 minutes. The resultant mixture was concentrated under reduced pressure to give diethyl 3-bromopropylphosphonate (77.7 g) in the form of oily substance.

Infrared Absorption Spectrum (liquid film): $\nu_{max}$=1270, 1240, 1060, 1030, 970 cm$^{-1}$ NMR absorption spectrum (neat):
Internal standard tms

| $\delta$(ppm) |
| --- |
| 1.33 (6H, t, J=7Hz) |
| 4.08 (4H, quintet, J=7Hz) |

(3) 65% Sodium hydride dispersion in mineral oil (16.3 g) was washed twice with dry petroleum ether (150 ml) and suspended in tetrahydrofuran (400 ml). To the suspension was added diethyl phosphonate (55.2 g) at −8−−10° C., whereafter the mixture was stirred at ambient temperature for 1.5 hours. To the mixture was added 1-bromo-3-chloropropane (126.0 g), whereafter the reaction mixture was stirred for 4 hours at ambient temperature. The resultant mixture was mixed with ethanol (50 ml) to give precipitates. The precipitates were filtered off and then the filtrate was concentrated under reduced pressure to remove the solvent. The residue was distilled at 35°-40° C. under reduced pressure (12 mmHg) to remove 1-bromo-3-chloropropane. Subsequently, the residue was redistilled at 110°-120° C. under reduced pressure (4 mmHg) to give oily diethyl 3-chloropropylphosphonate (52.9 g).

I.R. (film) $\nu$max: 1270 (shoulder), 1240, 1160 cm$^{-1}$

NMR: $\delta$ (ppm) in CDCl$_3$; 1.36 (6H, t, J=7Hz), 1.6–2.5 (4H, m), 3.65 (2H, t, J=6Hz), 4.16 (4H, quintet, J=7Hz).

(4) A mixture of 1,5-dibromopentane (500 g.) and triethylphosphite (72.0 g.) was stirred at 160° C. for 40 minutes and then excess 1,5-dibromopentane was distilled off under reduced pressure to give oily diethyl 5-bromopentylphosphonate (129.6 g.).

N.M.R.: $\delta$(ppm) in CDCl$_3$: 1.32 (6H, t, J=7Hz), 1.42–2.05 (8H, m), 3.39 (2H, t, J=7Hz), 4.05 (4H, m).

(5) A mixture of 1-bromo-3-chloro-2-methylpropane (95 g.) and triethyl phosphite (61.4 g.) was heated to reflux for 5.5 hours with stirring and then excess 1-bromo-3-chloro-2-methylpropane was distilled off under reduced pressure to give oily diethyl 3-chloro-2-methylpropylphosphonate (48.3 g.).

N.M.R.: $\delta$(ppm) in CDCl$_3$: 1.18 (3H, d, J=6Hz), 1.31 (6H, t, J=6Hz), 1.48–2.52 (3H, m), 3.58 (2H, d, J=5Hz), 4.12 (4H, m).

(ii) For halogenation:

(1)-1-Di-tert-butyl cis-1-propenylphosphonate (15.0 g.) was added to a solution of potassium tert-butoxide in tert-butyl alcohol (K: 250 mg., tert.-C$_4$H$_9$OH: 150 ml.) and then the mixture was stirred for 6 hours at 55°-60° C. The resultant mixture was concentrated under reduced pressure and the residue was shaken with a mixture of ethyl acetate (400 ml.) and ice-water (100 ml.). The ethyl acetate layer was separated, washed with water (50 ml.), dried over magnesium sulfate and evaporated to dryness under reduced pressure to give oily residue (13.34 g.), which was distilled under reduced pressure to give oily di-tert.-butyl trans-1-propenylphosphonate (12 g.), b.p. 78°-80° C./2mmHg.

I.R. (liquid film): $\nu$max: 1630, 1260, 1170 cm$^{-1}$.

N.M.R.: $\delta$(ppm) in CDCl$_3$: 1.45 (18H, s), 1.80 (3H, m), 5.67 (1H, m), 6.80 (1H, m).

(1)-2 To a solution of di-tert.-butyl trans-1-propenylphosphonate (12.0 g.) in carbon tetrachloride (120 ml.) were added basic aluminum oxide (24.0 g.), N-bromosuccinimide (10.95 g.) and then dibenzoylperoxide (1.4 g.) The mixture was heated to reflux for an hour and then stirred for 30 minutes under ice-cooling. The resultant mixture was filtered and the filtrate was evaporated to dryness under reduced pressure to give oily di-tert.-butyl 3-bromo-trans-1-propenylphosphonate (17.2 g.).

I.R. (liquid film): $\nu$max: 1630, 1260, 1170 cm$^{-1}$.

N.M.R.: $\delta$(ppm) in CDCl$_3$: 1.51 (18H, s), 4.01 (2H, d, J=7Hz), 5.95 (1H, m), 6.77 (1H, m).

(2) To a solution of diethyl trans-1-propenylphosphonate (32.04 g.) in carbon tetrachloride (320 ml.) were added N-bromosuccinimide (41.65 g.) and dibenzoylperoxide (2.8 g.). The reaction mixture was heated to reflux for 1.5 hours and stirred for 30 minutes under ice-cooling. Insoluble materials were removed off by filtration and the filtrate was concentrated under reduced pressure to give an oily residue (63.09 g.), which was subjected to a column chromatography on silicagel and eluted with chloroform. The eluates were evaporated to dryness under reduced pressure to give an oily diethyl 3-bromo-trans-1-propenylphosphonate (27.04 g.).

I.R. (liquid film): $\nu$max: 1630, 1240, 1160 cm$^{-1}$.

N.M.R.: $\delta$(ppm) in CDCl$_3$: 1.32 (6H, t, J=7Hz), 3.9–4.3 (6H, m), 5.93 (1H, m), 6.81 (1H, m).

(3) To a solution of dimethyl cis-1-propenylphosphonate (6.10 g.) in carbon tetrachloride (60 ml.) was added N-bromosuccinimide (7.97 g.). The reaction mixture was heated to reflux for 2 hours and then cooled to ambient temperature to give precipitates, which were filtered off. The filtrates were concentrated under reduced pressure to give an oily residue, which was subjected to a column chromatography on silica gel and eluted with a mixture of chloroform and ethyl acetate (8:2) to give dimethyl 3-bromo trans-1-propenylphosphonic acid (4.94 g.).

I.R. (liquid film): $\nu$max: 1630, 1250, 1190 cm$^{-1}$.

N.M.R.: $\delta$(ppm) in CDCl$_3$: 3.71 (6H, d, J=10Hz), 4.00 (2H, m), 5.88 (1H, m), 6.82 (1H, m).

(iii) For dehydrohalogenation:

(1)-1 To a solution of diethyl allylphosphonate (5.34 g.) in carbon tetrachloride (107 ml.) was added dropwise a solution of bromine (5.04 g.) in carbon tetrachloride (10 ml.) under ice-cooling in the course of 15 minutes. The reaction mixture was stirred at ambient temperature for 2 hours. After washing twice with 5% aqueous thiosulfate solution (100 ml.) and then with water (100 ml.), the resultant mixture was dried over magnesium sulfate and evaporated to dryness under reduced pressure to give oily diethyl 2,3-dibromopropylphosphonate (9.74 g.).

I.R. (liquid film): $\nu$max: 1250 (broad), 1160 cm$^{-1}$.

N.M.R. $\delta$(ppm) in CDCl$_3$: 1.32 (6H, t, J=7Hz), 2.00–3.12 (2H, m), 3.50–4.63 (7H, m).

(1)-2 To a solution of diethyl 2,3-dibromopropylphosphonate (3.34 g.) in tert.-butanol (10 ml.) was added dropwise a solution of potassium tert.-butoxide (K: 430 mg., tert.-C$_4$H$_9$OH: 14 ml.) at ambient temperature in the course of 15 minutes. The reaction mixture was stirred at the same temperature for 30 minutes. The resultant mixture was concentrated under reduced pressure and then the residue was shaken with a mixture of ethyl acetate (50 ml.) and water (30 ml.). The ethyl acetate layer was separated, washed with water (30 ml.), dried over magnesium sulfate and evaporated to dryness under reduced pressure to give an oily mixture of isomeric diethyl 3-bromo-propenylphosphonates (2.13 g.). An aliquot (1.86 g.) of which was fractionated by subjecting to a column chromatography on silica gel (developing solvent: chloroform) in two fractions (i.e. fraction A and fraction B). The fraction A was evaporated to dryness under reduced pressure to give oily diethyl 3-bromo-cis-1-propenylphosphonate (10 mg.). The fraction B was evaporated to dryness under reduced pressure to give oily mixture (1.65 g.) of diethyl 3-bromo-2-propenylphosphonate and diethyl 3-bromo-trans-1-propenylphosphonate (molar ratio: ca 1:1).

The structures of these isomeric products were determined by N.M.R. spectra as follows:

N.M.R.: $\delta$(ppm) in CDCl$_3$ (a) diethyl 3-bromo-cis-1-propenylphosphonate: 1.34 (6H, t, J=7 Hz), 3.9–4.35 (4H, m), 4.47 (2H, m), 5.69 (1H, m), 6.65 (1H, m).

(b) diethyl 3-bromo-2-propenylphosphonate: 1.32 (6H, t, J=7Hz), 2.80 (2H, d, d, J=23 and 7Hz), 3.9–4.25 (4H, m), 6.1–6.5 (2H, m).

(c) diethyl 3-bromo-trans-1-propenylphosphonate: 1.32 (6H, t, J=7Hz), 3.9–4.25 (6H, m), 5.95 (1H, m), 6.80 (1H, m).

(iv) For Halogenation (II)

(1)-(a) 47% Aqueous hydrobromic acid (82.8 g) was added dropwise to diethyl 2,3-epoxypropylphosphonate (77.6 g) under ice-cooling and with stirring over a five minutes interval. After the stirring was continued for an hour under ice-cooling and for 3 hours at ambient temperature, the reaction mixture was extracted with ethyl acetate (500 ml). The ethyl acetate layer was separated, washed three times with saturated aqueous sodium bicarbonate solution (200 ml and 100 ml×2) and twice with saturated aqueous sodium chloride solution (100 ml×2), dried over magnesium sulfate and evaporated to dryness to give oily diethyl 3-bromo-2-hydroxypropylphosphonate (94.7 g)

I.R. (liquid film): $\nu_{max}$: 3350, 1230, 1160 cm$^{-1}$.
N.M.R.: $\delta$(ppm) in CDCl$_3$: 1.33 (6H, t, J=7Hz), 1.90–2.33 (2H, m), 3.49 (2H, d, d, J=1 and 4Hz), 3.88–4.48 (5H, m).

(1)-(b) To a mixture of diethyl 3-bromo-2-hydroxypropylphosphonate (82.5 g) and p-toluenesulfonic acid (1.03 g) was added dropwise 3,4-dihydro-2H-pyrane (250 g) under ice-cooling and with stirring. After the reaction mixture was stirred at the same temperature for 10 minutes and at ambient temperature for 1.5 hours, the dihydropyrane was removed off by evaporation under reduced pressure to give a residue, which was dissolved in ethyl acetate (500 ml). The ethyl acetate solution was washed with saturated aqueous sodium bicarbonate solution (100 ml) and with saturated aqueous sodium chloride solution (100 ml), dried over magnesium sulfate and evaporated to dryness under reduced pressure to give oily diethyl 3-bromo-2-(tetrahydro-2H-pyran-2-yloxy)propylphosphonate (138 g).

I.R. (liquid film): $\nu_{max}$: 1240, 1190 cm$^{-1}$.
N.M.R.: $\delta$(ppm) in CDCl$_3$: 1.42 (6H, t, J=7Hz), 1.75 (6H, m), 200–2.56 (2H, m), 3.45–4.40 (9H, m), 4.86 (1H, m).

(2) To a solution of diethyl 2,3-epoxypropylphosphonate (0.97 g) in dichloromethane (2 ml) was added dropwise trimethylbromesilane (3.06 g) under ice-cooling and with stirring. After the stirring was continued for 30 minutes under ice-cooling and for 1.5 hours at ambient temperature, the reaction mixture was concentrated under reduced pressure to give an oily residue, which was dissolved in water (8 ml) and washed three times with chloroform (5 ml×3). The aqueous layer was separated, adjusted to pH 5 with conc. aqueous ammonia and evaporated to dryness under reduced pressure to give a residue, to which was added ethanol (20 ml). Insoluble materials were removed by filtration. The filtrate was allowed to stand for 3 hours at ambient temperature to precipitate crystals, which were collected by filtration and dried on phosphorus pentoxide to give crystalline monoammonium salt of 3-bromo-2-hydroxypropylphosphonic acid (560 mg).

MP: 119°–124° C. (dec.)

Suitable working examples of some preparations of the starting compound (V) are illustrated more specifically as follows (i) O-Aralkylation (1) A solution of isobutyl N-hydroxycarbamate (40 g) in absolute ethanol (400 ml) was added dropwise to a solution of sodium ethoxide in absolute ethanol (Na: 6.9 g, absolute C$_2$H$_5$OH: 500 ml) at around 25° C., with stirring. To the mixture was added dropwise p-methoxybenzyl bromide (60 g) for 30 minutes with stirring below 30° C. After continuation of stirring at the ambient temperature for additional 14 hours, the solvent was distilled off under reduced pressure. To the oily residue was added water (500 ml), extracted with ethyl ether (500 ml), washed with 0.1N-NaOH, water, dried over magnesium sulfate and evaporated to dryness under reduced pressure to give an oil (62 g). The oil (62 g) was subjected to column chromatography on silica gel with an eluent (a mixture of 100 parts of chloroform and one part of methanol by volume). Fractions containing object compound was collected and concentrated under reduced pressure to give isobutyl N-(p-methoxybenzyloxy)carbamate (20.0 g) in the form of oily substance.

Infrared Absorption Spectrum (liquid film): $\nu_{max}$=3290, 1725 cm$^{-1}$

---

NMR Absorption Spectrum (CDCl$_3$):
Internal standard : TMS
$\delta$(ppm)

0.89 (6H, d, J=7Hz)
1.92 (1H, m)
3.71 (3H, s)

| NMR Absorption Spectrum (CDCl$_3$): |
| --- |
| Internal standard : TMS |
| δ(ppm) |
| 3.88 (2H, d, J=7Hz) |
| 4.74 (2H, s) |
| 6.70~7.40 (4H, m) |
| 7.86 (1H, s) |

(ii) Acylation (1) A solution of tosyl chloride (156.7 g) in pyridine (240 ml) was added dropwise to a solution of p-methoxybenzyloxyamine (102.3 g) in pyridine (210 ml) for 2.5 hours under cooling at 0°~5° C. and the mixture was stirred overnight at ambient temperature. The solvent was distilled off under reduced pressure and the residue was dissolved in ethyl acetate (1 l). The insoluble substances were filtered off, and the filtrate was washed three times with 2N hydrochloric acid, twice with water, dried over magnesium sulfate and evaporated to dryness under reduced pressure to give crystalline product, which was recrystallized from a mixture of ethylacetate and petroleum ether to give N-(p-methoxybenzyloxy)-p-toluenesulfonamide (162.2 g) in the form of crystals.

MP: 109°~111° C.

(2) Hydroxylamine.hydrochloride (312.8 g) was dissolved in a solution of sodium hydroxide (558.0 g) in water (3.6 liters) under ice-cooling and with stirring. To the solution was added dropwise ethyl chloroformate (1025.4 g) over a 1.5 hours interval under ice-cooling and with stirring. After the stirring was continued for additional 15 minutes the reaction mixture was extracted twice with methyl isobutyl ketone (3 liters and 1.5 liters). The extract was washed with water (1.5 liters) and dried over magnesium sulfate, which was removed by filtration and washed with methylisobutylketone (0.9 liters). The washings were combined with the filtrate, as obtained in the above. To the mixture was added dropwise a solution of potassium hydroxide (265.5 g) in ethanol (1.13 liters) to precipitate crystals under ice-cooling (0°-5° C.) and with stirring over a 40 minutes interval. The stirring was continued for half an hour at the same temperature to give crystalline mono potassium salt of ethyl N-ethoxycarbonyloxycarbomate (758.0 g)

MP: 169.5°-170° C. (dec.)

Suitable examples of some preparations of the starting compound (VII) are illustrated more specifically as follows.

(1) Butyraldehyde oxime (4.52 g.) was added to an ethanolic solution of sodium ethoxide [prepared from 1.17 g of sodium and 100 ml. of absolute ethanol] at 5° to 10° C. To the mixture was added diethyl 3-bromopropylphosphonate (12.69 g.) The reaction mixture was stirred at ambient temperature for 22 hours and then evaporated to dryness under reduced pressure. The residue was dissolved in water and washed with ethyl acetate (20 ml.) The aqueous layer was separated, saturated with sodium chloride and extracted five times with chloroform. The combined chloroform extracts were washed with saturated aqueous sodium chloride solution, dried over magnesium sulfate and evaporated to dryness under reduced pressure to give oily diethyl 3-butylideneaminopropylphosphonate-N-oxide (7.1 g.).

N.M.R.: δ(ppm) in CDCl$_3$; 0.98 (3H,t, J=7 Hz), 1.32 (6H,t, J=7 Hz), 1.1-2.6 (8H, m), 3.8-4.3 (6H, m), 6.8 (1H, t, J=7 Hz).

(2) Octanal oxime (20.67 g.) was dissolved in a methanolic solution of sodium methoxide [prepared from 2.3 g of sodium and 100 ml. of absolute methanol] at 5° to 10° C. To the solution was added dropwise diethyl 3-bromopropylphosphonate (25.9 g.), whereafter the reaction mixture was stirred at ambient temperature for 2 hours and then heated to reflux for 2 hours with stirring. The resultant mixture was evaporated to dryness under reduced pressure and the residue was dissolved in water. The aqueous solution was saturated with sodium chloride and extracted with chloroform. The chloroform extracts were dried over magnesium sulfate and evaporated to dryness under reduced pressure to give oily diethyl 3-octylideneaminopropylphosphonate-N-oxide (38.9 g.).

N.M.R.: δ(ppm) in CDCl$_3$; 0.88 (3H, t, J=7 Hz), 1.32 (6H, t, J=7 Hz), 1.2-2.5 (16H, m), 3.8-4.3 (6H, m), 6.80 (1H, t, J=7 Hz).

The following examples are given for illustrating this invention.

EXAMPLES FOR THE FORMATION OF C—P BOND (1) 50% Sodium hydride dispersion in mineral oil (5.7 g) was washed with dry petroleum ether (100 ml) and suspended in dry benzene (400 ml). Dibutyl phosphonate (19.2 g) was added dropwise to the suspension under reflux in the course of 30 minutes and then the mixture was refluxed with stirring for additional 3 hours. To the mixture, there was added dropwise a solution of N-(3-bromopropyl)-N-(p-methoxybenzyloxy)-p-toluenesulfonamide (38.4 g) in dry benzene (140 ml) in the course of 40 minutes under reflux and the reaction mixture was refluxed with stirring for additional 5 hours. The resultant mixture was washed with water, dried over magnesium sulfate and concentrated under reduced pressure to give an oily residue (46 g). The residue was subjected to column chromatography on silica gel with an eluent (a mixture of 20 parts of chloroform and one part of ethyl acetate by volume). The fractions containing the object compound were collected and concentrated under refuxed pressure to give dibutyl 3-[N-(p-methoxybenzyloxy)-N-tosylamino]propylphosphonate (29.5 g) in the form of an oily substance.

Infrared Absorption Spectrum (liquid film):
$v_{max}$ = 1620, 1600, 1370, 1360, 1260, 1170 cm$^{-1}$

| NMR Absorption Spectrum (CDCl$_3$): | |
| --- | --- |
| δ (ppm) | |
| 0.92 | (6H, t, J=7Hz) |
| 1.05~2.00 | (8H, m) |
| 2.37 | (3H, s) |
| 2.94 | (2H, m) |
| 3.78 | (3H, s) |
| 4.02 | (4H, quartet, J=6Hz) |
| 5.04 | (2H, s) |
| 6.89 | (2H, d, J=8Hz) |
| 7.32 | (4H, m) |
| 7.74 | (2H, d, J=8Hz) |

(2) 50% Sodium hydride dispersion in mineral oil (3.87 g) was washed twice with dry petroleum ether (100 ml) and suspended in dry benzene (250 ml). Dibutyl phosphonate (13.2 g) was added dropwise to the suspension in the course of 15 minutes under reflux and then the mixture was refluxed with stirring for additional 3 hours. To the mixture, there was added dropwise a solution of isobutyl N-(p-methoxybenzyloxy)-N-(3-bromopropyl)carbamate (16.6 g) in dry benzene (50 ml) in the course of 35 minutes under reflux and the reaction mixture was refluxed with stirring for additional 8 hours. The resultant mixture was washed with water, dried over magnesium sulfate and then concentrated under reduced pressure to give an oily residue (23.07 g). The residue was subjected to column chromatography on silica gel with an eluent (a mixture of 100 parts of chloroform and one part of methanol by volume). The fractions containing the object compound were collected and concentrated under reduced pressure to give dibutyl 3-[N-isobutoxycarbonyl-N-(p-methoxybenzyloxy)amino]propylphosphonate (15.6 g) in the form of an oily substance.

Infrared Absorption Spectrum (liquid film): $v_{max}$=1720(shoulder), 1710, 1610, 1590, 1255, 1030 cm$^{-1}$ NMR Absorption Spectrum (CDCl$_3$):
| $\delta$(ppm) | |
|---|---|
| 0.95 | (12H, m) |
| 1.2~2.1 | (13H, m) |
| 3.50 | (2H, t, J=6Hz) |
| 3.79 | (3H, s) |
| 3.95~4.23 | (6H, m) |
| 4.78 | (2H, s) |
| 6.90 | (2H, d, J=8Hz) |
| 7.33 | (2H, d, J=8Hz) |

(3) 50% Sodium hydride dispersion in mineral oil (12.2 g) was washed with dry petroleum ether (100 ml) and suspended in dry benzene (600 ml). Dibutyl phosphonate (40.0g) was added dropwise to the suspension in the course of 30 minutes under reflux and then the mixture was refluxed with stirring for additional 3.5 hours. To the reaction mixture, there was added dropwise a solution of N-(3-bromopropyl)-N-benzyloxy-p-toluenesulfonamide (64.1 g) in dry benzene (250 ml) under reflux in the course of an hour, and then the reaction mixture wa refluxed with stirring for additional 5 hours. The resultant mixture was washed with water, dried over magnesium sulfate and concentrated to give an oily residue (77.0 g). The residue was subjected to column chromatography on silica gel with an eluent (chlofororm). The fractions containing the object compound were collected and concentrated under reduced pressure to give dibutyl 3-(N-benzyloxy-N-tosylamino)-propylphosphonate (58.7g) in the form of an oily substance.

NMR Absorption Spectrum (CDCl$_3$) :
| $\delta$(ppm) | |
|---|---|
| 0.92 | (3H, t, J=8Hz) |
| 1.2~2.0 | (16H, s) |
| 2.38 | (3H, s) |
| 2.94 | (2H, t, J=6Hz) |
| 3.99 | (4H, q, J=7Hz) |
| 5.09 | (2H, s) |
| 7.2~7.5 | (7H, m) |
| 7.71 | (2H, d, J=8Hz) |

(4) 50% Sodium hydride dispersion in mineral oil (630 mg) was washed twice with dry petroleum ether (20 ml) and suspended in dry N,N-dimethylformamide (20 ml). Diethyl phosphonate (1.52 g) was added dropwise to the suspension at 80° C. in the course of 5 minutes and then the mixture was stirred at the same temperature for 30 minutes. To the mixture, there was added N-(p-methoxybenzyloxy)-N-(3-chloropropyl)-p-toluenesulfonamide (3.84 g) at 80° C. for 5 minutes and then the reaction mixture was refluxed with stirring for 2.5 hours. The resultant mixture was concentrated under reduced pressure to give an oily residue. To the residue were added water (200 ml) and ethyl acetate (200 ml). The ethyl acetate layer was separated, dried over magnesium sulfate and then concentrated under reduced pressure to give diethyl 3-[N-(p-methoxybenzyloxy)-N-tosylamino]propylphosphonate (3.79 g) in the form of an oily substance.

Infrared Absorption Spectrum (liquid film): $v_{max}$=1610, 1590, 1250 cm$^{-1}$ NMR Absorption Spectrum (CDCl$_3$):
| $\delta$(ppm) | |
|---|---|
| 1.29 | (6H, t, J=7Hz) |
| 1.6~2.0 | (4H, m) |
| 2.34 | (3H, s) |
| 2.90 | (2H, m) |
| 3.75 | (3H, s) |
| 4.06 | (4H, quintet, J=7Hz) |
| 5.00 | (2H, s) |
| 6.85 | (2H, d, J=8Hz) |
| 7.28 | (4H, m) |
| 7.69 | (2H, d, J=8Hz) |

(5) 50% Sodium hydride dispersion in mineral oil (3.53g) was washed twice with dry petroleum ether (50 ml) and suspended in dry N,N-dimethylformamide (60 ml). Diethyl phosphonate (8.47 g) was added dropwise to the suspension at 80° C. in the course of 25 minutes and the mixture was stirred at the same temperature for additional 25 minutes. Subsequently, to the mixture was added N-(3-chloropropyl)-N-benzyloxy-p-toluenesulfonamide (20 g), and then the reaction mixture was refluxed with stirring for 15 minutes. The reaction mixture was cooled until 120° C. and stirred at the same temperature for 2 hours. The resultant mixture was concentrated under reduced pressure to give a residual oil, which was dissolved in water (300 ml). The solution was extracted twice with ethyl acetate (400 ml). The combined ethyl acetate layer was dried over magnesium sulfate and concentrated under reduced pressure to give a residual oil (28.9g). The residual oil was subjected to column chromatography with an eluent (chloroform). Fractions containing the object compound were collected and concentrated under reduced pressure to give diethyl 3-(N-benzyloxy-N-tosylamino)propylphosphonate (25.5 g) in the form of an oily substance.

Infrared Absorption Spectrum (liquid film): $v_{max}$=1590, 1350, 1240 cm$^{-1}$ NMR Absorption Spectrum (CDCl$_3$) :
| $\delta$(ppm) | |
|---|---|
| 1.28 | (6H, t, J=7Hz) |
| 1.6~2.0 | (4H, m) |
| 2.35 | (3H, s) |
| 2.89 | (2H, m) |
| 4.05 | (4H, quintent, J=7Hz) |
| 5.07 | (2H, s) |
| 7.2~7.4 | (7H, m) |
| 7.71 | (2H, d, J=9Hz) |

(6) A mixture of N-benzyloxy-N-(2-bromoethyl)-p-toluenesulfonamide (16.2 g.) and triethyl phosphite (21.0 g.) was stirred at 160° C. for 10 hours and then cooled to ambient temperature. To the reaction mixture was added ethyl acetate and water. The ethyl acetate layer was separated, washed with water, dried over magnesium sulfate and concentrated under reduced pressure to give an oily residue (20.5 g.). A small volume of isopropyl ether was added to the residue to give crystals, which was separated by filtration and dried to give crystalline diethyl 2-(N-benzyloxy-N-tosylamino)ethylphosphonate (10.6 g.). The object compound (2.1 g.) was also recovered from the mother liquor by subjecting to a column chromatography on silicagel (developing solvent: chloroform)

M.p. 78°–80° C.

| N.M.R. | | |
| --- | --- | --- |
| $\delta$(ppm) in CDCl$_3$: | 1.25 | (6H, t, J=7Hz) |
| | 1.85 | (2H, m) |
| | 2.36 | (3H, s) |
| | 3.14 | (2H, m) |
| | 4.01 | (4H, m) |
| | 5.06 | (2H, s) |
| | 7.14 | (5H, s) |
| | 7.38<br>7.80 | (4H, AB$_q$, J$_{AB}$=8Hz) |

EXAMPLE FOR FORMATION OF C—N bond (1) N-(p-methoxybenzyloxy)-p-toluenesulfonamide (9.21 g) was added to a solution of sodium ethoxide in absolute ethanol (Na: 690 mg, absolute C$_2$H$_5$OH: 80 ml) at 70° C. and the mixture was stirred at the same temperature for an hour. To the mixture was added dropwise diethyl 3-bromopropylphosphonate (7.77 g), whereafter the reaction mixture was refluxed with stirring for 6 hours. The resultant mixture was cooled to give precipitates, which was filtered off. The filtrate was concentrated under reduced pressure to give a residue. To the residue, there were added ethyl acetate (100 ml) and water (50 ml). The ethyl acetate layer was separated and washed twice with water (50 ml), dried over magnesium sulfate and then concentrated under reduced pressure to give an oily residue (13.85 g). The residue was subjected to column chromatography on silica gel with an eluent (a mixture of 5 parts of chloroform and one part of methanol by volume). Fractions containing the object compound were collected and concentrated under reduced pressure to give diethyl 3-[N-(p-methoxybenzyloxy)-N-tosylamino]propylphosphonate (10.50 g) in the form of an oily substance.

Infrared Absorption Spectrum (liquid film): $\nu_{max}$=1610, 1600, 1370, 1350, 1255, 1170 cm$^{-1}$

| NMR Absorption Spectrum (CDCl$_3$) : | |
| --- | --- |
| $\delta$(ppm) | |
| 1.28 | (6H, t, J=7Hz) |
| 1.55~2.05 | (4H, m) |
| 2.37 | (3H, s) |
| 2.92 | (2H, t, J=6Hz) |
| 3.76 | (3H, s) |
| 4.07 | (4H, quintet, J=7Hz) |
| 5.01 | (2H, s) |
| 6.85 | (2H, d, J=9Hz) |
| 7.30 | (4H, m) |
| 7.71 | (2H, d, J=9Hz) |

(2) A solution of ethyl N-benzyloxycarbamate (7.80 g.) in absolute ethanol (5 ml.) was added dropwise to a solution of sodium ethoxide in absolute ethanol [Na: 920 mg., absolute C$_2$H$_5$OH: 100 ml.] at 70° C. and the mixture was stirred at the same temperature for 30 minutes. To the mixture was added dropwise dibutyl 3-chloropropylphosphonate (10.8 g.), whereafter the reaction mixture was refluxed with stirring for 22 hours. The resultant mixture was cooled to give precipitates, which were filtered off. The filtrate was concentrated under reduced pressure to give a residue. To the residue was added ethyl acetate (100 ml.) and water (50 ml.). The ethyl acetate layer was separated, dried over magnesium sulfate and then concentrated under reduced pressure to give an oily residue (16.6 g.). The residue was subjected to column chromatography on silica gel with an eluent (chloroform). Fractions containing the object compound were collected and concentrated under reduced pressure to give oily dibutyl 3-(N-benzyloxy-N-ethoxycarbonylamino)propylphosphonate (7.33 g.)

I.R. (film)$\nu$max: 1700, 1380, 1270, 1240, 1170 cm$^{-1}$

| N. M. R.: $\delta$(ppm) in CDCl$_3$ : | |
| --- | --- |
| 0.90 | (6H, t, J=7Hz) |
| 1.2–2.1 | (15H, m) |
| 3.52 | (2H, t, J=6Hz) |
| 3.99 | (4H, quartet, J=7Hz) |
| 4.20 | (2H, quartet, J=7Hz) |
| 4.83 | (2H, s) |
| 7.34 | (5H, m) |

(3) 50% Sodium hydride dispersion in mineral oil (580 mg.) was washed with dry petroleum ether (10 ml.) and suspended in dry N-N-dimethylformamide (20 ml.). To the suspension was added N-benzyloxy-p-toluenesulfonamide (2.77 g.) at 70° C., whereafter the mixture was stirred at 70° C. for 30 minutes. To the mixture, there was added dibutyl 3-chloropropylphosphonate (2.71 g.) at 74° C., whereafter the reaction mixture was stirred at 100° C. for 30 minutes and refluxed with stirring for 1.5 hours. The reaction mixture was concentrated under reduced pressure. The oily residue was diluted with ethyl acetate and water. Ethyl acetate layer was separate. The aqueous layer was extracted with ethyl acetate. The combined ethyl acetate layer was dried over magnesium sulfate and concentrated under reduced pressure to give oily dibutyl 3-(N-benzyloxy-N-tosylamino)propylphosphonate (3.12 g.).

I.R. (film)$\nu$max: 1600, 1250, 1170 cm$^{-1}$

| N.M.R.: $\delta$(ppm) in CDCl$_3$: | |
| --- | --- |
| 0.91 | (6H, t, J=7Hz) |
| 1.0–2.0 | (12H, m) |
| 2.38 | (3H, s) |
| 2.90 | (2H, m) |
| 4.01 | (4H, quartet, J=7Hz) |
| 5.11 | (2H, s) |
| 7.15–7.50 | (7H, m) |
| 7.74 | (2H, d, J=9Hz) |

(4) 65% Sodium hydride dispersion in mineral oil (810 mg.) was washed twice with dry petroleum ether (50 ml.) and suspended in dry N-N-dimethylformamide (20 ml.). To the suspension was added N-benyloxy-p-toluenesulfonamide (5.54 g.) at ambient temperature, whereafter the mixture was stirred at 40° C. for 15 minutes. To the mixture was added diethyl 3-chloropropylphosphonate (4.27 g.) whereafter the reaction mixture was stirred at 70° C. for 2 hours and at 90° C. for one hour. The resultant mixture was concentrated under reduced pressure. The residue was dissolved in ethyl acetate (80 ml.) and water (30 ml.). The ethyl acetate layer was separated, washed twice with water (20 ml.), dried over magnesium sulfate and concentrated under reduced pressure to give oily diethyl 3-(N-benzyloxy-N-tosylamino)propylphosphonate (8.98 g.).

I.R. (film)νmax: 1590, 1350, 1240 cm⁻¹

N.M.R.: δ(ppm) in CDCl₃:

| | |
|---|---|
| 1.28 | (6H, t, J=7Hz) |
| 1.6–2.0 | (4H, m) |
| 2.35 | (3H, s) |
| 2.89 | (2H, m) |
| 4.05 | (4H, quintet, J=7Hz) |
| 5.07 | (2H, s) |
| 7.2–7.4 | (7H, m) |
| 7.71 | (2H, d, J=9Hz) |

(5) Hydroxylamine hydrochloride (13.9 g.) was dissolved in hot methanol (70 ml.). To this solution was added a solution of sodium methoxide in absolute methanol [Na: 4.6 g., absolute CH₃OH: 70 ml.] over a 15-minutes interval in an atmosphere of nitrogen, whereafter the mixture was stirred at ambient temperature for 30 minutes. The resulting sodium chloride was separated by filtration and washed with methanol (10 ml.). To the combined solution of the filtrate and washings was added 3-bromopropylphosphonic acid (4.06 g.) with stirring in an atmosphere of nitrogen, and the resultant mixture was then concentrated under reduced pressure at ambient temperature over 3 hours interval to give residue (10.4 g.), which was dissolved in water (5 ml.). The solution was passed through a column of anion exchange resin, Amberlite IRA400 (200 ml.) (trade name, maker: Rohm & Haas Co.). After the column was washed with water (1 l), the object compound was eluted with 1 N hydrochloric acid (500 ml.). Fractions containing the object compound was collected and concentrated under reduced pressure to give residue (4.01 g.), which was passed through a column of cation exchange resin, Amberlite IR120B (150 ml.) (trade name, maker: Rohm & Haas Co.). After the column was washed with water (1 l), the object compound was eluted with 1 N hydrochloric acid (500 ml.). Fractions containing the object compound were collected and concentrated under reduced pressure to give residue (2.48 g.), which was dissolved in water (5 ml.). The aqueous solution was adjusted to pH 4 with sodium bicarbonate, whereafter the mixture was allowed to stand overnight to give crystalline 3-(N-hydroxyamino)propylphosphonic acid (1.47 g.)

mp: 151°–154° C. (dec.).

(6) 50% Sodium hydride dispersion in mineral oil (810 mg) was washed with dry petroleum ether (10 ml) and suspended in dry N-N-dimethylformamide (15 ml). To this suspension was added dropwise a solution of methyl N-methoxy carbamate (1.47 g) in N,N-dimethylformamide (3 ml) under ice-cooling. The mixture was stirred at the same temperature for 15 minutes and then at ambient temperature for an hour. To reaction mixture ws added dropwise diethyl 3-bromopropylphosphonate (3.63 g) and the mixture was stirred at ambient temperature for 45 minute and at 60° C. for 45 minutes.

Subsequently, the reaction mixture was concentrated under reduced pressure to give an oily residue, to which was added 3% hydrochloric acid (40 ml). The resultant mixture was extracted five times wit ethyl acetate (50 ml). The combined ethyl acetate layer was dried over magnesium sulfate and concentrated under reduced pressure to give oily diethyl 3-(N-methoxy-N-methoxycarbonylamino)propylphosphonate (4.12 g).

I.R. (liquid film): νmax: 1720, 1450, 1380, 1280, 1230, 1195, 1170, 1100, 1110, 965 cm⁻¹. N.M.R.: δ (ppm) in CDCl₃; 1.30 (6H, t, J=7 Hz), 1.5–2.2 (4 H, m), 3.55 (2H, t, J=6 Hz), 3.62 (3H, s), 3.73 (3H, s), 4.08 (4H, quintet, J=7 Hz).

(7) To a solution of diethyl 3-chloropropylphosphonate (430.6 g) in dry N,N-dimethyformamide (2.25 l) was added potassium salt of ethyl N-ethoxycarbonyloxycarbamate (429.2 g). This mixture was stirred at 64°–66° C. for three hours. After the resulting potassium chloride was removed by filtration, the filtrate was concentrated under reduced pressure. The residue was dissolved in ethyl acetate (2.0 l) and washed with water (4.0 l). The aqueous layer was extracted twice with ethyl acetate (1.2 and 0.8 l). The combined ethyl acetate layer was washed with saturated aqueous sodium chloride solution (1.5 l), dried over magnesium sulfate and concentrated under reduced pressure to give oily diethyl 3-(N-ethoxycarbonyl-N-ethoxycarbonyloxyamino)propylphosphonate (643.7 g).

I.R. (liquid film): νmax: 1780, 1730, 1720 (Sh) cm⁻¹.
N.M.R.: δ(ppm) in CDCl₃; 1.1–1.5 (12H, m), 1.6–2.1 (4H, m), 3.74 (2H, t, J=6Hz), 3.95–4.45 (8H, m).

(8) To a solution of diethyl 5-bromopentyphosphonate (28.7 g.) in dry N,N-dimethylformamide (144 ml.) was added potassium salt of ethyl N-ethoxycarbonyloxycarbamate (21.5 g.). This mixture was stirred at 30° C. for an hour and then poured into ice water (600 ml.). The resultant mixture was extracted twice with ethyl acetate (200 ml. and 100 ml.). The combined ethyl acetate layer was washed four times with water (100 ml.) and dried over magnesium sulfate to give an oily diethyl 5-(N-ethoxycarbonyl-N-ethoxycarbonyloxyamino)pentylphosphonate (36.2 g.).

N.M.R.: δ(ppm) in CDCl₃; 1.14–1.48 (12H, m), 1.08–2.08 (8H, m), 3.64 (2H, t, J=6 Hz), 3.88–4.46 (8H, m).

(9) To a solution of di-tert-butyl 3-bromo-trans-1-propenylphosphonate (17.1 g.) in dry N,N-dimethylformamide (55 ml.) was added potassium salt of ethyl N-ethoxycarbonyloxycarbamate (11.03 g.). The reaction mixture was stirred for 10 minutes under ice-cooling and for 1.5 hours at ambient temperature. The reaction mixture was poured into ice water (400 ml.) and then the resultant mixture was extracted three times with ethyl acetate (300 ml., 200 ml. and 100 ml.). The combined ethyl acetate layer was washed three times with water (100 ml.), dried over magnesium sulfate and then concentrated under reduced pressure to give an oily residue (20.23 g.). The residue was subjected to column chromatography on silica gel (200 g.) [developing solvent: a mixture of chloroform and ethyl acetate (4:1)]. The fractions containing the object compound were collected and concentrated under reduced pressure to give an oily di-tert-butyl 3-(N-ethoxycarbonyl-N-ethoxycarbonyloxyamino)-trans-1-propenylphosphonate (8.84 g.).

I.R. (liquid film): νmax: 1790, 1730 (broad), 1640, 1250 (broad), 1170 cm⁻¹.
N.M.R.: δ(ppm) in CDCl₃: 1.20–1.40 (6H, m), 1.46 (18H, s), 4.10–4.45 (6H, m), 5.92 (1H, m), 6.54 (1H, m).

(10) To a solution of dimethyl 3-bromo-trans-1-propenylphosphonate (5.34 g.) in N,N-dimethylformamide (25 ml.) was added potassium salt of ethyl N-ethoxy-carbonyloxycarbamate (5.01 g.). After the reaction mixture was stirred for 10 minutes under ice-cooling and for 50 minutes at ambient temperature, the mixture was poured into ice water (250 ml.). The resultant mixture was extracted three times with ethyl acetate (200 ml. and 100 ml.×2). The combined ethyl acetate layer was washed with water (100 ml.), dried over magnesium sulfate and then concentrated under reduced pressure to give an oily residue (4.72 g.). The residue was subjected to a column chromatography on silica gel (30 g.) (developing solvent: chloroform) to give oily dimethyl 3-(N-ethoxycarbonyl-N-ethoxycarbonyloxyamino)-trans-1-propenylphosphonate (4.07 g.).

I.R. (liquid film): $\nu$max: 1790, 1720, 1640, 1250 (broad) cm$^{-1}$.

N.M.R.: $\delta$(ppm) in CDCl$_3$: 1.15–1.45 (6H, m), 3.72 (6H, d, J=12 Hz), 4.0–4.5 (6H, m), 5.94 (1H, m), 6.85 (1H, m).

(11) A solution of diethyl 3-bromo-trans-1-propenylphosphonate (23.83 g.) in N,N-dimethylformamide (50 ml.) was added dropwise to a suspension of ethyl N-ethoxycarbonyloxycarbamate (19.94 g.) in N,N-dimethylformamide (100 ml.) at −25°∼−30° C. in the course of 20 minutes. The reaction mixture was stirred at −20°−−30° C. for an hour and at −5°∼−10° C. for an hour. Subsequently, the resultant mixture was poured into a mixture of water (1 liter) and ethyl acetate (0.7 l). The ethyl acetate layer was separated and the aqueous layer was extracted twice with ethyl acetate (300 ml.). The combined ethyl acetate layer was washed with water (300 ml.), dried over magnesium sulfate and concentrated under reduced pressure to give an oily residue (28.89 g.), which was subjected to a column chromatography on silica gel [Developing solvent: a mixture of chloroform and ethyl acetate (4:1)]. The eluate was concentrated under reduced pressure to give oily diethyl 3-(N-ethoxycarbonyl-N-ethoxycarbonyloxyamino)-trans-1-propenylphosphonate (13.80 g.).

I.R. (liquid film): $\nu$max: 1795, 1730, 1640, 1210 (broad), 1170 cm$^{-1}$.

N.M.R.: $\delta$(ppm) in CDCl$_3$: 1.10–1.45 (12H, m), 3.83–4.50 (10H, m), 5.95 (1H, m), 6.74 (1H, m).

(12) A mixture of diethyl 3-chloro-2-methylpropylphosphonate (22.8 g.), potassium salt of ethyl N-ethoxycarbonyloxycarbamate (21.5 g.) and dry N,N-dimethylformamide (114 ml.) was stirred at 80°–85° C. for 3 hours and then concentrated under reduced pressure to give an oily residue, to which was added a mixture of water (100 ml.) and ethyl acetate (100 ml.) The ethyl acetate layer was separated and the resultant aqueous layer was saturated with sodium chloride and extracted again with ethyl acetate (50 ml.). The combined ethyl acetate layer was washed with aqueous solution saturated with sodium chloride, dried over magnesium sulfate and concentrated under reduced pressure to give oily diethyl 3-(N-ethoxycarbonyl-N-ethoxycarbonyloxyamino)-2-methylpropylphosphonate (30.2 g.).

N.M.R.: $\delta$(ppm) in CDCl$_3$: 1.03–1.53 (15H, m), 1.46–2.53 (3H, m), 3.58 (2H, d, J=6 Hz), 3.83–4.50 (8H, m).

(13) To a solution of hydroxylamine hydrochloride (55.6 g.) in water (100 ml.) were added solution of sodium hydroxide (32.0 g.) in water (75 ml.) under ice-cooling and then methanol (75 ml.). To this solution was added dropwise diethyl 3-bromopropylphosphonate (25.5 g.), whereafter the mixture was warmed at 40°–45° C. for 3 hours with stirring. The methanol was distilled off under reduced pressure. The resultant aqueous solution was adjusted to pH 8 with sodium bicarbonate, washed three times with benzene which were discarded (once with 150 ml. and twice with 100 ml. portions) and then extracted with three 150 ml. portions of chloroform. The chloroform extracts were combined, dried over magnesium sulfate and evaporated to dryness under reduced pressure to give oily diethyl 3-(N-hydroxyamino)propylphosphonate (13.05 g.).

I.R. (liquid film): $\nu_{max}$: 3350 (broad), 1240, 1170 cm$^{-1}$.

N.M.R.: $\delta$ppm in CDCl$_3$; 1.33 (6H, t, J=7 Hz), 1.5–2.2 (4H, m), 2.90 (2H, t, J=7 Hz), 4.13 (4H, quintet, J=7 Hz), 5.94 (2H, broad s).

(14) To a solution of diethyl 3-bromo-2-(tetrahydro-2H-pyran-2-yloxy)propylphosphonate (134.4 g.) in N,N-dimethylformamide (880 ml.) was added potassium salt of ethyl N-ethoxycarbonyloxycarbamate (88.45 g.) under ice-cooling, and the mixture was stirred at ambient temperature for half an hour, and then for additional 2.4 hours at 50° to 60° C. The solvent was distilled off under reduced pressure. The residue was dissolved in water (1300 ml.) and then extracted twice with ethyl acetate (1000 ml. and 800 ml.). The combined extracts were washed twice with a saturated aqueous sodium chloride solution (500 ml. and 300 ml.), dried over magnesium sulfate and evaporated to dryness under reduced pressure to give an oily residue (143.2 g.), which was subjected to column chromatography on silica gel (700 g.) and fractionated by elution with a mixture of chloroform and ethyl acetate (the ratio was gradually changed from 9:1 to 1:1 v/v respectively) and then ethyl acetate. The fractions containing an object compound were combined and evaporated to dryness under reduced pressure to give oily diethyl 3-(N-ethoxycarbonyl-N-ethoxycarbonyloxyamino)-2-(tetrahydro-2H-pyran-2-yloxy)propylphosphonate (62.6 g.).

I.R. (liquid film): $\nu_{max}$: 1780, 1730, 1220, 1170 cm$^{-1}$.

N.M.R.: $\delta$ppm in CDCl$_3$; 1.28–1.57 (12H, m), 1.72 (6H, m), 2.00 to 2.60 (2H, m), 3.45 to 4.58 (13H, m), 4.88 (1H, m).

Additionally diethyl 3-(N-ethoxycarbonyl-N-hydroxyamino)-2-(tetrahydro-2H-pyran-2-yloxy)prophylphosphonate (21.8 g.) was obtained from the later fractions of ethyl acetate eluates.

I.R. (liquid film): $\nu_{max}$: 3200, 1780, 1730, 1230, 1170 cm$^{-1}$.

N.M.R.: $\delta$ppm in CDCl$_3$; 1.18–1.52 (9H, m), 1.68 (6H, m), 1.90–2.68 (2H, m), 3.42–4.58 (11H, m), 4.83 (1H, m).

(15)

A mixture of diethyl 3-(N-ethoxycarbonyl-N-ethoxycarbonyloxyamino)-2-(tetrahydro-2H-pyran-2-yloxy)-propylphosphonate (54.0 g.), ethanol (100 ml.) and 0.1 N hydrochloric acid (100 ml.) was stirred for 4 hours at ambient temperature. After the reaction was completed, the ethanol was distilled off from the reaction mixture under reduced pressure to give an aqueous solution, which was extracted three times with ethyl acetate (200 ml. once and 50 ml. twice). The combined extracts were washed with a saturated sodium chloride aqueous solution, dried over magnesium sulfate, and evaporated to dryness under reduced pressure to give oily diethyl 3-(N-ethoxycarbonyl-N-ethoxycarbonyloxyamino)-2-hydroxypropylphosphonate (39.25 g.).

I.R. (liquid film): $\nu_{max}$: 3350, 1780, 1720, 1220, 1020 cm$^{-1}$.

N.M.R. $\delta$ppm in CDCl$_3$: 1.1–1.5 (12H, m), 1.90, 2.20 (2H, d, d, J=6 Hz, 18 Hz), 3.4–3.8 (2H, m), 3.8–4.5 (9H, m).

EXAMPLE FOR FORMATION OF HYDROXYAMINO FUNCTION (1) A mixture of diethyl 3-(N-butylideneamino)-propylphosphonate-N-oxide (6.5 g), acetic acid (20 ml) and conc. hydrochloric acid (20 ml) was refluxed with stirring for 5 hours. The resultant solution was concentrated under reduced pressure to give a residue, which was dissolved in water, and washed with ethyl acetate. After treatment with activated charcoal, the aqueous layer was concentrated under reduced pressure. The resulting residue was dissolved in a small volume of ethanol, and insoluble materials were removed by filtration. The filtrate was concentrated under reduced pressure to give a residue, which was dissolved in water (8 ml). The solution was adjusted to pH 4.0 with sodium bicarbonate and concentrated under reduced pressure to give an oil (4.5 g), which was dissolved in water (8 ml) and allowed to stand overnight at 5° C. The resulting crystals were separated by filtration and washed with a small volume of 50% aqueous ethanol to give crystalline 3-(N-hydroxyamino)propylphosphonic acid (0.48 g). Mp 161°–168° C. (dec.)

(2) A mixture of diethyl 3-(N-octylideneamino)-propylphosphonate-N-oxide (16.7 g), acetic acid (45 ml) and conc. hydrochloric acid (45 ml) was refluxed with stirring for 6.5 hours. The resultant mixture was concentrated under reduced pressure to give a residue, which was dissolved in a small volume of water. The aqueous solution was washed with ethyl acetate, treated with activated charcoal and concentrated under reduced pressure to give a residue, which was dissolved in a small volume of ethanol. After insoluble materials were removed by filtration, the filtrate was evaporated to dryness and the residue was dissolved in a small amount of water. This solution was passed through a columm packed with anion exchange resin Amberlite IR 400 (OH-type) (track name, made by Rohm & Haas Co.). The object compound was eluted with 1 N hydrochloric acid. The eluate was concentrated under reduced pressure to give an oil (4.5 g), which was passed through a column packed with cation exchange resin, Amberlite IR 120B (H-type) (trade name, made by Rohm & Haas Co.) and then the object compound was eluted with 1 N hydrochloric acid. The eluate was concentrated under reduced pressure to give an oil (3.0 g.), which was dissolved in water (4 ml). The aqueous solution was adjusted to pH 4.0 with sodium bicarbonate and allowed to stand overnight at 5° C. to give crystals, which were separated by filtration and dried to give crystalline 3-(N-hydroxyamino)propylphosphonic acid (1.0 g). The crystals were recrystallized from water (4 ml) to give purified 3-(N-hydroxyamino)propylphosphonic acid (0.42 g), Mp 159°–162° C. (dec.)

EXAMPLE FOR HYDROLYSIS (I)

(1) A mixture of dimethyl 3-(N-ethoxycarbonyl-N-ethoxycarbonyloxyamino)-trans-1-propenylphosphonate (3.70 g.) and trimethylbromosilane (8.71 g.) was stirred for 30 minutes under ice-cooling and for 30 minutes at ambient temperature. Subsequently, the reaction mixture was concentrated under reduced pressure to give a residue. To the residue was added water (25 ml.). After the mixture was stirred for an hour at ambient temperature, the mixture was washed three times with chloroform (10 ml.), and then concentrated under reduced pressure to give oily 3-(N-ethoxycarbonyl-N-ethoxycarbonyloxyamino)-trans-1-propenylphosphonic acid (2.80 g.). Furthermore, the combined chloroform layer was extracted with water (20 ml.). The aqueous layer was washed twice with chloroform (5 ml.) and concentrated under reduced pressure to recover the same object compound (0.43 g.).

I.R. (liquid film): $\nu$ max: 1780, 1710 (broad), 1640, 1220 (broad) cm$^{-1}$.

N.M.R.: $\delta$(ppm) in D$_2$O: 1.2–1.4 (6H, m), 4.04–4.46 (6H, m), 6.03 (1H, m), 6.55 (1H, m).

(2) Trimethylbromosilane (21.18 g.) was added to diethyl 3-(N-ethoxycarbonyl-N-ethoxycarbonyloxyamino)-trans-1-propenylphosphonate (12.2 g.) under ice-cooling. The mixture was stirred at ambient temperature for 3 hours and then concentrated under reduced pressure to give a residue, which was dissolved in water (30 ml.). The solution was stirred at ambient temperature for 30 minutes and then washed three times with chloroform (10 ml.). The aqueous layer was separated and concentrated under reduced pressure to give oily 3-(N-ethoxycarbonyl-N-ethoxycarbonyloxyamino)-trans-1-propenylphosphonate (5.90 g.). Furthermore, the same compound (3.58 g.) was recovered from the combined chloroform layer by extracting it with water, washing the aqueous extract with chloroform and concentrating it under reduced pressure.

I.R. (liquid film): $\nu$ max: 1780, 1710 (broad), 1640, 1220 (broad) cm$^{-1}$.

N.M.R. $\delta$(ppm) in D$_2$O: 1.2–1.4 (6H, m), 4.04–4.46 (6H, m), 6.03 (1H, m), 6.55 (1H, m).

(3) A mixture of diethyl 3-(N-hydroxyamino)propylphosphonate (12.9 g.), acetic acid (65 ml.) and 1 N hydrochloric acid (130 ml.) was heated to reflux with stirring for 8 hours and then was concentrated under reduced pressure to remove off acetic acid. The concentrate was decolorized by treating with an activated charcoal and evaporated to dryness under reduced pressure to give an oily residue (9.5 g.), which was dissolved in water (30 ml.) and adjusted to pH 4 with sodium bicarbonate (ca. 4.2 g.) to give crystals of 3-(N-hydroxyamino)propylphosphonic acid (4.80 g.), m.p. 160°–163.5° C. (decomp.). An additional crystals of the same object compound (0.91 g.) was recovered from the mother liquor after standing overnight at ambient temperature (m.p. 159°–163° C. (decomp.)). The I.R. and N.M.R. spectra of these crystals were superimposable with those of the authentic specimen (m.p. 160°–166° C. (decomp.)).

(4) To a solution of diethyl 3-(N-ethoxycarbonyl-N-ethoxycarbonyloxyamino)-2-(tetrahydro-2H-pyran-2-yloxy)propylphosphonate (5.01 g.) in methylene chloride (10 ml.), was added dropwise trimethylbromosilane (6.73 g.) with stirring under ice-cooling. The mixture was stirred for an hour under ice-cooling and for additional 2 hours at ambient temperature and evaporated under reduced pressure to remove off the solvent and unreacted excess trimethylbromosilane. The residue was dissolved in water (50 ml.), stirred for an hour at ambient temperature and washed twice with chloroform (20 ml. and 10 ml. portions). The combined chloroform washings were extracted with water (30 ml.). The aqueous extract was washed once again with chloroform (5 ml.) and combined with the above-remained aqueous solution and then evaporated to dryness under reduced pressure to give a tarry residue. This residue was dissolved in water (40 ml.) treated with an activated charcoal (300 mg.) and evaporated to dryness under reduced pressure to give oily 3-(N-ethoxycarbonyl-N-hydroxyamino)-2-hydroxypropylphosphonic acid (2.6 g.).

N.M.R.: δppm in D$_2$O; 1.37 (3H, t, J=7 Hz), 1.98–2.62 (2H, m), 3.40–4.00 (2H, m), 4.15–4.55 (3H, m).

(5) Trimethylbromosilane (122 g.) was added dropwise to a solution of diethyl 3-(N-ethoxycarbonyl-N-ethoxycarbonyloxyamino)-2-(tetrahydro-2H-pyran-2-yloxy)propylphosphonate (79.4 g.) in methylene chloride (160 ml.) under ice-cooling with stirring over a period of 15 minutes. The mixture was further stirred for an hour at 0°–5° C. and for additional 2.5 hours at ambient temperature, and then evaporated under reduced pressure. The oily residue was dissolved in water (500 ml.) stirred at ambient temperature for an hour, and then washed twice with chloroform (200 and 200 ml. portions) to remove off bis(trimethylsilyl)ether. The combined chloroform washings were back extracted once with water (50 ml.). The combined aqueous layers were evaporated under reduced pressure. The dark brown oily residue was dissolved in water (300 ml.) washed twice with chloroform (each 150 ml. portion) and ethyl acetate (100 ml.) successively, treated with activated charcoal (2.5 g.), and evaporated under reduced pressure. The oily residue was dissolved in 1 N hydrochloric acid (750 ml.) treated with activated charcoal (2.5 g.) and then heated to reflux for 13.5 hours. The mixture was evaporated under reduced pressure. The oily residue was dissolved in a mixture of water (50 ml.) and methanol (100 ml.) adjusted to pH about 4 with propylene oxide, and diluted with ethanol (300 ml.). The oily precipitates were collected by decantation, and dissolved in water (60 ml.). This aqueous solution was diluted with methanol (120 ml.) under heating at 60° C., and then allowed to stand overnight at ambient temperature. The precipitates were collected by filtration, washed twice with 80% aqueous methanol (each 20 ml. portion) and methanol (20 ml.), and then dried on phosphorus pentoxide to give 2-hydroxy-3-(N-hydroxyamino)propylphosphonic acid (10.60 g.). M.p. 153°–155° C.

I.R. (Nujol): ν$_{max}$: 3450, 3600 - 2200, 1610, 1580, 1200, 1110, 1050, 910 cm$^{-1}$.

N.M.R. δppm in D$_2$O: 1.75, 2.08 (2H, d, d, J=7 Hz, 18 Hz), 3.0–3.7 (2H, m), 4.0–4.5 (1H, m).

(6) To a solution of diethyl 3-(N-ethoxycarbonyl-N-ethoxycarbonyloxyamino)-2-hydroxypropylphosphonate (24.0 g.) in methylene chloride (50 ml.) was added dropwise trimethylbromosilane (41 ml.) under ice-cooling, whereafter the mixture was stirred for half an hour at the same temperature and then for additional 2.5 hours at ambient temperature. After the reaction was completed, the chloroform and the excess of the trimethylbromosilane was distilled off from the reaction mixture under reduced pressure to give a residue, which was dissolved in water (125 ml.) and stirred for an hour at ambient temperature. This aqueous solution was washed three times with chloroform (each 30 ml. portion) and evaporated to dryness under reduced pressure to give a residue, which was dissolved in 1 N hydrochloric acid (240 ml.) and heated to reflux for 15 hours. The resultant aqueous solution was evaporated to dryness under reduced pressure to give a residue, which was dissolved in water (60 ml.), decolorized with activated charcoal (500 mg.) and evaporated to dryness under reduced pressure. The residue thus obtained was dissolved in a mixture of water (20 ml.) and methanol (40 ml.), and adjusted to pH 3–4 with propylene oxide (about 25 ml.) to precipitate oily materials. Furthermore, to this solution was added ethanol (80 ml.) and allowed to stand for a while in order to precipitate said materials completely, and these materials were collected by decantation and dissolved in water (20 ml.). The insoluble materials were removed by filtration, and to the filtrate was added methanol (35 ml.) at 50°–60° C. The resultant solution was allowed to stand for 3.5 hours at ambient temperature, and precipitating crystals were collected by filtration, washed twice with methanol (10 ml.) and dried on phosphorus pentoxide to give 2-hydroxy-3-(N-hydroxyamino)propylphosphonic acid (5.9 g.).

This object compound was identified by comparing its I.R. and N.M.R. spectra with those of the object compound of the above Example (5).

EXAMPLES FOR HYDROLYSIS [II]

(1) A mixture of diethyl 3-[N-(p-methoxybenzyloxy)-N-tosylamino]propylphosphonate (3.0 g), 6 N hydrochloric acid (25 ml) and acetic acid (25 ml) was refluxed with stirring for 12 hours. The resultant mixture was concentrated under reduced pressure to give a brownish oily residue. The residue was washed with ethyl ether (100 ml), and then water (100 ml) was added thereto with stirring. Insoluble materials were filtered off from the mixture, whereafter the filtrate was washed with ethyl ether, and then treated with an activated charcoal. The aqueous solution was concentrated under reduced pressure to give a faint yellowish oily residue. The residue was allowed to stand overnight in desiccator under reduced pressure to give crystals. The crystals were washed with ethyl ether to give p-toluene sulfonic acid salt of 3-(N-hydroxyamino)propylphosphonic acid (1.50 g) in the form of faint yellowish crystals. MP: 129°~135° C.

(2) A mixture of dibutyl 3-[N-(p-methoxybenzyloxy)-N- tosylamino]propylphosphonate (28.4 g), 6N hydrochloric acid (280 ml) and acetic acid (280 ml) was refluxed with stirring for 20 hours. The resultant mixture was concentrated under reduced pressure to give a residue, and then water was added thereto. The mixture was treated with an activated charcoal, whereafter the mixture was concentrated under reduced pressure to give an oily residue. The oily residue was washed with ether and dried under reduced pressure. The solid was washed with acetonitrile and ethyl ether to give p-toluenesulfonic acid salt of 3-(N-hydroxyamino)propylphosphonic acid (12.4 g) in the form of crystals. MP: 129°~135° C.

A solution of p-toluenesulfonic acid salt of 3-(N-hydroxyamino)propylphosphonic acid (12.0 g), obtained above, in water (100 ml) was passed through a column packed with a cation exchange resin, Amberlite IR 120B (trade name, made by Rohnm & Haas Co.; H+ type). The column was washed with water (800 ml) and then elution was conducted with 1 N hydrochloric acid (800 ml). The eluate was concentrated under reduced pressure to remove completely water. The residue thus obtained, was pulverized with acetonitril (300 ml) to give a powder, which was washed twice with ethyl ether (50 ml) to give hydrochloric acid salt of 3-(N-hydroxyamino)propylphosphonic acid (4.30 g) in the form of powder.

| NMR Absorption Spectrum (DMSO-d$_6$) | |
|---|---|
| δ(ppm) | |
| 1.4~2.2 | (4H, m) |

| NMR Absorption Spectrum (DMSO-d$_6$) |  |
|---|---|
| δ(ppm) |  |
| 3.16 | (2H, m) |

(3) A mixture of diethyl 3-(N-benzyloxy-N-tosylamino)propylphosphonate (13.2 g), conc. hydrochloric acid (130 ml) and acetic acid (130 ml) was refluxed with stirring for 45 hours. The resultant mixture was concentrated under reduced pressure to give a residue and then water and an activated charcoal was added thereto, whereafter the mixture was filtered. The filtrate was concentrated under reduced pressure, and the resultant residual oil (8.59 g) was dissolved in water (25 ml). To the solution were added pyridine (2.08 g) and ethanol (5 ml), and then the mixture was allowed to stand overnight at 4° C. to give 3-(N-hydroxyamino)propylphosphonic acid 82.30 g) in the form of crystals. MP: 160°~166° C. (dec.).

(4) A mixture of dibutyl 3-[N-isobutoxycarbonyl-N-(p-methoxybenzyloxy)amino]propylphosphonate (6.04 g), conc. hydrochloric acid (60 ml) and acetic acid (60 ml) was refluxed with stirring for 21 hours. The resultant mixture was concentrated under reduced pressure, and to the residue was added water. The mixture was concentrated under reduced pressure to give a residue, which was washed with acetonitrile and then dissolved in water (10 ml). To the solution were added pyridine (800 ml) and ethanol (4 ml), and then the mixture was allowed to stand overnight at 4° C. to give 3-(N-hydroxyamino)propylphosphonic acid (1.02 g) in the form of crystals. MP: 160°~166° C. (dec.).

(5) A solution of dibutyl 3-(N-benzyloxy-N-ethoxycarbonylamino)propylphosphonate (6.72 g.) in acetic acid (70 ml.) and conc. hydrochloric acid (70 ml.) was refluxed with stirring for 48 hours. The reaction mixture was concentrated under reduced pressure to give an oily residue, to which there was added water (30 ml.). The solution was washed with ethyl acetate (20 ml.), treated with activated charcoal and then concentrated under reduced pressure to give an oily residue (2.60 g.). The residue was dissolved in water (5 ml.). To the solution was added pyridine (1.08 g.) and ethanol (2 ml.). The mixture was allowed to stand overnight at ambient temperature to give crystalline 3-(N-hydroxyamino)propylphosphonic acid (1.12 g.).

N.M.R.: δ(ppm) in D$_2$O; 1.3–2.4 (4H, m), 3.37 (2H, t).

(6) A mixture of diethyl 3-(N-methoxy-N-methoxycarbonylamino)propylphosphonate (4.0 g), acetic acid (20 ml) and conc. hydrochloric acid (20 ml) was refluxed for 15 hours. The resultant mixture was concentrated under reduced pressure to give a residue, which was dissolved in ethanol (15 ml). The solution was neutralized with pyridine to give crystals, which were separated by filtration, washed with a small volume of ethanol and dried to give crystalline 3-(N-methoxyamino)propylphosphonic acid (1.52 g).

Mp 167°–169° C. (dec.)

I.R. Nujol): ν max: 3400–2000, 1630, 1545, 1235, 1125, 1050, 980, 925, 905 cm$^{-1}$.

N.M.R.: δ(ppm) in D$_2$O; 1.3–2.3 (4H, m), 3.42 (2H, t, J=7 Hz), 3.90 (3H, s).

(7) A solution of diethyl 3-(N-ethoxycarbonyl-N-ethoxycarbonyloxyamino)propylphosphonate (146.0 g) in conc. hydrochloric acid (1020 ml) was refluxed for 9 hours. After concentration of the reaction mixture under reduced pressure, the residue was dissolved in water (200 ml) and treated with activated charcoal (6 g). The activated charcoal was removed by filtration and the filtrate was concentrated under reduced pressure and the resulting oil (86.7 g) was dissolved in water (160 ml).

After the solution was adjusted to pH 4.0 with 30% aqueous ammonia under ice-cooling, ethanol (80 ml) was added to the solution to give crystals which were separated by filtration and washed with ethanol (80 ml) to give crystalline 3-(N-hydroxyamino)propylphosphonic acid (37.78 g).

The mother liquor and the ethanol washings were combined and then allowed to stand overnight to give the same crystalline object compound (6.07 g). Mp 162°–164° C. (dec.)

I.R. (Nujol): νmax: 1640, 1595, 1240, 1220, 1190 cm$^{-1}$.

N.M.R. δ(ppm) in D$_2$O; 1.3–2.35 (4H, m), 3.36 (2H, t, J=7 Hz).

(8) A mixture of diethyl 5-(N-ethoxycarbonyl-N-ethoxycarbonyloxyamino)pentylphosphonate (90.0 g.) and conc. hydrochloric acid (630 ml.) was refluxed for 14 hours and concentrated under reduced pressure to give a residue, which was dissolved in water (200 ml.). The aqueous solution was washed with ethyl acetate, treated with activated charcoal and then concentrated under reduced pressure to give an oily residue (53.7 g.). The residue was dissolved in a mixture of water and methanol (1:2). The solution was adjusted to pH 4.0 with 28% aqueous ammonia under ice-cooling to give precipitates, which were separated by filtration, washed with methanol and dried to give crude crystals. The crystals were dissolved in 20-fold volume of water under heating, treated with activated charcoal and then cooled to ambient temperature. To the solution was added ethanol (100 ml.) and then allowed to stand overnight at 4° C. to give crystals, which were separated by filtration and dried to give crystalline 5-(N-hydroxyamino)pentylphosphonic acid (18.8 g.). M.p. 184°–185.5° C. (dec.).

N.M.R.: δ(ppm) in D$_2$O: 1.20–2.02 (8H, m), 3.30 (2H, t, J=7 Hz).

(9) To a solution of diethyl 2-(N-benzyloxy-N-tosylamino)ethylphosphonate (12.5 g.) in acetic acid (65 ml.) was added conc. hydrochloric acid (130 ml.). The mixture was refluxed for 42 hours at 140° C., concentrated under reduced pressure to give a residue, which was dissolved in water (60 ml.). To the aqueous solution was added ethyl acetate (60 ml.). The aqueous layer was separated, washed with ethyl acetate, treated with activated charcoal and concentrated under reduced pressure to give an oily residue (8.9 g.), which was dissolved in ethanol (50 ml.) and adjusted to pH 4.0 with pyridine to give crystals. The crystals were separated by filtration, washed with ethanol and dried to give crystalline 2-(N-hydroxyamino)ethylphosphonic acid (3.5 g.), which was recrystallized from a mixture of water and ethanol (2:1) to give crystals of the same compound (2.4 g.). M.p. 173°–173.5° C. (dec.).

N.M.R.: δ(ppm) in D$_2$O: 2.04 (2H, m), 3.60 (2H, m).

(10) A mixture of di-tert.-butyl 3-(N-ethoxycarbonyl-N-ethoxycarbonyloxyamino)trans-1-propenylphosphonate (8.60 g.) and 1 N hydrochloric acid (250 ml.) was refluxed for 15 hours. The resultant mixture was concentrated under reduced pressure to give a residue, which was dissolved in water (100 ml.) and treated with activated charcoal. The solution was concentrated under reduced pressure to give a residue (4 g.), which was dissolved in water (10 ml.) and adjusted to pH 4 with 1 N aqueous sodium hydroxide solution. The aqueous solution was passed through a column of anion exchange resin, Amberlite IRA-400 (trade name, made by Rhom & Hass Co.) (OH⁻ form). The object compound was eluted from the resin with 1 N hydrochloric acid and then the eluate was concentrated under reduced pressure to give an oily residue (3.4 g.), which was dissolved in a mixture of water (0.5 ml.) and ethanol (20 ml.). The solution was adjusted to pH 4 with pyridine and concentrated under reduced pressure to give a residue, which was pulverized with methanol to give powder (1 g.). The powder was dissolved in water (0.5 ml.). To the aqueous solution was added methanol to give precipitates which were separated by filtration and dried to give powdery 3-(N-hydroxyamino)-trans-1-propenylphosphonic acid (280 mg.). Furthermore, the same object compound (120 mg.) was recovered from the mother liquor.

I.R. (Nujol): $\nu$max: 1630, 1260 cm$^{-1}$.

N.M.R.: $\delta$(ppm) in D$_2$O: 3.99 (2H, d.d. J=5 and 1 Hz), 6.05–6.65 (2H, m).

(11) A mixture of 3-(N-ethoxycarbonyl-N-ethoxycarbonyloxyamino)-trans-1-propenylphosphonic acid (8.53 g.) and 1 N hydrochloric acid (250 ml.) was refluxed for 16 hours. The resultant mixture was concentrated under reduced pressure to give a residue, which was dissolved in water (30 ml.). The aqueous solution was treated with activated charcoal (0.5 g.) and concentrated under reduced pressure to give an oily residue (5.85 g.), which was dissolved in water (10 ml.). The aqueous solution was passed through a column of anion exchange resin, Amberlite IRA 400 (100 ml.). The column was washed with water (600 ml.) and the object compound was eluted with 1 N hydrochloric acid (300 ml.). The eluate was concentrated under reduced pressure to give an oily residue (3.9 g.), to which were added ethanol (10 ml.) and water (2 ml.). The mixture was adjusted to pH 4–4.5 with pyridine and then to the mixture was added ethanol (30 ml.). The supernatant was removed by decantation to give residue, which was pulverized with ethanol (30 ml.) to give powdery 3-(N-hydroxyamino)-trans-1-propenylphosphonic acid (2.38 g.).

I.R. (Nujol): $\nu$max: 1630, 1260 cm$^{-1}$.

N.M.R.: $\delta$(ppm) in D$_2$O: 3.99 (2H, d,d, J=5 and 1 Hz), 6.05–6.65 (2H, m).

(12) A mixture of diethyl 3-(N-ethoxycarbonyl-N-ethoxycarbonyloxyamino)-2-methylpropylphosphonate (28.3 g.) and conc. hydrochloric acid (280 ml.) was refluxed for 18 hours and then concentrated under reduced pressure to give an oily residue. To the residue was added a mixture of water (100 ml.) and ethyl acetate (100 ml.). From the resultant mixture, the aqueous layer was separated, treated with activated charcoal and concentrated under reduced pressure to give an oily residue. The residue was dissolved in a mixture of methanol (30 ml.) and water (15 ml.). The solution was adjusted to pH 4.0 with aqueous ammonia under ice-cooling and concentrated under reduced pressure to give a residue, which was passed through a column of anion exchange resin, Amberlite IRA-400 (OH⁻ form). The column was washed with water and then the object compound was eluted with 1 N hydrochloric acid. The eluate was concentrated under reduced pressure to give oily hydrochloric acid salt of 3-(N-hydroxyamino)-2-methylpropylphosphonic acid (9.6 g.).

N.M.R.: $\epsilon$(ppm) in D$_2$O: 1.22 (3H, d, J=6 Hz), 1.58–2.58 (3H, m), 3.32 (2H, d, J=6 Hz).

(13) A solution of sodium hydroxide (14.0 g.) in water (175 ml.) was heated to reflux for a while under bubbling with nitrogen gas. To this solution was added diethyl 3-(N-ethoxycarbonyl-N-ethoxycarbonyloxyamino)propylphosphonate (24.8 g.), and the mixture was heated to reflux for 1.5 hours with stirring under nitrogen atmosphere. After cooling, the reaction mixture was adjusted to pH 4.0 with 10% hydrochloric acid and then concentrated under reduced pressure to about half of the original volume. The aqueous concentrate was adjusted to pH 1.0 with 10% hydrochloric acid, washed with three 50 ml. portions of n-butanol, which were discarded, and adjusted to pH 4.0 with 20% aqueous sodium hydroxide solution and then evaporated under reduced pressure. The residue was dissolved in ethanol (50 ml.) and evaporated to dryness under reduced pressure to remove off a residual water as thoroughly as possible. The solid residue was dissolved in hot methanol (120 ml.), and insoluble solid (sodium chloride) was filtered off and the filtrate evaporated to dryness under reduced pressure. The crystalline residue thus obtained was treated with ethanol (100 ml.) and collected by filtration to give monoethyl 3-(N-hydroxyamino) propylphosphonate (6.5 g.).

N.M.R.: $\delta$ppm in D$_2$O; 1.22 (3H, t, J=7 Hz), 1.48–2.20 (4H, m), 3.37 (2H, t, J=6 Hz). 3.89 (2H, quintet).

(14) A solution of 3-(N-ethoxycarbonyl-N-hydroxyamino)-2-hydroxypropylphosphonic acid (2.4 g.) in 1 N hydrochloric acid (100 ml.) was heated to reflux for 14 hours. The reaction mixture was evaporated to dryness under reduced pressure to give a residue, to which was added water (20 ml.), washed twice with chloroform (each 10 ml. portion) and decolorized with activated charcoal (200 mg.). The activated charcoal was filtered off and the filtrate was evaporated to dryness under reduced pressure to give a dark reddish oil, to which was added water (3 ml) and adjusted to pH 4.0 with 28% aqueous ammonia. This aqueous solution was diluted with methanol and allowed to stand at ambient temperature, and then the precipitating crystals were collected by filtration to give 2-hydroxy-3-(N-hydroxyamino)propylphosphonic acid (0.62 g.).

This object compound was identified by comparing its I.R. and N.M.R. spectra with those of the object compound of Example (5) in Hydrolysis (I).

EXAMPLES FOR N-ACYLATION (1) Acetic anhydride (4.51g) was added to a suspension of 3-(N-hydroxyamino)propylphosphonic acid (3.80 g) in water (20 ml) at an ambient temperature, while stirring. After the stirring was continued for 1.5 hours, the resultant mixture was adjusted to pH 2.5 with 1 N aqueous sodium hydroxide solution and then concentrated under reduced pressure. To the residual oil was added water (40 ml), and then concentrated under reduced pressure. This operation was repeated once again. The residual oil was washed twice with ethyl ether (60 ml), and then dissolved in ethanol (5 ml). To the solution, there was added ethyl ether (50 ml) to reprecipitate the oil. The upper layer was removed by decantation. This operation was repeated once again. The oil thus obtained, was dissolved in water (50 ml), adjusted to pH 6.5 and then concentrated under reduced pressure to give a foamy residue. n-Butanol was added to the foamy residue and concentrated under reduced pressure to remove completely water. The resultant residual oil was pulverized with isopropanol and then the obtained powder was washed with isopropanol and ethyl ether, respectively and then dried to give a crude powder (5.58 g). The crude powder was recrystallized from a mixture of methanol and acetone to give monosodium salt of 3-(N-acetyl-N-hydroxyamino)propylphosphonic acid (3.75 g). MP: 187°~188° C.(dec.)

(2) p-Toluensulfonic acid salt of 3-(N-hydroxyamino)propylphosphonic acid (980 mg) was dissolved in a mixture of water (12 ml), 1 N aqueous potassium hydroxide solution (12 ml) and acetone (20 ml). To the solution was added dropwise a solution of benzoyl chloride (1.70 g) in dry acetone (12 ml) under ice-cooling, with stirring. During the period, the solution was adjusted to pH 7.5–9 with 1 N aqueous potassium hydroxide solution. The resultant mixture was adjusted to ph 10 and stirred for an hour, whereafter the mixture was adjusted to pH 7 and then acetone was distilled off under reduced pressure. The resultant residue was adjusted to pH 4 with 10% hydrochloric acid and washed with ethyl ether. The aqueous layer was adjusted to pH 1.6 with 10% hydrochloric acid, and then water was added thereto to give 150 ml of a solution. The solution was passed through a column of activated charcoal. The column was washed with water, and then elution was conducted with 70% aqueous acetone. The elutate was concentrated under reduced pressure to give a residual oil (960 mg). This purification operation using a column of an activated charcoal was repeated once again to give a residual oil (460 mg). The oil was dissolved in water (30 ml) and adjusted to pH 6.5 with 1 N aqueous sodium hydroxide solution. The solution was concentrated under reduced pressure and then the obtained residue was pulverized with ethanol to give monosodium salt of 3-(N-benzoyl-N-hydroxyamino)propylphosphonic acid in the form of powder.

| NMR Absorption Spectrum (D$_2$O): | |
|---|---|
| δ(ppm) | |
| 1.8~2.1 | (4H, m) |
| 3.77 | (2H, t, J=6Hz) |
| 7.57 | (5H, s) |

(3) Thienylacetyl chloride (1350 mg) was added dropwise to a solution of 3-(N-hydroxyamino)propylphosphonic acid (755 mg) and sodium bicarbonate (1.26 g) in a mixture of water (15 ml) and methanol (10 ml) under ice-cooling with stirring for 1.5 hours. During the period, the reaction mixture was adjusted to pH 7–8 with 5% aqueous sodium bicarbonate solution. The reaction mixture was adjusted to pH 10 and stirred under ice-cooling for additional 45 minutes. The resultant mixture was adjusted to ph 7 with 10% hydrochloric acid and methanol was distilled off under reduced pressure. The residue thus obtained, was adjusted to pH 2 with 10% hydrochloric acid, washed twice with ethyl ether (30 ml) and then extracted three times with n-butanol (30 ml). The combined n-butanol layer was dried under reduced pressure to give 3-(N-hydroxy-N-thienylacetyl)propylphosphonic acid (960 mg) in the form of powder. The powder was crystallized from a mixture of ethanol and ethyl ether to give 3-(N-hydroxy-N-thienylacetylamino)propylphosphonic acid (200 mg) in the form of colorless needles.

MP: 128°~131° C. (dec.).

(4) A solution of N-benzyloxycarbonylaminoacetyl chloride (2.85 g) in ethyl ether (5 ml) was added dropwise to a solution of 3-(N-hydroxyamino)propylphosphonic acid (985 mg) and sodium bicarbonate (1.51 g) in a mixture of water (20 ml) and methanol (20 ml) with stirring under ice-cooling. During the period, the reaction mixture was adjusted to pH 7–8 with 5% aqueous sodium bicarbonate solution. The stirring was continued for an hour, whereafter the mixture was adjusted to pH 10 with 1 N aqueous sodium hydroxide solution and stirred at the same temperature for 45 minutes. The resultant mixture was adjusted to pH 7 and methanol was distilled off under reduced pressure. The resultant aqueous solution was adjusted to pH 2 with 10% hydrochloric acid and washed with ethyl acetate (30 ml), whereafter the solution was adjusted to pH 1 with 10% hydrochloric acid and then extracted twice with n-butanol (30 ml). The combined n-butanol layer was concentrated under reduced pressure to give a residue, which was crystallized from ether to give 3-[N-(N-benzyloxycarbonylaminoacetyl)N-hydroxyamino]propylphosphonic acid (720 mg) in the form of crystals MP: 101°~105° C.

The obtained 3-[N-(N-benzyloxycarbonylaminoacetyl)-N-hydroxyamino]propylphosphonic acid was hydrolyzed to give 3-(N-aminoacetyl-N-hydroxyamino)propylphosphonic acid in the following manner.

48% Hydrogen bromide-acetic acid (1 ml) was added under ice-cooling to a solution of 3-[N-(N-benzyloxycarbonyl-aminoacetyl)-N-hydroxyamino]propylphosphonic acid (200 mg) in acetic acid (1 ml) and the reaction mixture was stirred at an ambient temperature for an hour. To the resultant mixture was added dry ethyl ether (20 ml) to precipitate an oil. The oil was separated, washed twice with dry ethyl ether (10 ml) and then dissolved in water (0.5 ml). The solution was adjusted to pH 4 with pyridine and ethanol (5 ml) was added thereto to give precipitates. The upper layer was removed by decantation and the precipitates was pulverized with ethyl ether (10 ml) to give 3-(N-aminoacetyl-N-hydroxyamino)propylphosphonic acid (40 mg) in the form of powder.

Infrared Absorption Spectrum (Nujol): $\nu_{max}$=3400~2600, 1650, 1270, 1220, 1110, 1030, 900 cm$^{-1}$.

| NMR Absorption Spectrum (D$_2$O): | |
|---|---|
| δ(ppm) | |
| 1.6~2.2 | (4H, m) |
| 3.67 | (2H, t, J=5Hz) |
| 4.05 | (2H, s) |

(5) Formic acid (20 ml.) was added dropwise to acetic anhydride (40 ml.) at 0°–5° C. in the course of 15 minutes with stirring. After stirring was continued at the same temperature for 10 minutes and then at 45°–50° C. for 15 minutes, the mixture was cooled down to 0°–5° C. To this cooled mixture was added dropwise a solution of 3-(N-hydroxyamino)propylphosphonic acid (32.8 g.) in formic acid (60 ml.) at the same temperature in the course of 20 minutes, stirred for additional 45 minutes at ambient temperature, and then the resultant mixture was concentrated under reduced pressure. The residue was dissolved in ethanol (300 ml.), treated with activated charcoal (6 g.) and then filtered. The filtrate was diluted with ethanol (200 ml.) and treated with 28% aqueous ammonia (28 ml.) with stirring under ice-cooling to give an oily precipitate. The precipitate was separated by decantation and dissolved in water (120 ml.). The aqueous solution was treated with activated charcoal (4 g.), and filtered. To the aqueous filtrate was added ethanol (800 ml.) at 80° C. and allowed to stand overnight at ambient temperature to give crystalline monoammonium salt of 3-(N-formyl-N-hydroxyamino)-propylphosphonic acid (30.55 g.), mp 158°–160.5° C. (dec.) The same monoammonium salt (4.35 g.) was recovered additionally from the mother liquor, by concentrating it to about 100ml under reduced pressure mixing with ethanol (300 ml.) and allowing to stand at ambient temperature for 2 hours.

(6) To a cooled mixture of formic acid (2 ml.) and acetic anhydride (4 ml.) at 0°–5° C., which was prepared in the same manner as above, was added dropwise 3-(N-hydroxyamino)propyl phosphonic acid (3.28 g.), and stirred at ambient temperature for an hour. The resultant mixture was concentrated under reduced pressure. The oily residue was washed with ether (50 ml.×3) and then dissolved in water (60 ml.). The aqueous solution was adjusted to pH 4.8 with 1N aqueous sodium hydroxide solution and concentrated under reduced pressure. The residue was dissolved in methanol (50 ml.) and was added ethanol (10 ml.) at 60° C., to give an oily precipitate, which was removed off by decantation. The alcoholic solution was treated with ethanol (50 ml.) to give solid precipitates, which was collected by filtration, washed with ethanol and dried to give monosodium salt of 3-(N-formyl-N-hydroxyamino)propylphosphonic acid as an powder (3.52 g.). The powder was further purified by reprecipitation in the following manner. A solution of this powder in methanol (80 ml.) was diluted with ethanol (100 ml.) at ambient temperature with stirring. Stirring was continued overnight at ambient temperature to give precipitates, which was filtered, washed with ethanol and then dried to give a purified monosodium salt of 3-(N-formyl-N-hydroxyamino)propylphosphonic acid (2.50 g.).

I.R. (nujol)νmax: 3600–2200, 1675, 1510, 1270, 1230, 1165, 1015, 985, 920, 885 cm$^{-1}$.

| N.M.R.: δ(ppm) in D$_2$O; | |
|---|---|
| 1.2–2.2 | (4H, m) |
| 3.62 | (2H, t, J = 6Hz) |
| 7.98 | (s) ⎫ 1H |
| 8.33 | (s) ⎭ |

(7) To a cooled mixture of formic acid (1 ml.) and acetic anhydride (2 ml.) at 0°–5° C., which was prepared in the same manner as aforementioned, was added dropwise (3-(N-hydroxyamino)propylphosphonic acid (1.64 g.), stirred at ambient temperature for an hour, and then concentrated under reduced pressure. The residue was dissolved in 1N aqueous potassium hydroxide solution (10 ml.) and evaporated to dryness under reduced pressure. The residue became to crystallize after standing at ambient temperature for 3 hours, which was treated with methanol collected by filtration (1.13 g.) and recrystallized from 20% aqueous ethanol to give crystalline potassium salt of 3-(N-formyl-N-hydroxyamino)propylphosphonic acid (0.73 g.), mp. 202°–204° C. (dec.).

I.R.(nujol)νmax: 2700–2200, 1655, 1560, 1310, 1260, 1220, 1190, 1155, 1125, 1000, 940, 890 cm$^{-1}$.

| N.M.R.: δ(ppm) in D$_2$O; | |
|---|---|
| 1.25–2.3 | (4H, m) |
| 3.65 | (2H, t,J = 6Hz) |
| 8.00 | (s) ⎫ 1H |
| 8.35 | (s) ⎭ |

(8) To a solution of 3-(N-hydroxyamino)propylphosphonic acid (2.46 g.) in a mixture of water (15 ml.) and acetone (15 ml.) was added dropwise butyric anhydride (4.75 g.) in the course of 15 minutes with stirring at ambient temperature. After stirring was continued at the same temperature for additional one hour, the resultant mixture was concentrated under reduced pressure. The oily residue was dissolved in 1N aqueous sodium hydroxide solution (15 ml.) and evaporated to dryness under reduced pressure. The residue was washed with ether (50 ml.×3) by decantation, dissolved in ethanol (70 ml.), heated to reflux for 2 hours, and then evaporated to dryness under reduced pressure. The resultant residue was triturated with ether and filtered to give a powder (2.50 g.), which was treated with hot (60° C.) acetone (60 ml.). Insoluble materials were collected by filtration, washed with a small amount of acetone and dried to give a solid monosodium salt of 3-(N-butyryl-N-hydroxyamino)propylphosphonic acid (690 mg.), which was recrystallized from isopropanol to give needles, mp: 182°–187° C. (dec.).

(9) A mixture of benzoyloxyacetic acid (5.4 g.) and thionyl chloride (50 ml.) was stirred at 70°–80° C. for an hour and then excess thionyl chloride was distilled off under reduced pressure to give benzoyloxyacetyl chloride. A solution of benzoyloxyacetylchloride obtained above in acetone (10 ml.) was added dropwise to a solution of 3-(N-hydroxyamino)propylphosphonic acid (1.64 g.) in a mixture of water (16 ml.) and acetone (20 ml.) over 30 minutes interval with stirring under ice-cooling and maintaining carefully the pH at around 7–8, together with by adding dropwise a 5% aqueous sodium bicarbonate solution and stirring was continued for additional 30 minutes.

After acetone was distilled off from the reaction mixture under reduced pressure, the residual solution was adjusted at around pH 11–12 and stirred for an hour under maintaining the pH at around 11–12 with 1N aqueous sodium hydroxide solution. The resultant mixture was acidified to about pH 2 with 10% hydrochloric acid and washed out twice with ethyl acetate. The aqueous layer was taken up, adjusted to about pH 1.5–2 and subjected to column chromatography on activated charcoal. After the column was washed with a small portion of water, the object compound was eluted with 70% (V/V) aqueous acetone. The fractions containing the object compound was collected, adjusted to pH 5 with 1N aqueous sodium hydroxide solution and concentrated under reduced pressure to give monosodium salt of 3-(N-hydroxyacetyl-N-hydroxyamino)propylphosphonic acid (300 mg.) as a powder.

I.R.(nujol)νmax: 3600–2200, 1640, 1280, 1225, 1130, 1040, 900 cm$^{-1}$.

N.M.R.: δ (ppm) in D$_2$O; 1.3–2.2 (4H, m), 3.73 (2H, t, J=8Hz), 4.47 (2H, s).

(10) Chloroacetyl chloride (4.52 g.) was added dropwise to a solution of 3-(N-hydroxyamino)propylphosphonic acid (2.46 g.) in a mixture of water (15 ml.) and acetone (15 ml.) over a 20 minutes-interval with stirring under ice-cooling and maintaining the pH at around 7–8 by adding 5% aqueous sodium bicarbonate solution. After stirring for further hour, the reaction mixture was adjusted to pH 9 with 1N aqueous sodium hydroxide solution and stirred at ambient temperature for 35 minutes. After acetone was distilled off under reduced pressure, the aqueous solution was acidified to pH 1.8 with 10% hydrochloric acid and evaporated to dryness under reduced pressure. The residue was dissolved in ethanol (40 ml.) and heated for 10 minutes at 60° C.

The insoluble substance was separated out and the ethanolic layer was allowed to stand overnight at ambient temperature to give crystalline 3-(N-chloroacetyl-N-hydroxyamino)propylphosphonic acid (1.85 g.), mp: 163°–165° C. (dec.).

(11) A mixture of 3-(N-hydroxyamino)propylphosphonic acid (1.64 g.) in 1N aqueous sodium hydroxide solution (10 ml.) and S-methylisothiourea sulfate (1.40 g.) in water (5 ml.) was heated to reflux for 1.5 hours and allowed to stand overnight at ambient temperature to give crystalline precipitates, which was collected by filtration and washed with water and then with ethanol to give 3-(1-hydroxyguanidino)propylphosphonic acid (690 mg.), mp: 244°–247° C. (dec.).

(12) Formic acid (1 ml) was added dropwise to acetic anhydride (2 ml), while stirring and ice-cooling. The mixture was stirred for an hour at ambient temperature. Subsequently, to the mixture was added 3-(N-methoxyamino)propylphosphonic acid (680 mg). The reaction mixture was stirred for 45 minutes and then concentrated under reduced pressure. The residue thus obtained was dissolved in 1N aqueous sodium hydroxide solution (4 ml) and then the solution was concentrated under reduced pressure to give a residue, which was dissolved in ethanol (50 ml). The solution was concentrated under reduced pressure to give a residue, which was pulverized with acetone to give powdery monosodium salt of 3-(N-formyl-N-methoxyamino)propylphosphonic acid (680 mg).

I.R. (Nujol): νmax: 3600–2300, 1660, 1280, 1230, 1050, 890 cm$^{-1}$.

| N.M.R. | |
|---|---|
| δ(ppm) in D$_2$O; | 1.3–2.3 (4H, m), |
| | 3.70 (2H, t, J = 6Hz), |
| | 3.72 (3H, s), |
| | 8.00 (s) ⎫ 1H |
| | 8.42 (s) ⎭ |

(13) To a mixture of 3-(N-hydroxyamino)propylphosphonic acid (1.64 g), water (16 ml) and acetone (16 ml) was added dropwise a solution of ethoxalyl chloride (2.75 g) in acetone (10 ml) under ice-cooling in the course of 45 minutes, while stirring. During this period, pH of the reaction mixture was kept at 7–8 with 5% aqueous sodium bicarbonate solution.

The stirring was continued for an additional hour, and then acetone was evaporated under reduced pressure. The residue thus obtained was adjusted to pH 1.8–2.0 with 10% hydrochloric acid and subjected to a column chromatography using activated charcoal. The object compound was eluted with 70% aqueous acetone. After acetone was evaporated under reduced pressure, the resulting solution was adjusted to pH 5.2 with 1N aqueous sodium hydroxide solution and concentrated under reduced pressure to give a residue, which was pulverized with acetone to give powdery monosodium salt of 3-(N-ethoxalyl-N-hydroxyamino)propylphosphonic acid.

I.R (Nujol): νmax: 3600–2500, 1730, 1640, 1300, 1250, 1130, 1010 cm$^{-1}$.

N.M.R.: δ (ppm) in D$_2$O: 1.32 (3H, t, J=Hz), 1.5–2.3 (4H, m), 3.75 (2H, t, J=6Hz), 4.48 (2H, quartet, J=7Hz).

(14) A mixture of 3-(N-hydroxyamino)propylphosphonic acid (820 mg), bis(trimethylsilyl)acetamide (5.0 g), triethylamine (1.01 g) and dichloromethane (40 ml) was stirred at ambient temperature for 2.5 hours. The reaction mixture was cooled to 0°–5° C. and mesyl chloride (1.15 g) was added dropwise with stirring. The reaction mixture was stirred for 1.25 hours and then concentrated under reduced pressure to give a residue, which was dissolved in water (50 ml). The solution was subjected to a column chromatography using activated charcoal. After the column was washed with water, the object compound was eluted with 70% aqueous acetone. The eluate was collected and evaporated to dryness to give powdery 3-(N-hydroxy-N-mesylamino)propylphosphonic acid (320 mg). This powder was dissolved in ethanol (20 ml). To the solution was added conc. aqueous ammonia (0.4 ml) to give precipitates, which were separated by filtration and dried to give crystalline monomammonium salt of 3-(N-hydroxy-N-mesylamino)propylphosphonic acid (220 mg). Mp 103°–105° C. (dec.).

I.R. (Nujol): νmax: 3600–2200, 1330, 1320, 1150, 1040, 1010, 960, 930, 890 cm$^{-1}$.

N.M.R.: δ(ppm) in D$_2$O: 1.4–2.2 (4H, m), 3.10 (3H, s), 3.28 (2H, t, J=6Hz).

(15) A mixture of 3-(N-hydroxyamino)propylphosphonic acid (1.64 g), bis(trimethylsilyl)acetamide (10.0 g) and dichloromethane (32 ml) was stirred for 3 hours at ambient temperature. To this mixture was added dropwise a solution of 2-acetoxy-4-chlorobenzoyl chloride (2.3 g) in dichloromethane (10 ml) with stirring under ice-cooling. The reaction mixture was stirred at the same temperature for 30 minutes and at ambient temperature for 1.5 hours. The mixture was concentrated under reduced pressure to give a residue, which was dissolved in ethyl acetate (80ml). The solution was washed with cold 5% hydrochloride acid (30 ml). The washings was extracted three times with ethyl acetate (30 ml). The combined ethyl acetate layer was washed with saturated aqueous sodium chloride solution (10 ml), dried over magnesium sulfate and evaporated to dryness to give a crude powder (4.35 g) of 3-[N-(2-acetoxy-4-chloro benzoyl)-N-hydroxyamino]propylphosphonic acid. This crude powder (1 g) was dissolved in a mixture of ethanol (30 ml) and conc. aqueous ammonia (8 ml). The solution was stirred at ambient temperature for 4 hours and then concentrated under reduced pressure to give a residue, which was dissolved in a small volume of ethanol. To the solution was added ether to give precipitates, which were separated by filtration and dried to give powdery monoammonium salt of 3-[N-(4-chloro-2-hydroxy benzoyl)-N-hydroxyamino]propylphosphonic acid (430 mg).

I.R. (Nujol): νmax: 3600–2200, 1600, 1280, 1110, 1030, 900, 820 cm$^{-1}$.

N.M.R.: δ (ppm) in D$_2$O; 1.4–2.2 (4H, m), 3.72 (2H, t, J=6Hz), 6.8–7.2 (3H, m).

(16) A mixture of 3-(N-hydroxyamino)propylphosphonic acid (1.64 g), bis(trimethylsilyl)acetamide (10 g) and dichloromethane (30 ml) was stirred at ambient temperature for 3 hours and cooled to 0°–5° C. To the mixture was added methylisothiocyanate (800 mg) under ice-cooling. The reaction mixture was stirred at the same temperature for an hour and concentrated under reduced pressure to give a residue. To this residue was added water (50 ml) and stirred at ambient temperature for 30 minutes. After the remaining dichloromethane was removed by evaporation under reduced pressure, an additional 50 ml of water was added. The aqueous solution was subjected to a column chromatography using activated charcoal. The column was washed with water (650 ml) and then the object compound was eluted with 70% aqueous acetone. The eluate was concentrated under reduced pressure to give crystals, which were separated by filtration, washed with ethanol and dried to give crystalline 3-[N-hydroxy-N-{(N-methyl)thiocarbamoyl}amino]propylphosphonic acid (320 mg). Further, the ethanol washing was concentrated under reduced pressure to give a residue which was pulverized to give the same object compound (450 mg). Mp 190°–194° C. (dec.).

I.R. (Nujol): $\nu$max: 3300, 3200—2300, 1560, 1350, 1285, 1175, 1020, 1010, 905 cm$^{-1}$.

N.M.R.: $\delta$(ppm) in D$_2$O; 1.3–2.3 (4H, m), 3.05 (3H, s), 4.10 (2H, t, J=6Hz).

(17) A mixture of 3-(N-hydroxyamino)propylphosphonic acid (1.64 g), dichloromethane (30 ml) and bis(trimethylsilyl)acetamide (10 g) was stirred at ambient temperature for 3 hours. The mixture was cooled to 0–5° C. and phenyl isocyanate (1.80 g) was added thereto. The reaction mixture was stirred at the same temperature for an hour and at ambient temperature for 3 hours and then allowed to stand overnight. The resultant mixture was concentrated under reduced pressure. To the residue was added water (60 ml), and then the mixture was stirred at ambient temperature for 3 hours. Insoluble materials were removed by filtration and the filtrate was washed twice with ethyl acetate (50 ml). To the aqueous layer was added an additional 90 ml of water, whereafter the aqueous solution was subjected to a column chromatography using activated charcoal. The object compound was eluted with 70% aqueous acetone. The eluate was evaporated to dryness under reduced pressure, whereafter the resulting crystals were washed with acetone and dried to give crystalline 3-(N-hydroxy-N-phenylcarbamoylamino)propylphosphonic acid (1.13 g). Mp 126–130° C. (dec.)

I.R. (Nujol): $\nu$max: 3370, 3300–2200, 1610, 1590, 1550, 1285, 1230, 1200, 1075, 995, 940 cm$^{-1}$.

N.M.R.: $\delta$(ppm) in D$_2$O; 1.6–2.2 (4H, m), 3.69 (2H, t, J=7Hz), 7.43 (5H, s).

(18) A solution of methyl chlorocarbonate (3 g) in acetone (10 ml) was added dropwise to a mixture of 3-(N-hydroxyamino)propylphosphonic acid (1.64 g), water (16 ml) and acetone (16 ml in the course of 30 minutes under ice-cooling, while stirring. During this period, pH of the mixture was kept at around 7–8 with 5% aqueous sodium bicarbonate solution.

The stirring was continued at the same temperature for an additional hour, and then acetone was evaporated under reduced pressure. The resulting aqueous solution was adjusted to pH 2 with 10% hydrochloric acid and then subjected to a columm chromatography using activated charcoal. The object compound was eluted with 70% aqueous acetone. After removal of acetone by evaporation under reduced pressure, the resulting aqueous solution was adjusted to pH 5.0 with 1N aqueous sodium hydroxide solution and then concentrated under reduced pressure. The residue was dissolved in methanol (40 ml) and refluxed for 4 hours. The methanol solution was evaporated to dryness to give powdery sodium salt of 3-(N-hydroxy-N-methoxycarbonylamino)propylphosphonic acid (320 mg).

I.R. (Nujol): $\nu$max: 3600–2200, 1700, 1265, 1170, 1060, 900, 820 cm$^{-1}$.

N.M.R.: $\delta$(ppm) in D$_2$; 1.4–2.1 (4H, m), 3.63 (2H, t, J=6Hz), 3.76 (3H, s).

(19) A mixture of 3-(N-hydroxyamino)propylphosphonic acid (1.64 g), potassium isocyanate (2.43 g) and water (17 ml) was stirred at ambient temperature for 3 hours, while maintaining the pH at around 5–7 with 3N hydrochloric acid. The reaction mixture was adjusted to pH 9 with 1N aqueous sodium hydroxide solution and then stirred at ambient temperature for 20 minutes. The resultant mixture was adjusted to pH 1.8 with 3N hydrochloric acid and concentrated under reduced pressure. The residue was extracted with methanol and the extract was concentrated under reduced pressure to give crude 3-(N-carbamoyl-N-hydroxyamino)propylphosphonic acid (2.50 g). A part (1 g) of the object compound was dissolved in water (5 ml), and the solution was passed through a column of nonionic adsorption resin Diaion HP 20 (trade name, made by Mitsubishi Chemical Industries). The object compound was eluted with water. The fractions containing the object compound was collected and evaporated to dryness to give powdery 3-(N-carbomoyl-N-hydroxyamino)propylphosphonic acid (410 mg).

N.M.R.: $\delta$(ppm) in D$_2$O; 1.4–2.1 (4H, m), 3.53 (2H, t, J=6Hz).

(20) To a stirring mixture of 3-(N-hydroxyamino)propylphosphonic acid (1.64 g), water (12 ml) and acetone (12 ml) was added a solution of succinic anhydride (2.5 g) in acetone (10 ml). The mixture was stirred at ambient temperature for 3 hours, whereafter succinic anhydride (1.5 g) was added thereto and the mixture was stirred for an hour. After concentration of the reaction mixture under reduced pressure, the resulting residue was washed three times with acetone (50 ml) and treated with a column of activated charcoal. The object compound was eluted with 70% aqueous acetone. The eluate was concentrated under reduced pressure to give a residue (720 mg), which was dissolved in 1N aqueous sodium hydroxide solution (2.8 ml). The solution was evaporated to dryness to give a residue, which was pulverized with ethanol to give powdery 3-[N-3-carboxypropionyl)-N-hydroxyamino]propylphosphonic acid (650 mg).

I.R. (Nujol): $\nu$max: 3600–2400, 1710, 1620, 1250, 1140, 1030, 890 cm$^{-1}$.

N.M.R.: $\delta$(ppm) in D$_2$O; 1.4–2.2 (4H, m), 2.5–2.9 (4H, m), 3.73 (2H, t, J=7Hz).

(21) Formic acid (4.5 ml) was added dropwise to acetic anhydride (9.4 ml) at 15–20° C. in the course of 3 minutes with stirring. After stirring was continued at the same temperature for 30 minutes, 3-(N-hydroxyamino)propylphosphonic acid (7.75 g) was added, and the mixture was stirred at the same temperature for 1.5 hours. To the resultant mixture was added benzene (100 ml), whereafter the mixture was stirred for 10 minutes to precipitate an oil. The oil was separated by decantation, washed twice with benzene (50 ml) and then dissolved in water (25 ml). To this aqueous solution was added calcium carbonate (2.37 g) at 15–20° C., while stirring.

After the resultant aqueous solution was treated with activated charcoal, the filtrate was triturated with methanol (300 ml) at 0–5° C. to give precipitates. After stirred for 30 minutes, the precipitates was collected by decantation and dissolved in water (25 ml). A small volume of insoluble materials was removed by filtration, whereafter, to the filtrate was added dropwise methanol (300 ml) with stirring at 0–5° C. to give precipitates. After the stirring was continued for an hour, the precipitates was collected by filtration, washed with methanol (20 ml) and dried over phosphorus pentoxide under reduced pressure to give powdery calcium bis[3-(N-formyl-N-hydroxyamino)propylphosphonate] (3.72 g).

I.R. (Nujol): $\nu$max: 3600–2200, 1660, 1230, 1190, 1100, 1050, 920 cm$^{-1}$.

| N.M.R. | |
|---|---|
| $\delta$(ppm) in D$_2$O; | 1.3–2.4 (4H, m) |
| | 3.70 (2H, t, J = 6Hz), |
| | 8.00 (s) ⎫ |
| | 8.40 (s) ⎭ 1H |

(22) Formic acid (1.67 g.) was added to acetic anhydride (1.86 g.) at ambient temperature with stirring. The stirring was continued at ambient temperature for 30 minutes, and then to the mixture was added a solution of 3-(N-hydroxyamino)trans-1-propenylphosphonic acid (2.14 g.) in formic acid (7 ml.). The reaction mixture was stirred at ambient temperature for 1.5 hours and concentrated under reduced pressure to give a residue, to which was added methanol (20 ml.). Insoluble materials were removed by filtration and to the filtrate was added a methanol solution (3 ml.) of potassium hydroxide (780 mg.) to give crystals. The crystals were separated by filtration and dried to give crystalline monopotassium salt of 3-(N-formyl-N-hydroxyamino)-trans-1-propenylphosphonic acid (0.76 g.). The same object compound (0.73 g.) was recovered from the mother liquor. M.p. 178–180° C. (dec.).

I.R. (Nujol): $\nu$max=1665, 1250 cm$^{-1}$.

| N.M.R. | |
|---|---|
| $\delta$(ppm) in D$_2$O: | 4.30 (2H, m) |
| | 6.01 (1H, m) |
| | 6.38 (1H, m) |
| | 8.02 (s) ⎫ |
| | 8.38 (s) ⎭ 1H |

(23) Formic acid (2 ml.) was added dropwise to acetic anhydride (2.45 ml.) at ambient temperature with stirring. After the stirring was continued at the same temperature for 30 minutes, 3-(N-hydroxyamino)propylphosphonic acid (3.10 g.) was added to the mixture. The reaction mixture was stirred at ambient temperature for an hour and then concentrated under reduced pressure to give an oily residue, which was dissolved in water (25 ml.). To the aqueous solution was added dropwise a solution of diacetic acid salts of N,N'-dibenzylethylenediamine (3.60 g.) in water (15 ml.) under ice-cooling and with stirring. The resultant mixture was concentrated under reduced pressure to give an oily residue, which was dissolved in water (30 ml.). The aqueous solution was concentrated under reduced pressure to give an oily residue, which was dissolved in water (30 ml.). The aqueous solution was concentrated under reduced pressure to give an oily residue, which was crystallized with a mixture of methanol (30 ml.) and ethanol (40 ml.). The crystals were separated by filtration, washed with ethanol (20 ml.) and then dried to give crystals (3.34 g.). The same crystals (1.00 g.) were recovered from the filtrte and the washings by concentrating them under reduced pressure to a volume of 40 ml. and allowing the concentrate to stand overnight at 4° C. A part (3 g.) of the combined crystals, as obtained above, was recrystallized from a mixture of water and ethanol (1:6) (40 ml.) to give N,N'-dibenzylethylenediamine bis[3-(N-formyl-N-hydroxyamino)propylphosphonate] (2.60 g.) in the form of needles.

M.p. 155–157° C. (dec.)

I.R. (Nujol): $\nu$max: 3400–2200, 1665, 1220, 1110, 1020, 925 cm$^{-1}$.

| N.M.R. | |
|---|---|
| $\delta$(ppm) in D$_2$O: | 1.3–2.1 (4H, m) |
| | 3.53 (2H, s) |
| | 3.55 (2H, t, J = 6Hz) |
| | 4.30 (2H, s) |
| | 7.53 (5H, s) |
| | 7.90 (s) ⎫ |
| | 8.28 (s) ⎭ 1H |

(24) Formic acid (1.19 g.) was added dropwise to acetic anhydride (1.33 g.) at ambient temperature with stirring. After the stirring was continued at the same temperature for 30 minutes, 5-(N-hydroxyamino)pentylphosphonic acid (1.83 g.) was added to the mixture. The reaction mixture was stirred at ambient temperature for an hour and 45 minutes, and then concentrated under reduced pressure to give an oily residue. The residue was dissolved in ethanol (30 ml) and to the solution was added dropwise conc. aqueous ammonia (2 ml.) to give crystals. After the mixture containing crystals was stirred at ambient temperature for an hour, the crystals were separated by filtration and dried to give crystalline monoammonium salt of 5-(N-formyl-N-hydroxyamino)pentylphosphonic acid (2.10 g.). A part (1.8 g.) of the crystals was dissolved in water (6 ml.) to give insoluble materials, which were removed by filtration and washed with water. The filtrate and the washings were combined and ethanol (30 ml.) was added thereto under heating at 60° C. to give purified crystals (1.62 g) of the same compound as mentioned above.

M.p. 170–175° C. (dec.).

I.R. (Nujol): $\nu$max: 3600–2200, 1635, 1190, 1100, 1045, 1015, 945 cm$^{-1}$.

| N.M.R. | |
|---|---|
| $\delta$(ppm) in D$_2$O: | 1.1–2.0 (8H, m) |
| | 3.55 (2H, t, J = 6Hz) |
| | 7.95 (s) ⎫ |
| | 8.30 (s) ⎭ 1H |

(25) Formic acid (1.5 ml.) was added dropwise to acetic anhydride (530 mg.) at ambient temperature with stirring. The stirring was continued at the same temperature for 30 minutes, and then to the mixture were added 2-(N-hydroxyamino)ethylphosphonic acid (564 mg.). The reaction mixture was stirred at ambient temperature for 2 hours and concentrated under reduced pressure to give an oily residue. The residue was dissolved in methanol (10 ml.) to give a small volume of insoluble materials, which were removed by filtration. To the filtrate was added dropwise a solution of potassium hydroxide in methanol (2 ml.). The mixture was stirred for 30 minutes to give crystals, which were separated by filtration and washed twice with methanol (5 ml.) to give crystalline monopotassium salt of 2-N-formyl-N-hydroxyamino)ethylphosphonic acid (630 mg.).

M.p. 201–203° C. (dec.)

I.R. (Nujol): νmax: 3600–2200, 1650, 1280, 1250, 1230, 1160, 1100, 1020, 920, 880, 795 cm$^{-1}$.

| N.M.R. | |
|---|---|
| δ(ppm) in D$_2$O: | 1.7–2.4 (2H, m) |
| | 3.6–4.2 (2H, m) |
| | 8.00 (s) ⎫ |
| |         ⎬ 1H |
| | 8.31 (s) ⎭ |

(26) Formic acid (2.0 ml.) was added dropwise to acetic anhydride (2.45 g.) at ambient temperature with stirring. After the stirring was continued at the same temperature for 30 minutes, 3-(N-hydroxyamino)-propylphosphonic acid (3.10 g.) was added to the mixture. The reaction mixture was stirred for an hour and concentrated under reduced pressure to give a residue, which was dissolved in water (25 ml.) To the aqueous solution was added ethylenediamine (0.60 g.). The mixture was concentrated under reduced pressure to give a residue, which was dissolved in water. The aqueous solution was concentrated under reduced pressure to give a residue, and to the residue was added ethanol (30 ml.) to give crystals. The crystals were separated by filtration and washed twice with ethanol (10 ml.) to give crystalline ethylendiamine bis[3-(N-formyl-N-hydroxyamino)propylphosphonate] (3.95 g.), a part (3 g.) of which was recrystallized from 90% aqueous methanol to give needles (1 g.) of the same object compound.

M.p. 112°–118° C.

I.R. (Nujol): νmax=3600–2000, 1630, 1200, 1120, 1010, 910 cm$^{-1}$.

| N.M.R. | |
|---|---|
| δ(ppm) in D$_2$O: | 1.3–2.1 (4H, m) |
| | 3.36 (2H, s) |
| | 3.62 (2H, t, J = 6Hz) |
| | 7.96 (s) ⎫ |
| |         ⎬ 1H |
| | 8.32 (s) ⎭ |

(27) Formic acid (1.0 ml.) was added dropwise to acetic anhydride (1.2 ml.) at ambient temperature with stirring. The stirring was continued at the same temperature for 30 minutes and then 3-(N-hydroxyamino)-propylphosphonic acid (1.51 g.) was added to the mixture. The reaction mixture was stirred at ambient temperature for 1.5 hours and concentrated under reduced pressure to given an oily residue, which was dissolved in ethanol (20 ml.). To the aqueous solution was added ethanolamine (0.61 g.) to precipitate an oil, which was separated by decantation and crystallized with ethanol (20 ml.) to give crystals. The crystals were separated by filtration, washed with ethanol and dried to give crystalline monoethanolamine salt of 3-(N-formyl-N-hydroxyamino)propylphosphonic acid (1.75 g.), a part (1.5 g.) of which was recrystallized from 90% aqueous ethanol to give the purified object compound (1.15 g). M.p. 139°–142° C.

I.R. (Nujol): νmax: 3600–2200, 3190, 1660, 1190, 1100, 1035, 1020, 925, 880 cm$^{-1}$.

| N.M.R. | |
|---|---|
| δ(ppm) in D$_2$O: | 1.3–2.1 (4H, m) |
| | 3.10 (2H, t, J = 5Hz) |
| | 3.60 (2H, t, J = 6Hz) |
| | 3.80 (2H, t, J = 5Hz) |
| | 7.96 (s) ⎫ |
| |         ⎬ 1H |
| | 8.32 (s) ⎭ |

(28) To a suspension of 2-(N-hydroxyamino)ethyl-phosphonic acid (564 mg.) in water (3 ml.) was added dropwise acetic anhydride (820 mg.) at ambient temperature. The reaction mixture was stirred at the same temperature and concentrated under reduced pressure to give an oily residue. The residue was dissolved in water (5 ml.) and the aqueous solution was concentrated under reduced pressure to give a residue. This operation was repeated twice. Subsequently, the residue obtained was dissolved in 1 N aqueous sodium hydroxide solution (4 ml.). The aqueous solution was concentrated under reduced pressure to give precipitates, which were pulverized with ethanol to give crude powder. The crude powder was dissolved in water (10 ml.) and the aqueous solution was heated at 100°–110° C. for an hour and concentrated under reduced pressure to give precipitates, which were pulverized with ethanol to give crystalline monosodium salt of 2-(N-acetyl-N-hydroxyamino)ethylphosphonic acid (380 mg.).

M.p. 185°–192° C. (dec.)

(I.R. (Nujol): νmax: 3600–2200, 1620, 1230, 1160, 1040, 940, 890, 810 cm$^{-1}$.

N.M.R.: δ(ppm) in D$_2$O: 1.6–2.3 (2H, m), 2.12 (3H, s), 3.5–4.1 (2H, m).

(29) Formic acid (2.0 g.) was added to acetic anhydride (3.5 g.) under ice-cooling with stirring. The mixture was stirred at ambient temperature for 30 minutes and added, under ice-cooling, to a solution of hydrochloric acid salt of 3-(N-hydroxyamino)-2-methylpropylphosphonic acid (4.7 g.) in water (10 ml.) which was adjusted to pH 4.0 with aqueous potassium hydroxide solution. The reaction mixture was stirred at ambient temperature for 30 minutes and then concentrated under reduced pressure to give a residue, which was dissolved in water (20 ml.). To the solution was added dropwise a solution of potassium hydroxide (1.3 g.) in water (10 ml.). The mixture was concentrated under reduced pressure to give a residue, which was dissolved in water (20 ml.) and then the solution was concentrated under reduced pressure to give a residue. The residue was subjected to a column chromatography on cellulose (volume of cellulose: 600 ml., developing solvent: 70% aqueous isopropylalcohol). The eluate was concentrated under reduced pressure to give an oily residue, which was crystallized from a mixture of methanol and ethanol (1:10) to give crystalline monopotassium salt of 3-(N-formyl-N-hydroxyamino)-2-methylpropyl-phosphonic acid (0.95 g.). M.p. 128°–131° C. (dec.)

| N.M.R. | |
|---|---|
| | 1.04 (3H, d, J = 6Hz) |
| | 1.60 (2H, m) |
| | 2.26 (1H, m) |
| | 3.50 (2H, d, J = 6Hz) |
| | 8.00 (s) ⎫ |
| |         ⎬ 1H |
| | 8.39 (s) ⎭ |

(30) A solution of monosodium salt of 3-(N-ethoxalyl-N-hydroxyamino)propylphosphonic acid (277 mg) in a mixture of water (3 ml) and 1N aqueous sodium hydroxide solution (2 ml) was stirred at ambient temperature for 4 hours. The reaction mixture was neutralized with 1N hydrochloric acid (1 ml) and evaporated to dryness under reduced pressure. The residue was extracted with methanol (25 ml). The extract was evaporated to dryness under reduced pressure to give powdery disodium salt of 3-(N-hydroxy-N-oxaloamino)propylphosphonic acid (250 mg).

I.R. (Nujol): νmax: 3600–2100, 1620, 1280, 1225, 1150, 1030, 900 cm$^{-1}$.

N.M.R. δ(ppm) in D$_2$O; 1.30–2.30 (4H, m), 3.72 (2H, t, J=7 Hz).

(31) Formic acid (300 mg.) was added dropwise to acetic anhydride (330 mg.) with stirring and the mixture was stirred for half an hour. To this solution were added 2-hydroxy-3-(N-hydroxyamino)propylphosphonic acid (430 mg.) and then formic acid (0.5 ml.), and the mixture was stirred for 1.5 hours at ambient temperature and then evaporated to dryness under reduced pressure. The oily residue was dissolved in methanol (10 ml.) and adjusted to pH 6-7 with conc. aqueous ammonium hydroxide solution to give oily precipitates which was collected by decantation and pulverized by triturating with methanol to give monoammonium salt of 3-(N-formyl-N-hydroxyamino)-2-hydroxypropylphosphonic acid (80 mg.).

I.R. (Nujol): νmax: 3700–2200, 1620, 1160, 1000 cm$^{-1}$.

| N.M.R. | |
|---|---|
| δppm in D$_2$O; | 1.72, 1.92 (2H, d, d, J = 6Hz, 17Hz) |
| | 3.4–3.8 (2H, m) |
| | 4.2 (1H, m) |
| | 7.90 (s) ⎫ 1H |
| | 8.32 (s) ⎭ |

(32) An oily 3-(N-formyl-N-hydroxyamino)propylphosphonic acid (12.05 g.), which was prepared by the reaction of 3-(N-hydroxyamino)propylphosphonic acid (15.5 g.), acetic anhydride (12.3 g.) and formic acid (9.8 ml.) conducted in substantially the same manner as that of Example (31), was dissolved in water (80 ml.) and treated with magnesium hydroxide (5.83 g.) for 15 minutes under ice-cooling with stirring.

The mixture was filtered and about half of the filtrate was evaporated to dryness under reduced pressure. The oily residue was pulverized by triturating with ethanol (60 ml.) to give magnesium salt of 3-(N-formyl-N-hydroxyamino)propyl phosphonic acid (12.05 g.), m.p.>250° C.

I.R. (Nujol): νmax: 3700–2300, 1660, 1100, 1005 cm$^{-1}$.

(33) Monoethyl 3-(N-formyl-N-hydroxyamino)-propylphosphonate (0.86 g.) was obtained by reacting monoethyl 3-(N-hydroxyamino)propylphosphonate (0.92 g.) with a mixture of acetic anhydride (0.66 g.) and formic acid (0.60 g.) in substantially the same manner as that of Example (31) for 2 hours, evaporating to dryness under reduced pressure and crystallization from ethanol.

| N.M.R. | |
|---|---|
| δppm in D$_2$O: | 1.30 (3H, t, J = 7Hz) |
| | 1.47–2.30 (4H, m) |
| | 3.65 (2H, t, J = 6Hz) |
| | 4.08 (2H, m) |
| | 7.99 (s) ⎫ 1H |
| | 8.30 (s) ⎭ |

(34) 3-(N-Hydroxyamino)propylphosphonic acid (31.0 g.) was added to a mixture of acetic anhydride (24.6 ml.) and formic acid (19.6 ml.), which was prepared in the same manner as that of Example (31), and stirred for 1 hour at ambient temperature. The reaction mixture was stirred for 20 minutes by adding benzene (400 ml.) to give oily precipitates which were collected by decantation and washed with benzene (200 ml.) by decantation. The oily product was dissolved in water (120 ml.), treated with calcium oxide (11.2 g.) for 15 minutes under ice-cooling and filtered. The filtrate was carefully adjusted to pH 7 with 20% aqueous sodium hydroxide solution under ice-cooling and allowed to stand overnight at ambient temperature to give crystals of monocalcium salt of 3-(N-formyl-N-hydroxyamino)-propylphosphonic acid (34.6 g.), m.p.>250°.

I.R. (Nujol): νmax: 3700–2500, 1650, 1320, 1265, 1220, 1145, 1060, 980, 895 cm$^{-1}$.

An additional crystal of the same mono calcium salt (9.6 g.) was recovered from the mother liquor by condensing to about half of its original volume.

(35) An oily 3-(N-formyl-N-hydroxyamino)propylphosphonic acid was obtained from 3-(N-hydroxyamino)propylphosphonic acid (9.30 g.) and a mixture of acetic anhydride (7.4 ml.) and formic acid (6.0 ml.) in substantially the same manner as that of Example (34). This oil was dissolved in water (70 ml.) to form a clear solution (81 ml.), of which an aliquot (27 ml.) was mixed with a solution of arginine (3.48 g.) in water (30 ml.) and evaporated to dryness under reduced pressure. The residue was triturated with ethanol (50 ml.) to give solid arginine salt of 3-(N-formyl-N-hydroxyamino)propylphosphonic acid (6.76 g.).

I.R. (Nujol): νmax: 3700–2200, 1640, 1160, 1030 cm$^{-1}$.

(36) To a mixture of 3-(N-hydroxyamino)propylphosphonic acid (0.775 g.), sodium bicarbonate (0.84 g.), water (5 ml.) and acetone (5 ml.) was added dropwise a solution of methoxyacetyl chloride (1.05 g.) in anhydrous acetone (5 ml.) with stirring under ice-cooling. The reaction mixture was stirred for 30 minutes at the same temperature, adjusted to pH 9.0 with 1 N aqueous sodium hydroxide solution and then stirred for 1 hour at ambient temperature. After adjusting to pH 3.0 with 10% hydrochloric acid, the mixture was evaporated to dryness under reduced pressure. The oily residue was washed twice with ethyl acetate (each 10 ml. portion) by decantation and dissolved in water (50 ml.). The aqueous solution was adjusted to pH 15 with 10% hydrochloric acid and passed through a column packed with activated charcoal (50 ml.). The column was washed with 70% aqueous acetone, and the effluent and washings were combined and evaporated to dryness under reduced pressure. The oily residue was dissolved in small amount of water, adjusted to pH 5.0 with 1 N aqueous sodium hydroxide solution and evaporated to dryness to give monosodium salt of 3-(N-hydroxy-N-methoxyacetylamino)propylphosphonic acid (0.4 g.).

N.M.R.: δppm in D$_2$O: 1.36–2.08 (4H, m), 3.40 (3H, s), 3.64 (2H, t, J=6Hz), 4.36 (2H, s).

(37) To a solution of diethyl 3-(N-hydroxyamino)-propylphosphonate (2.80 g.) in chloroform (30 ml.) was added dropwise a mixture of acetic anhydride (2.04 g.) and formic acid (1.38 g.), which was prepared in the same manner as that of Example (31), under ice-cooling with stirring. The reaction mixture was stirred for half an hour at 0°-5° C. and for additional an hour at ambient temperature, and then evaporated to dryness under reduced pressure to give an oily residue, which was dissolved in a mixture of methanol (15 ml.) and water (5 ml.), adjusted to pH 8 with 1N aqueous sodium hydroxide solution and stirred for 1.5 hours at ambient temperature. The methanol was distilled off from this solution under reduced pressure to give an aqueous solution, which was adjusted to pH 5 with 10% hydrochloric acid and extracted with chloroform (once with 30 ml. portion and three times with 10 ml. portions). These combined extracts were dried over magnesium sulfate and evaporated to dryness under reduced pressure to give crude diethyl 3-(N-formyl-N-hydroxyamino)-propylphosphonate (2.89 g.), which was passed through a column packed with silica gel (60 g.). The column was eluted with a mixture of chloroform and methanol (25:1 by volume), and the fractions containing an object compound were collected and evaporated to dryness under reduced pressure to give the same pure object compound (1.71 g.).

I.R. (liquid film): $\nu$max: 3500 (broad), 1620, 1200, 1030 cm$^{-1}$.

| N.M.R. | |
|---|---|
| $\delta$ppm in CDCl$_3$: | 1.36 (6H, t, J = 7Hz) |
| | 1.5-2.4 (4H, m) |
| | 3.72 (2H, t, J = 6Hz) |
| | 4.15 (4H, m) |
| | 7.30 (s) ⎫ |
| | 7.95 (s) ⎭ 1H |

(38) A solution of phenoxyacetyl chloride (3.4 g.) in dried acetone (10 ml.) was added dropwise to a solution of 3-(N-hydroxyamino)propylphosphonic acid (1.51 g.) in mixture of 1 N aqueous sodium hydroxide solution (30 ml.) and acetone (20 ml.) under ice-cooling in the course of 10 minutes, and the mixture was stirred for an hour at the same temperature, and then adjusted to pH 10 with 1 N aqueous sodium hydroxide solution. The acetone was distilled off from the reaction mixture, and the remaining aqueous solution was adjusted to pH 2.0 with 10% hydrochloric acid, washed with ethyl ether, and then adjusted to pH 1.0 with 10% hydrochloric acid and saturated with sodium chloride. This solution was extracted twice with ethyl acetate (each 100 ml. portion) (insoluble materials (0.2 g.) produced at this stage were collected by filtration) and the combined extracts were dried over magnesium sulfate and evaporated to dryness under reduced pressure to give 3-(N-hydroxy-N-phenoxyacetylamino)propylphosphonic acid (0.1 g.). Insoluble materials produced above were identified with the same object compound.

Total yield was 0.3 g.

N.M.R. $\delta$ppm in CD$_3$OD: 1.37-2.40 (4H, m), 3.74 (2H, t, J=6Hz), 4.90 (2H, s), 6.73-7.54 (5H, m).

(39) To N,N-dimethylformamide (0.80 g.) was added thionyl chloride (1.80 g.), and the mixture was stirred for half an hour at 50° C. and then the unreacted thionyl chloride was removed. To the residue was added a small amount of methylene chloride and evaporated to dryness under reduced pressure. To the residue thus obtained were added methylene chloride (50 ml.) and crotonic acid (0.85 g.) at −30° C. and the mixture was stirred for half an hour at the same temperature. To this solution was added a solution of 3-(N-hydroxyamino)-propylphosphonic acid (1.55 g.) and N,O-bis(trimethylsilyl)acetamide (10 g.) in methylene chloride (30 ml.) at −40° C. After the mixture was stirred for half an hour at the same temperature, the temperature was gradually elevated to 0° C. and the mixture was stirred for 2 hours. The reaction mixture was evaporated to dryness under reduced pressure to give a residue, which was dissolved in water (30 ml.), washed twice with ethyl acetate (each 30 ml. portion) and evaporated to dryness under reduced pressure. The resultant oily residue was washed with ethyl acetate, dissolved in ethanol (15 ml.) and then adjusted to pH 4.0 with an ethanolic potassium hydroxide to precipitate crystals. These crystals were collected by filtration, washed with a small amount of ethanol and dried to give monopotassium salt of 3-(N-crotonoyl-N-hydroxyamino)propylphosphonic acid (0.91 g.).

N.M.R.: $\delta$ppm in D$_2$O: 1.26-2.30 (4H, m), 1.88 (3H, d, J=6 Hz), 3.74 (2H, t, J=6 Hz), 6.24-7.20 (2H, m).

(40) Monoammonium salt of 3-[N-hydroxy-N-(2-phenylglycoloyl)amino]propylphosphonic acid was obtained by reacting 3-(N-hydroxyamino)propylphosphonic acid with 2-phenylglycolic acid, N,N-dimethylformamide and thionyl chloride, in substantially the same manner as that of Example (39) and then by treating the resultant compound with 28% aqueous ammonia.

N.M.R.: $\delta$ppm in D$_2$O: 1.40-2.14 (4H, m), 3.68 (2H, t, J=6 Hz), 5.70 (1H, s), 7.46 (5H, s).

(41) To a suspension of 2-(2,2-dichloroacetoxyimino)-2-phenylacetic acid (3.06 g.) in methylene chloride (20 ml.) was added phosphorus pentoxide (2.28 g.) under ice-cooling, and the mixture was stirred for 20 minutes at the same temperature and then evaporated to dryness under reduced pressure to give a residue, which was dissolved in methylene chloride (10 ml.). This solution was added dropwise to a solution of 3-(N-hydroxyamino)propylphosphonic acid (1.55 g.) and N,O-bis(-trimethylsilyl)acetamide (10 g.) in methylene chloride (30 ml.) at −30° to −40° C. in the course of 5 minutes, whereafter the mixture was stirred for half an hour at the same temperature and for additional an hour at 0° C. the reaction mixture was evaporated to dryness under reduced pressure to give an oily residue, which was dissolved in water (30 ml.), stirred for 20 minutes, saturated with sodium chloride, and extracted five times with ethyl acetate (each 20 ml.) and three times with n-butanol (each 30 ml.). These extracts were evaporated to dryness under reduced pressure to give an oily residue (4.5 g.), which was dissolved in water (40 ml.). This aqueous solution was passed through a column packed with activated charcoal (100 ml.), and elution was conducted with water and then 30% aqueous acetone. The fractions containing an object compound were collected and evaporated to dryness under reduced pressure to give an oil (1.4 g.), which was dissolved in methanol and adjusted to pH 7 with 28% aqueous ammonia. The precipitates were collected by filtration and dried to give monoammonium salt of 3-[N-hydroxy-N-(2-hydroxyimino-2-phenylacetyl)amino]propylphosphonic acid (1.30 g.).

| N.M.R. | |
|---|---|
| δppm in D₂O: | 1.07-2.03 (4H, m) |
| | 3.54 (t, J = 6Hz) ⎫ |
| | ⎬ 2H |
| | 3.88 (t, J = 6Hz) ⎭ |
| | 7.55 (5H, s) |

(42) 3-[N-Hydroxy-N-{2-(1H-tetrazol-1-yl)acetyl}-amino]propylphosphonic acid (1.75 g.) was obtained by reacting 3-(N-hydroxyamino)propylphosphonic acid (1.55 g.) with 2-(1H-tetrazol-1-yl)acetyl chloride (2.22 g.) in methylene chloride (30 ml.) in substantially the same manner as that of Example (41). M.p. 157°-159° C.

| N.M.R. | |
|---|---|
| δppm in D₂O: | 1.47-2.36 (4H, m) |
| | 3.78 (2H, t, J = 6Hz) |
| | 5.72 (2H, s) |
| | 9.30 (1H, s) |

(43) Monoammonium salt of 3-(N-hydroxy-N-nicotinoylamino)propylphosphonic acid (1.3 g.) was obtained by reacting 3-(N-hydroxyamino)propylphosphonic acid (0.775 g.) with nicotinoyl chloride (1.23 g.) in methylene chloride (15 ml.) in substantially the same manner as that of Example (41), and by passing the resultant compound through a column packed with anion-exchange resin Amberlite IR-45 (Trademark, maker; Rohm & Haas Co.) (20 ml.) and eluting with 1N aqueous ammonia.

N.M.R.: δppm in D₂O: 1.37-2.40 (4H, m), 3.84 (2H, t, J=6 Hz), 7.62 (1H, d, d, J=8 Hz, 5 Hz), 8.14 (1H, double t; J=7 Hz, 1 Hz), 8.46-9.10 (2H, m).

(44) (a) 3-(N-Hydroxy-N-phenylglyoxyloylamino)-propylphosphonic acid was obtained by reacting 3-(N-hydroxyamino)propylphosphonic acid (1.55 g.) with phenylglyoxyloyl chloride (1.72 g.) in methylene chloride (40 ml.) in substantially the same manner as that of Example (41).

This compound was dissolved in ethanol (13 ml.), adjusted to pH 7.0 with 28% aqueous ammonia under ice-cooling and allowed to stand to give monoammonium salt of the same object compound (1.94 g.).

N.M.R.: δppm in D₂O: 1.36-2.08 (4H, m), 3.88 (2H, t, J=6 Hz), 7.36-8.08 (5H, m).

(b) To a solution of monoammonium salt of 3-(N-hydroxy-N-phenylglyoxyloylamino)propylphosphonic acid (0.32 g.) in water (9 ml.) was added sodium borohydride (0.04 g.) under ice-cooling, whereafter the mixture was stirred for an hour at ambient temperature. The reaction mixture was adjusted to pH 1.0 with 10% hydrochloric acid and then evaporated to dryness under reduced pressure. To the resultant residue was added ethanol (7 ml.) and the insoluble materials were removed by filtration. The filtrate was evaporated to dryness under reduced pressure and the remaining oily residue was dissolved in ethanol (10 ml.), adjusted to pH 7.0 with 28% aqueous ammonia solution and then evaporated to dryness under reduced pressure to give oily monoammonium salt of 3-[N-hydroxy-N-(2-phenylglycoloyl)amino]propylphosphonic acid (0.29 g.).

N.M.R.: δppm in D₂O: 1.40-2.14 (4H, m), 3.68 (2H, t, J=6 Hz), 5.70 (1H, s), 7.46 (5H, s).

(45) To a suspension of 2-hydroxy-3-(N-hydroxyamino)propylphosphonic acid (855 mg.) in water (4 ml.) was added acetic anhydride (1.02 g.) under ice-cooling, and the reaction mixture was stirred for 15 minutes at the same temperature. The reaction mixture was evaporated to dryness under reduced pressure to give a residue, which was dissolved in water (3 ml.) and adjusted to pH 10 with 28% aqueous ammonia, whereafter the aqueous solution was stirred for 3 hours at ambient temperature. This aqueous solution was adjusted to pH 2 with 1N hydrochloric acid and passed through a column of activated charcoal (50 ml.). The column was washed with water, and then elution was conducted with 80% aqueous acetone (200 ml.) to give an oily residue (400 mg.), which was dissolved in methanol (5 ml.). To this methanolic solution were added sodium hydroxide (80 mg.) in methanol (3 ml), and then ethanol to give powder. This powder was collected by filtration and dried to give monosodium salt of 3-(N-acetyl-N-hydroxyamino)-2-hydroxypropylphosphonic acid (230 mg.).

I.R. (Nujol): νmax: 1630, 1140 cm⁻¹.

N.M.R.: δppm in D₂O: 1.88 (2H, d, d, J=6 Hz, 18 Hz), 2.16 (3H, s), 3.65-3.90 (2H, m), 4.30 (1H, m).

(46) To a suspension of 3-(N-hydroxyamino)-trans-1-propenylphosphonic acid (1.53 g.) in water (7 ml.) was added dropwise acetic anhydride (2.04 g.), and the mixture was stirred for half an hour at ambient temperature, and evaporated to dryness under reduced pressure to give a residue, to which were added water (20 ml.) and then 1N aqueous potassium hydroxide solution (10 ml.) under ice-cooling. The mixture was heated for an hour at 100° C. and evaporated to dryness under reduced pressure to give a pale brown oil (1.68 g.), to which were added methanol (7 ml.) and acetone (2 ml.). Insoluble materials were filtered off and the filtrate was adjusted to pH 1 with 1N hydrochloric acid, passed through a column packed with activated charcoal (50 ml.). The column was washed with water (200 ml.) and eluted with 80% aqueous acetone (70 ml.). The effluent was adjusted to pH 5.6 with 1N potassium hydroxide solution and evaporated to dryness under reduced pressure, and an oily residue was powdered with a mixture of ethanol and acetone to give monopotassium salt of 3-(N-acetyl-N-hydroxyamino)-trans-1-propenylphosphonic acid (0.40 g.).

I.R. (Nujol): νmax: 1650, 1620 (shoulder), 1140 cm⁻¹.

N.M.R.: δppm in D₂O: 2.13 (3H, s), 4.35 (2H, m), 5.70-6.60 (2H, m).

(47) To an aqueous solution (45 ml.) of potassium alum (9.17 g.) was added mono sodium salt of 3-(N-formyl-N-hydroxyamino)propylphosphonic acid (3.08 g.) with stirring, and the solution was adjusted to pH 6-7 with 10% aqueous sodium hydroxide solution and then stirred for 2 hours at ambient temperature. The precipitating materials were collected by filtration, washed twice with water (each 10 ml.) and dried to give aluminum salt of 3-(N-formyl-N-hydroxyamino)propylphosphonic acid (2.28 g.).

I.R. (Nujol): νmax: 3700-2300, 1640, 1100, 920 cm⁻¹.

(48) (a) Preparation of the starting compound:

(1) Pulverized potassium carbonate (160 g.) was added to a solution of ethyl 2-hydroxyiminoacetoacetate (a mixture of syn and anti isomers) (152 g.) in acetone (500 ml.). Dimethyl sulfate (130 g.) was dropwise added thereto with stirring over 1 hour at 45° to 50° C. and the mixture was stirred for 2 hours. An insoluble material was filtered off and the filtrate was concentrated under reduced pressure. The filtered insoluble material was dissolved in water (500 ml.) and this solution was added to the residue. The mixture was extracted twice with ethyl acetate (300 ml.). The extract was washed twice with water (200 ml.) and with a saturated sodium chloride aqueous solution (200 ml.) and dried over magnesium sulfate. The solvent was distilled off under reduced pressure and the residue was distilled under reduced pressure to give colorless oil of ethyl 2-methoxyiminoacetoacetate (a mixture of syn and anti isomers) (145.3 g.), bp 55° to 64° C./0.5 mm Hg.

I.R. (Film): 1745, 1695, 1600 cm$^{-1}$.

N.M.R. (CDCl$_3$, δ): ppm: 4.33 (4H, q, J=8 Hz), 4.08 (3H, s), 3.95 (3H, s), 2.40 (3H, s), 1.63 (3H, s), 1.33 (6H, t, J=8 Hz).

(2) Sulfuryl chloride (235 ml.) was dropwise added over 20 minutes with stirring and ice-cooling to a solution of ethyl 2-methoxyiminoacetoacetate (syn isomer) (500 g.) in acetic acid (500 ml.), and the mixture was stirred overnight under cooling with water. Nitrogen gas was introduced to the reaction mixture for 2 hours, and the resulting mixture was poured into water (2.5 l.) After extracting with methylene chloride (500 ml.) and twice with methylene chloride (200 ml.), the extracts were combined. The combined extracts were washed with a saturated aqueous solution of sodium chloride, and adjusted to pH 6.5 by adding water (800 ml.) and sodium bicarbonate. Methylene chloride layer was separated, washed with an aqueous solution of sodium chloride and dried over magnesium sulfate. The solvent was distilled off to give ethyl 2-methoxyimino-4-chloroacetoacetate (syn isomer) (559 g.).

I.R. (Film): 1735, 1705 cm$^{-1}$.

(3) Ethyl 2-methoxyimino-4-chloroacetoacetate (syn isomer) (50 g.) was added over 3 minutes with stirring at ambient temperature to a solution of thiourea (18.4 g.) and sodium acetate (19.8 g.) in a mixture of methanol (250 ml.) and water (250 ml.). After stirring for 35 minutes at 40° to 45° C., the reaction mixture was cooled with ice and adjusted to pH 6.3 with a saturated aqueous solution of sodium bicarbonate. After stirring for 30 minutes at the same temperature, precipitates were collected by filtration, washed with water (200 ml.) and then with diisopropyl ether (100 ml.), and dried to give colorless crystals of ethyl 2-methoxyimino-2-(2-amino-1,3-thiazol-4-yl)acetate (syn isomer) (37.8 g.), mp 161° to 162° C.

I.R. (Nujol): 3400, 3300, 3150, 1725, 1630, 1559 cm$^{-1}$.

N.M.R. (CDCl$_3$, δ) ppm: 6.72 (1H, s), 5.91 (2H, broad s), 4.38 (2H, q, J=7 Hz), 4.03 (3H, s), 1.38 (3H, t, J=7 Hz).

(4) A mixture of acetic anhydride (6.1 g.) and formic acid (2.8 g.) was stirred for 2 hours at 50° C. The resulting mixture was cooled and ethyl 2-methoxyimino-2-(2-amino-1,3-thiazol-4-yl)acetate (syn isomer) (4.6 g.) was added thereto at 15° C. After the mixture was stirred for 3.5 hours at ambient temperature, cooled water (100 ml.) was added thereto. The resulting mixture was extracted with ethyl acetate (200 ml.). The extract was washed with water and then with a saturated aqueous solution of sodium bicarbonate until the washing was changed to weakly alkaline solution. The extract was further washed with a saturated aqueous solution of sodium chloride and dried over magnesium sulfate. The solvent was distilled off and the residue was washed with diisopropyl ether, collected by filtration and dried to give ethyl 2-methoxyimino-2-(2-formamido-1,3-thiazol-4-yl)acetate (syn isomer) (4.22 g.), mp 122° to 124° C. (dec.).

I.R. (Nujol): 3150, 1728, 1700 cm$^{-1}$.

N.M.R. (CDCl$_3$, δ) ppm: 12.58 (1H, broad s), 8.95 (1H, s), 7.17 (1H, s), 4.42 (2H, q, J=8 Hz), 4.00 (3H, s), 1.37 (3H, t, J=8 Hz).

(5) A solution of sodium hydroxide (1.6 g.) in water (30 ml.) was dropwise added over 5 minutes with stirring and ice-cooling to a suspension of ethyl 2-methoxyimino-2-(2-formamido-1,3-thiazol-4-yl)acetate (syn isomer) (5.14 g.) in water (60 ml.), and the resulting mixture was stirred for 1.5 hours at 10° to 20° C. The reaction mixture was adjusted to pH 7 with 10% hydrochloric acid and washed twice with ethyl acetate (100 ml.). To the aqueous layer was added ethyl acetate (200 ml.), and the resulting mixture was adjusted to pH 1 with 10% hydrochloric acid and extracted with the ethyl acetate. The aqueous layer was further extracted with ethyl acetate (100 ml.). Both ethyl acetate extracts were combined, washed with a sodium chloride aqueous solution (100 ml.) and dried over magnesium sulfate. The solvent was distilled off to give 2-methoxyimino-2-(2-formamido-1,3-thiazol-4-yl)acetic acid (syn isomer) (1.85 g.), mp 152° C. (dec.), which was recrystallized from ethyl acetate to give a pure compound, mp 167° C. (dec.).

I.R. (Nujol): 3200, 2800–2100, 1950, 1600 cm$^{-1}$.

N.M.R. (d$_6$-DMSO, δ) ppm: 8.60 (1H, s), 7.62 (1H, s), 3.98 (1H, s).

(b) Preparation of the object compound

Hydrochloric acid salt of 3-[N-{2-(2-amino-1,3-thiazol-4-yl)-2-methoxyiminoacetyl}-N-hydroxyamino]propylphosphonic acid (3.0 g) was obtained by reacting 3-(N-hydroxyamino)propylphosphonic acid (1.40 g) with 2-methoxyimino-2-(2-formamido-1,3-thiazol-4-yl)acetic acid (syn isomer) (2.29 g), N,N-dimethylformamide (0.80 g) and phosphorus oxychloride (1.69 g) in substantially the same manner as that of Example (39) and then hydrolyzing the resultant material with hydrochloric acid (2 ml).

N.M.R.: δppm in D$_2$O: 1.7–2.1 (4H, m), 3.7–3.9 (2H, t), 4.04 (3H, s), 7.04 (1H, s).

EXAMPLE FOR O-ACYLATION (1) A solution of benzoyl chloride (700 mg) in dry acetone (6 ml) was added dropwise to a solution of sodium salt of 3-(N-formyl-N-hydroxyamino)propylphosphonic acid (820 mg) in a mixture of water (15 ml) and acetone (15 ml) under ice-cooling, while stirring. During this period, pH of the mixture was kept at around 7.5–7.7 with 1 N aqueous sodium hydroxide solution.

The stirring was continued at the same temperature for 10 minutes and then acetone was evaporated under reduced pressure. The resulting aqueous solution was adjusted to pH 3.5 with 1 N hydrochloric acid and ether (40 ml) was added thereto. After removal of the precipitated impurities, the aqueous layer was adjusted to pH 1.6 with 1 N hydrochloric acid and extracted three times with ethyl acetate (50 ml, 20 ml×2). The combined ethyl acetate layer was washed with saturated aqueous sodium chloride solution, dried over magnesium sulfate and evaporated to dryness to give crystals, which were washed with ether to give crystalline 3-(N-benzoyloxy-N-formylamino)propylphosphonic acid (620 mg). Mp 149°–153° C. (dec.)

I.R. (Nujol): νmax: 3400–2100, 1765, 1630, 1250, 1135, 1035, 1010, 980 cm$^{-1}$.

N.M.R.: δ(ppm) in CD$_3$OD; 1.6–2.4 (4H, m), 3.92 (2H, t, J=6 Hz), 7.4–8.3 (5H, m), 8.35 (1H, s).

(2) Monosodium salt of 3-(N-formyl-N-hydroxyamino)propylphosphonic acid (2.05 g.) was dissolved in a mixture of 1 N aqueous sodium hydroxide solution (20 ml.), water (10 ml.) and acetone (10 ml.). To the solution was added dropwise a solution of p-chlorobenzoyl chloride (2.10 g.) in dry acetone (5 ml.) at 0°-5° C. with stirring. After the stirring was continued at the same temperature for 30 minutes, ethyl acetate (40 ml.) was added to the reaction mixture and then the resultant mixture was adjusted to pH 1 with 10% hydrochloric acid. The ethyl acetate layer was separated and then the aqueous layer was extracted again with ethyl acetate (20 ml.). The combined ethyl acetate layer was washed with aqueous sodium chloride solution, dried over magnesium sulfate and concentrated under reduced pressure to give an oily residue, which was crystallized with ethylether (40 ml.) to give crystals. The crystals were separated by filtration, washed twice with ethylether (10 ml.) to give crystalline 3-[N-(p-chlorobenzoyloxy)-N-formylamino]propylphosphonic acid (2.71 g.).

M.p. 133°-136° C. (dec.)

I.R. (Nujol): $\nu$max: 3600-2400, 1770, 1650, 1240, 1200, 1090, 1010, 970 cm$^{-1}$.

N.M.R.: $\delta$(ppm) in CD$_3$OD: 1.5-2.3 (4H, m), 3.90 (2H, t, J=6 Hz), 7.50, 8.08 (4H, AB$_q$, J$_{AB}$=15 Hz), 8.33 (1H, s).

(3) To a solution of monosodium salt of 3-(N-formyl-N-hydroxyamino)propylphosphonic acid (2.05 g.) in a mixture of 1 N aqueous sodium hydroxide solution (20 ml.) and acetone (10 ml.) was added dropwise a solution of n-butyryl chloride (1.56 g.) in acetone (7 ml.) at 0°-5° C. with stirring. After the stirring was continued at the same temperature for 30 minutes, the reaction mixture was concentrated under reduced pressure to give a formy residue. To the residue was added ethanol (50 ml.) to give insoluble materials, which were removed by filtration. The filtrate was concentrated under reduced pressure to give a residue, which was pulverized with acetone (30 ml.) to give powdery monosodium salt of 3-(N-formyl-N-n-butyryloxyamino)propylphosphonic acid (980 mg.).

I.R. (Nujol): $\nu$max: 3600-2200, 1795, 1690, 1160, 1070, 910, 895 cm$^{-1}$.

N.M.R.: $\delta$(ppm) in D$_2$O: 1.00 (3H, t, J=7 Hz), 1.4-2.1 (6H, m), 2.58 (2H, t, J=7 Hz), 3.76 (2H, t, J=6 Hz), 8.20 (1H, s).

EXAMPLE FOR ESTERIFICATION (1) Diazomethane in ethyl ester was added dropwise to a solution of 3-(N-acetyl-N-hydroxyamino)propylphosphonic acid (600 mg) in methanol (20 ml) under ice-cooling until yellow color of diazomethane in the reaction mixture didn't disappear. The solvent was distilled off from the solution under reduced pressure. The obtained residue was subjected to column chromatography on silica gel with an eluent (a mixture of 19 parts of chloroform and one part of methanol by volume). The fractions containing the object compound were collected and concentrated under reduced pressure to give a residual oil (350 mg). This purification operation was repeated once again to give dimethyl 3-(N-acetyl-N-hydroxyamino)propylphosphonate (260 mg).

Infrared Absorption Spectrum (liquid film): $\nu_{max}$=2600~3600, 1640, 1230, 1030 cm$^{-1}$.

| NMR Absorption Spectrum (CDCl$_3$): | |
|---|---|
| 1.6~2.2 | (4H, m) |

| NMR Absorption Spectrum (CDCl$_3$): | |
|---|---|
| 2.13 | (3H, s) |
| 3.66 | (1H, t, J=6Hz) |
| 3.70 | (6H, d, J=10Hz) |
| 9.65 | (1H, broad s) |

(2) To a solution of monosodium salt of 3-(N-formyl-N-hydroxyamino)propylphosphonic acid (2.05 g.) in a mixture of water (10 ml.) and methanol (50 ml.) was added dropwise a solution of diazomethane in ethyl ether under ice-cooling with stirring until the above phosphonic acid was not detected by a thin-layer chromatography on silica gel. After the reaction was completed, the reaction mixture was concentrated under reduced pressure to give a formyl residue. To the residue was added ethanol (50 ml.) to give insoluble materials, which were removed by filtration. The ethanolic solution was concentrated under reduced pressure to give a residue, which was pulverized with acetone to give crude powder (1.47 g.). The powder was dissolved in methanol (10 ml.) and to the solution was added isopropyl alcohol (40 ml.) to give precipitates. The mixture was stirred for 6 hours at ambient temperature, and the precipitates were separated by filtration and washed twice with isopropyl alcohol (5 ml.) to give powdery monosodium salt of methyl 3-(N-formyl-N-hydroxyamino)propylphosphonate (470 mg.). The object compound (330 mg.) was also recovered from the filtrate and washings by concentrating them to a volume of 10 ml.

I.R. (Nujol): $\nu$max: 3600-2200, 1660, 1230, 1190, 1040, 880 cm$^{-1}$.

| N.M.R. $\delta$(ppm) in D$_2$O: | 1.2-2.2 (4H, m) |
|---|---|
| | 3.58 (3H, d, J = 10Hz) |
| | 3.75 (2H, t, J = 6Hz) |
| | 7.97 (s) $\Big\}$ 1H |
| | 8.30 (s) |

(3) Dimethyl 3-(N-formyl-N-hydroxyamino)-2-hydroxypropylphosphonate (170 mg) was obtained by reacting 3-(N-formyl-N-hydroxyamino)-2-hydroxypropylphosphonic acid (200 mg) with diazomethane in substantially the same manner as that of Example (1).

N.M.R.: $\delta$ppm in CDCl$_3$: 2.17 (2H, d, d, J=6 and 18 Hz), 2.20 (3H, s), 3.81 (6H, d, J=11 Hz), 3.6-3.9 (2H, m), 4.35 (1H, m).

FORMATION OF C-S BOND (1) A mixture of 3-[N-(2-chloroacetyl)-N-hydroxyamino]propyl phosphonic acid (232 mg), water (2 ml), D,L-cysteine hydrochloride (176 mg) was adjusted to pH 8 with 1 N aqueous sodium hydroxide solution and stirred at ambient temperature for 5 hours. The reaction mixture was adjusted to pH 3 with 1 N hydrochloric acid, and ethanol (5 ml) was added. This mixture was allowed to stand overnight in a refrigerator (4° C.) to give crystals, which were separated by filtration, washed with ethanol and then dried to give crystalline 3-[N-{2-amino-2-carboxyethylthio)acetyl}-N-hydroxyamino]propylphosphonic acid (240 mg). Mp 167°-169.5° C. (dec.).

I.R. (Nujol): $\nu$max: 3600-2000, 1635, 1600, 1580, 1220, 1170, 1030, 960 cm$^{-1}$.

N.M.R.: δ(ppm) in D₂O; 1.4–2.1 (4H, m), 3.1–3.3 (2H, m), 3.64 (4H, broad s), 4.02 (1H, t, J=6 Hz).

EXAMPLES FOR THE ANTIMICROBIAL COMPOSITION (i) Preparation for injection (1) The required quantities of sterile antibiotic, monosodium salt of 3-(N-formyl-N-hydroxyamino)propylphosphonic acid were distributed into vials, thereby containing 250 mg. of the active ingredient. The vials were sealed hermetically to exclude bacteria. Whenever the vials are required for use, 2 ml. of a sterile distilled water for injection is added to the vial and the vial is subjected to administration.

In substantially the same manner as described in the above example (1), there was prepared an injection preparation of an antibiotic as illustrated in the following Example (2) to (4).

(2) Monopotassium salt of 3-(N-formyl-hydroxyamino)trans-1-propenylphosphonic acid (250 mg.) was used as the active ingredient for injection.

(3) Monosodium salt of 3-(N-acetyl-N-hydroxyamino)-2-trans-1-propenylphosphonic acid (500 mg.) was used as the active ingredient for injection.

(4) Monopotassium salt of 3-(N-formyl-N-hydroxyamino)-2-hydroxypropylphosphonic acid (250 mg.) was used as be active ingredient for injection.

(ii) Preparation for tablet (1) A suitable formulation of a tablet consists of the following mixture.

| | |
|---|---|
| Monosodium salt of 3-(N-formyl-N-hydroxyamino)propylphosphonic acid | 200 mg. |
| Mannitol | 400 mg. |
| Starch | 50 mg. |
| Magnesium stearate | 10 mg. |

(iii) Preparation for capsule

| | |
|---|---|
| Monopotassium salt of 3-(N-formyl-N-hydroxyamino)propylphosphonic acid | 300 mg. |
| Magnesium stearate | 15 mg. |

The above ingredients were mixed and then inserted into a hard gelatin capsule in a conventional manner.

(iv) Preparation for oily suspension

| | |
|---|---|
| Monosodium salt of 3-(N-formyl-N-hydroxyamino)propylphosphonic acid | 200 mg. |
| Lanette wax SX (trade name) | 50 mg. |
| Soft paraffin | 100 mg. |
| Brilliant blue FCF | 25 mg. |

The above ingredients were mixed with liquid paraffin so as to be totally 3 g. to give an infusion preparation.

We claim:

1. A pharmaceutical composition which comprises, as an effective ingredient, at least one compound having antibacterial activity against pathogenic bacteria of the formula:

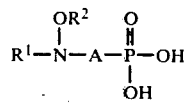

wherein
R¹ is hydrogen or the acyl moiety of an organic carboxylic acid
R² is hydrogen, or the acyl moiety of an organic carboxylic acid, and
A is lower alkylene, lower alkenylene or hydroxy(lower)alkylene, or the pharmaceutically acceptable salt thereof excepting 3-(N-acetyl-N-hydroxyamino)propylphosphonic acid, 3-(N-acetyl-N-hydroxyamino)-2-hydroxypropylphosphonic acid, and their pharmaceutically acceptable salts with a pharmaceutically acceptable carrier.

2. A pharmaceutical composition according to claim 1 wherein
R¹ is the acyl moiety of an organic carboxylic acid,
R² is hydrogen and
A is lower alkylene, lower alkenylene or hydroxy(lower)alkylene or the pharmaceutically acceptable salts thereof.

3. A pharmaceutical composition according to claim 2, wherein
R¹ is lower alkanoyl, and
A is lower alkylene, lower alkenylene or hydroxy(lower) alkylene.

4. A pharmaceutical composition according to claim 3, wherein
R¹ is formyl, and
A is trimethylene, propenylene or hydroxytrimethylene.

5. A method of treating a host containing an infectious disease caused by pathogenic bacteria which comprises treating the host with a therapeutically effective amount of the composition of claim 1.

6. A method of treating a host containing an infectious disease caused by pathogenic bacteria which comprises treating the host with a therapeutically effective amount of the composition of claim 2.

7. A method of treating a host containing an infectious disease caused by pathogenic bacteria which comprises treating the host with a therapeutically effective amount of the composition of claim 3.

8. A method of treating a host containing an infectious disease by pathogenic bacteria which comprises treating the host with a therapeutically effective amount of the composition of claim 4.

9. The composition of claim 1 in the form of a tablet, pelett, capsule, suppository, solution, emulsion or aqueous suspension for parenteral administration.

10. A pharmaceutical composition according to claim 4 wherein A is trimethylene.

11. A method of treating a host containing an infectious disease caused by pathogenic bacteria which comprises treating the host with a therapeutically effective amount of the composition of claim 10.

12. A compound of the formula:

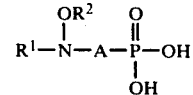

wherein
R¹ is hydrogen or acyl,
R² is hydrogen, ar(lower) alkyl or acyl, and
A is lower alkylene, lower alkenylene or hydroxy(lower) alkylene, or the esters at the phosphono group thereof or the pharmaceutically acceptable salts thereof, excepting 3-(N-acetyl-N-hydroxyamino)propylphosphonic acid, 3-(N-acetyl-N-hydroxyamino)-2-hydroxypropylphosphonic acid, and their pharmaceutically acceptable salts, wherein each of said acyl groups is the acyl moiety of an organic carboxylic acid.

13. A compound according to claim 12, having activity against pathogenic bacteria which is the compound of the formula:

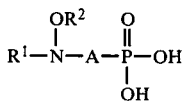

wherein $R^1$ is hydrogen or the acyl moiety of an organic carboxylic acid $R^2$ is hydrogen, and A is lower alkylene, lower alkenylene or hydroxy (lower) alkylene, or the pharmaceutically acceptable salt thereof.

14. A compound according to claim 13, wherein the compound is the inorganic salt thereof.

15. A compound according to claim 14, wherein the inorganic salt is a salt selected from the group of sodium salt, potassium salt, calcium salt, magnesium salt and ammonium salt.

16. A compound according to claim 13, wherein the compound is the organic salt thereof.

17. A compound according to claim 16, wherein the compound is a salt selected from the group of ethanolamine salt, ethylenediamine salt, N,N'-dibenzylethylenediamine salt and arginine salt.

18. A compound according to claim 13, wherein A is lower alkylene.

19. A compound according to claim 13, wherein $R^1$ is lower alkanoyl, and A is lower alkylene.

20. A compound according to claim 19, which is 3-(N-formyl-N-hydroxyamino)propylphosphonic acid.

21. A compound according to claim 19, which is the sodium, potassium, calcium, magnesium, ammonium, ethanolamine, ethylene diamine, N,N'-dibenzylethylenediamine or arginine salt of 3-(N-formyl-N-hydroxyamino)propylphosphonic acid.

22. A compound according to claim 13, wherein A is lower alkenylene.

23. A compound according to claim 13, wherein $R^1$ is lower alkanoyl, and A is lower alkenylene.

24. A compound according to claim 23, wherein $R^1$ is formyl or acetyl, and A is propenylene.

25. A compound according to claim 24, wherein the salt is the sodium or potassium salt.

26. A compound according to claim 24, which is 3-(N-formyl-N-hydroxyamino)-trans-1-propenylphosphonic acid.

27. A compound according to claim 25, which is the sodium or potassium salt of 3-(N-formyl-N-hydroxyamino)-trans-1-propenylphosphonic acid.

28. A compound according to claim 24, which is 3-(N-acetyl-N-hydroxyamino)-trans-1-propenylphosphonic acid.

29. A compound according to claim 24, which is the potassium salt of 3-(N-acetyl-N-hydroxyamino)-trans-1-propenylphosphonic acid.

30. A compound according to claim 13, wherein A is hydroxy(lower)alkylene.

31. A compound according to claim 13, wherein $R^1$ is lower alkanoyl, and A is hydroxy(lower)alkylene.

32. A compound according to claim 31, wherein $R^1$ is formyl or acetyl, and A is hydroxytrimethylene.

33. A compound according to claim 32, wherein the salt is the sodium or ammonium salt.

34. A compound according to claim 32, which is 3-(N-formyl-N-hydroxyamino)-2-hydroxypropylphosphonic acid.

35. A compound according to claim 33, which is the sodium or ammonium salt of 3-(N-formyl-N-hydroxyamino)-2-hydroxypropylphosphonic acid.

36. A compound according to claim 12, wherein $R^1$ is hydrogen.

37. A compound according to claim 12, wherein $R^1$ and $R^2$ are each hydrogen.

38. A compound according to claim 36, wherein A is lower alkylene.

39. A compound according to claim 38, which is (N-hydroxyamino) (lower) alkylphosphonic acid.

40. A compound according to claim 38, wherein A is trimethylene.

41. A compound according to claim 39, which is 3-(N-hydroxyamino)propylphosphonic acid.

42. A compound according to claim 36, wherein A is lower alkenylene.

43. A compound according to claim 42, which is (N-hydroxyamino) (lower)alkenylphosphonic acid.

44. A compound according to claim 42, wherein A is propenylene.

45. A compound according to claim 44, which is 3-(N-hydroxyamino)-trans-1-propenylphosphonic acid.

46. A compound according to claim 36, wherein A is hydroxy(lower)alkylene.

47. A compound according to claim 46, which is (N-hydroxyamino)hydroxy(lower)alkylphosphonic acid.

48. A compound according to claim 46, wherein A is hydroxytrimethylene.

49. A compound according to claim 48, which is 2-hydroxy-3-(N-hydroxyamino)propylphosphonic acid.

50. A compound according to claim 12, which is the ester at the phosphono group of the compound of the formula:

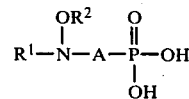

wherein $R^1$, $R^2$ and A are as defined in the claim 12.

51. A compound according to claim 50, which is the compound of the formula:

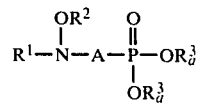

wherein R¹, R² and A are as defined in the claim 50, and R$_a$³ is a residue of the ester.

52. A compound according to claim 51, wherein R$_a$³ is lower alkyl, ar(lower)alkyl aryl, or a residue of the silyl compound, each of which may have possible substituent.

53. A compound according to claim 51, wherein
R¹ is lower alkanoyl, and
A is lower alkylene, lower alkenylene or hydroxy(lower) alkylene.

54. A compound according to claim 53, wherein
R¹ is formyl or acetyl, and
A is trimethylene, propenylene or hydroxytrimethylene.

55. A compound according to claim 50, which is the compound of the formula:

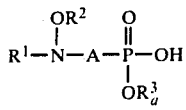

wherein R¹, R² and A are as defined in claim 45, and R$_a$³ is a residue of the ester.

56. A compound according to claim 55, wherein
R¹ is hydrogen or lower alkanoyl,
R² is hydrogen,
A is lower alkylene, and
R$_a$³ is lower alkyl.

57. A compound according to claim 56, wherein
R¹ is hydrogen or formyl,
R$_a$³ is methyl or ethyl, and
A is trimethylene.

58. A compound according to claim 57, which is methyl 3-(N-formyl-N-hydroxyamino)propylphosphonate.

59. A compound according to claim 57, which is ethyl 3-(N-formyl-N-hydroxyamino)propylphosphonate.

60. A compound according to claim 57, which is ethyl 3-(N-hydroxyamino)propylphosphonate.

61. A compound according to claim 51 wherein R¹ and R² are each hydrogen.

* * * * *

UNITED STATES PATENT AND TRADEMARK OFFICE
CERTIFICATE OF CORRECTION

PATENT NO. : 4,182,758

DATED : January 8, 1980

INVENTOR(S) : KAMIYA et al

It is certified that error appears in the above—identified patent and that said Letters Patent is hereby corrected as shown below:

Column 8, line 68, delete "isoporyplidene" and insert --isopropylidene--.

Column 10, line 30, delete "pre" and insert --Pre--.

Column 12, line 55, delete "dialkylphosphoricc" and insert --dialkylphosphoric--.

Column 13, line 26, delete "triazotriphorine" and insert --triaztriphosphorine--.

Column 17, line 64, delete "pechogenic" and insert --pathogenic--.

Column 20, line 37, delete "glutanic" and insert --glutamic--.

Column 21, line 19, delete "(4) Halogenation (II)".

Column 25, line 61, delete "pridine" and insert --pyridine--.

Column 30, line 15, delete "200" and insert --2.00--.

UNITED STATES PATENT AND TRADEMARK OFFICE
CERTIFICATE OF CORRECTION

PATENT NO. : 4,182,758
DATED : January 8, 1980
INVENTOR(S) : KAMIYA et al

It is certified that error appears in the above—identified patent and that said Letters Patent is hereby corrected as shown below:

Column 31, line 47, delete "N-ethoxycarbonyloxycarbomate" and insert -- -N-ethoxycarbonyloxycarbamate--.

Column 32, line 20, delete "1.2-2.5" and insert --1.2-2.6--.

Column 41, line 38, delete "track" and insert --trade--.

Column 56, line 28, delete "carbomoyl" and insert --carbamoyl--.

Column 64, line 49, delete "the" and insert --The--.

Column 69, line 35, delete "formy" and insert --foamy--.

Column 76, line 7, in Claim 55, after the formula for "45" insert --50--.

Signed and Sealed this

Tenth Day of February 1981

[SEAL]

Attest:

RENE D. TEGTMEYER

Attesting Officer

Acting Commissioner of Patents and Trademarks